US011951131B2

(12) United States Patent
Kochenderfer et al.

(10) Patent No.: US 11,951,131 B2
(45) Date of Patent: Apr. 9, 2024

(54) ANTI-SLAMF7 CHIMERIC ANTIGEN RECEPTORS

(71) Applicant: The United States of America, as represented by the Secretary,Department of Health and Human Services, Bethesda, MD (US)

(72) Inventors: James N. Kochenderfer, Bethesda, MD (US); Steven A. Feldman, Redwood City, CA (US)

(73) Assignee: The United States of America, as represented by the Secretary, Department of Health and Human Services, Bethesda, MD (US)

( * ) Notice: Subject to any disclaimer, the term of this patent is extended or adjusted under 35 U.S.C. 154(b) by 200 days.

(21) Appl. No.: 17/255,005

(22) PCT Filed: Jun. 26, 2019

(86) PCT No.: PCT/US2019/039239
§ 371 (c)(1),
(2) Date: Dec. 22, 2020

(87) PCT Pub. No.: WO2020/009868
PCT Pub. Date: Jan. 9, 2020

(65) Prior Publication Data
US 2021/0260125 A1 Aug. 26, 2021

Related U.S. Application Data

(60) Provisional application No. 62/693,779, filed on Jul. 3, 2018.

(51) Int. Cl.
*A61K 35/17* (2015.01)
*A61P 35/00* (2006.01)
*C07K 14/705* (2006.01)
*C07K 14/725* (2006.01)

(52) U.S. Cl.
CPC .............. *A61K 35/17* (2013.01); *A61P 35/00* (2018.01); *C07K 14/7051* (2013.01); *C07K 14/70517* (2013.01); *C07K 14/70521* (2013.01)

(58) Field of Classification Search
None
See application file for complete search history.

(56) References Cited

U.S. PATENT DOCUMENTS

| 8,871,906 | B2 | 10/2014 | Pastan et al. |
| 2006/0024296 | A1 | 2/2006 | Williams et al. |
| 2013/0007414 | A1 | 3/2013 | Dotti et al. |
| 2019/0112380 | A1* | 4/2019 | Chaudhary ............ A61K 45/06 |

FOREIGN PATENT DOCUMENTS

| WO | WO 2014/179759 A1 | 11/2014 |
| WO | WO 2015/166056 A1 | 11/2015 |
| WO | WO 2016/090369 A1 | 6/2016 |
| WO | WO 2017/066122 | 4/2017 |
| WO | WO 2017/222593 A1 | 12/2017 |

OTHER PUBLICATIONS

Yu et al. Journal of Hematology & Oncology (2017) 10:78. (Year: 2017).*
Alabanza et al., "Function of Novel Anti-CD19 Chimeric Antigen Receptors with Human Variable Regions Is Affected by Hinge and Transmembrane Domains," *Molecular Therapy* 25(11): 2452-2465 (2017).
Ali et al., "T Cells Expressing An Anti-B-Cell Maturation Antigen Chimeric Antigen Receptor Cause Remissions of Multiple Myeloma," *Blood* 128(13): 1688-1700 (2016).
Ayed et al., "Immunotherapy for multiple myeloma: Current status and future directions," *Critical Reviews in Oncology/Hematology* 96(3): 399-412 (2015).
Beatty et al., "Mesothelin-Specific Chimeric Antigen Receptor Mrna-Engineered T Cells Induce Anti-Tumor Activity in Solid Malignancies," *Cancer Immunol. Res.* 2(2): 112-120 (Feb. 2014) Author Manuscript.
Belshaw et al., "Controlling Programmed Cell Death With a Cyclophilin-Cyclosporin-Based Chemical Inducer of Dimerization," *Chemistry & Biology* 3(9): 731-738 (Sep. 1996).
Boles et al. "Molecular cloning of CS1, a novel human natural killer cell receptor belonging to the CD2 subset of the immunoglobulin superfamily," *Immunogenetics* 52: 302-307 (2001).
Brentjens et al. "CD19-targeted T Cells Rapidly Induce Molecular Remissions in Adults With Chemotherapy-Refractory Acute Lymphoblastic Leukemia," *Sci. Transl. Med.* 5(177) (2013) Author Manuscript.
Brudno et al. "Allogeneic T Cells That Express An Anti-CD19 Chimeric Antigen Receptor Induce Remissions Of B-Cell Malignancies That Progress After Allogeneic Hematopoietic Stem-Cell Transplantation Without Causing Graft-Versus-Host Disease," *J. Clin. Oncol.* 34(10): 1112-1121 (2016).
Brudno et al. "Toxicities of chimeric antigen receptor T Cells: recognition and management," *Blood* 127(26): 3321-3330 (2016).
Brudno et al. "T cells Modified to Express an Anti-B-cell Maturation Antigen Chimeric Antigen Receptor Cause Remissions of Poor-prognosis Relapsed Multiple Myeloma," *J. Clin. Oncol.* 36(22): 2267-2280 (2018).
Calpe et al. "The SLAM and SAP Gene Families Control Innate and Adaptive Immune Responses," *Advances in Immunology.* 97: 177-250 (2008).

(Continued)

*Primary Examiner* — Allison M Fox
*Assistant Examiner* — Alyssa G Weston
(74) *Attorney, Agent, or Firm* — Leydig, Voit & Mayer

(57) ABSTRACT

Provided are chimeric antigen receptors (CARs) having antigenic specificity for B-cell Maturation Antigen (SLAMF7). Also provided are related nucleic acids, recombinant expression vectors, host cells, populations of cells, and pharmaceutical compositions relating to the CARs. Methods of treating or preventing cancer in a mammal are also provided.

Figure 1A:
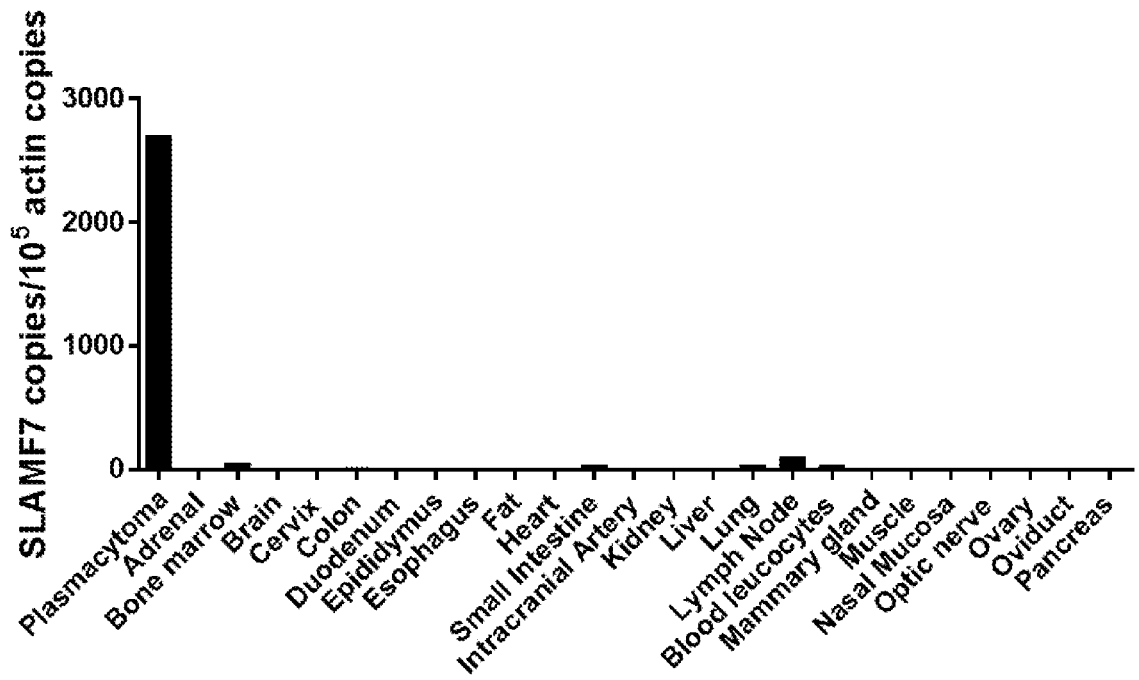

16 Claims, 18 Drawing Sheets
Specification includes a Sequence Listing.

(56) References Cited

OTHER PUBLICATIONS

Carpenter et al. "B-Cell Maturation Antigen Is a Promising Target for Adoptive T-Cell Therapy of Multiple Myeloma," *Clin. Cancer Res.* 19(8): 2048-2060 (2013) author manuscript.

Clackson et al. "Redesigning An FKBP-Ligand Interface to Generate Chemical Dimerizers With Novel Specificity," *Proc. Natl, Acad. Sci. USA*, 95(18): 10437-10442 (1998).

Chang et al. "Chimeric Antigen Receptor-Modified T Cells Against Several Target Antigens in Multiple Myeloma," *Cancer Research* 75(15 Supplement): 3149-3149 (2015), Abstract No. 3149.

Chen et al., "Genetic Control of Mammalian T-Cell Proliferation With Synthetic RNA Regulatory Systems," *PNAS* 107(19): 8531-8536 (May 2010).

Chen et al. "A Compound Chimeric Antigen Receptor Strategy for Targeting Multiple Myeloma," *Leukemia* 32(2):402-412 (2018).

Chu et al. "CS1-Specific Chimeric Antigen Receptor (CAR)-Engineered Natural Killer Cells Enhance In Vitro and In Vivo Antitumor Activity Against Human Multiple Myeloma," *Leukemia* 28(4): 917-927 (2014) Author Manuscript.

Chu et al. "Genetic Modification of T Cells Redirected Toward CS1 Enhances Eradication of Myeloma Cells," *Clin. Cancer Res.* 20(15): 3989-4000 (2014) Author Manuscript.

Di Stasi et al. "Inducible Apoptosis as a Safety Switch for Adoptive Cell Therapy," *N. Engl. J. Med.* 365(18): 1673-1683 (2011) Author Manuscript.

Duckert et al., "Prediction of proprotein convertase cleavage sites," *Protein Engineering, Design & Selection* 17(1): 107-112 (Jan. 2004).

Esensten et al., "Engineering Therapeutic T Cells: From Synthetic Biology to Clinical Trials," *Annu. Rev. Pathol.* 12: 305-330 (Jan. 2017) Author Manuscript.

Eshhar et al. "Specific Activation and Targeting of Cytotoxic Lymphocytes Through Chimeric Single Chains Consisting of Antibody-Binding Domains and the γ or ζ subunits of The Immunoglobulin And T-Cell Receptors," *Proc. Natl. Acad. Sci. USA*, 90(2):720-724 (1993).

European Patent Office, International Search Report in International Patent Application No. PCT/US2019/039239, dated Nov. 22, 2019 (9 pgs.).

European Patent Office, Written Opinion of the International Searching Authority in International Patent Application No. PCT/US2019/039239, dated Nov. 22, 2019, 8 pages.

Fedorov et al., "PD-1- and CTLA-4-Based Inhibitory Chimeric Antigen Receptors (Icars) Divert Off-Target Immunotherapy Responses," *Sci. Transl. Med.* 5(215): 215ra172 (Dec. 2013) Author Manuscript.

Gargett et al. "The Inducible Caspase-9 Suicide Gene System as a 'Safety Switch' to Limit On-Target, Off-Tumor Toxicities of Chimeric Antigen Receptor T Cells," *Frontiers in Pharmacology* 5(235): 1-7 (2014).

Genbank accession NM_001229 (printed Nov. 23, 2003).

Genbank Accession No. AH002818 (printed Jun. 10, 2016).

Gogishvili et al. "SLAMF7-CAR T Cells Eliminate Myeloma and Confer Selective Fratricide of SLAMF7$^+$ Normal Lymphocytes," *Blood* 130(26): 2838-2847 (2017).

Griffioen et al., "Retroviral Transfer of Human CD20 as a Suicide Gene for Adoptive T-Cell Therapy," *Haematologica* 94(9): 1316-1320 (Sep. 2009).

Hsi et al. "CS1, a Potential New Therapeutic Antibody Target for the Treatment of Multiple Myeloma," *Clin. Cancer Res.* 14(9): 2775-2784 (2008) Author Manuscript.

Hughes et al. "Transfer of a TCR Gene Derived From a Patient With a Marked Antitumor Response Conveys Highly Active T-Cell Effector Functions," *Hum. Gene Ther.* 16(4): 457-472 (2005) Author Manuscript.

Iuliucci et al. "Intravenous Safety and Pharmacokinetics of a Novel Dimerizer Drug, AP1903, In Healthy Volunteers," *J. Clin. Pharmacol.* 41(8): 870-879 (2001).

Jakubowiak, "Management Strategies for Relapsed/Refractory Multiple Myeloma: Current Clinical Perspectives," *Seminars in Hematology* 49: S16-S32 (2012).

Jakubowiak et al., "Randomized Phase 2 Study: Elotuzumab Plus Bortezomib/Dexamethasone Vs Bortezomib/Dexamethasone For Relapsed/Refractory MM," *Blood* 127(23): 2833-2840 (2016).

Jensen et al., "Designing chimeric antigen receptors to effectively and safely target tumors," *Curr. Opin. Immunol.* 33: 9-15 (2016) Author Manuscript.

Kieback et al., "A safeguard eliminates T cell receptor gene-modified autoreactive T cells after adoptive transfer," *PNAS* 105(2): 623-628 (Jan. 2008).

Kim et al. "CS1 (SLAMF7) Inhibits Production of Proinflammatory Cytokines by Activated Monocytes," *Inflamm. Res.* 62: 765-772 (2013).

Kochenderfer et al., "Construction and Preclinical Evaluation of an Anti-CD19 Chimeric Antigen Receptor," *J. Immunother.* 32(7):689-702 (2009) Author Manuscript.

Kochenderfer et al., "Eradication of B-Lineage Cells and Regression of Lymphoma in a Patient Treated With Autologous T Cells Genetically Engineered to Recognize CD19", *Blood* 116(20): 4099-4102 (2010).

Kochenderfer et al., "B-cell Depletion and Remissions of Malignancy Along With Cytokine-Associated Toxicity in a Clinical Trial of Anti-CD19 Chimeric-Antigen-Receptor-Transduced T Cells," *Blood* 119(12): 2709-2720 (2012).

Kochenderfer et al. "Treating B-cell Cancer With T Cells Expressing Anti-CD19 Chimeric Antigen Receptors," *Nat. Rev. Clin. Oncol.* 10(5): 267-276 (2013) Author Manuscript.

Kochenderfer et al. "Lymphoma Remissions Caused by Anti-CD19 Chimeric Antigen Receptor T Cells Are Associated With High Serum Interleukin-15 Levels," *J. Clin. Oncol.* 35(16): 1803-1813 (2017).

Lamers et al. "Treatment of Metastatic Renal Cell Carcinoma With Autologous T-Lymphocytes Genetically Retargeted Against Carbonic Anhydrase IX: First Clinical Experience," *Journal of Clinical Oncology.* 24(13):e20-22 (2006).

Laubach et al. "Management of relapsed and relapsed/refractory multiple myeloma", *JNCCN Journal of the National Comprehensive Cancer Network* 9(10): 1209-1216 (2011).

Lee et al. "T Cells Expressing CD19 Chimeric Antigen Receptors for Acute Lymphoblastic Leukaemia in Children and Young Adults: A Phase 1 Dose-Escalation Trial," *Lancet.* 385(9967): 517-528 (2015) Author Manuscript.

Liu et al., "Systematic Comparison of 2A Peptides for Cloning Multi-Genes in a Polycistronic Vector," *Scientific Reports*, 7(1): 2193, 1-9 (May 2017).

Lonial et al. "Treatment Options for Relapsed and Refractory Multiple Myeloma," *Clin. Cancer Res.* 17(6): 1264-1277 (2011).

Lonial et al. "Elotuzumab Therapy for Relapsed or Refractory Multiple Myeloma," *New England Journal of Medicine.* 373(7): 621-631 (2015).

Lonial et al. "Update on Elotuzumab, A Novel Anti-SLAMF7 Monoclonal Antibody for the Treatment of Multiple Myeloma," *Expert Opinion on Biological Therapy.* 16(10):1291-1301 (2016).

Malaer et al. "CS1 (SLAMF7, CD319) is an Effective Immunotherapeutic Target for Multiple Myeloma," *Am. J. Cancer Res.* 7(8): 1637-1641 (2017).

Mannering et al. "A Sensitive Method for Detecting Proliferation of Rare Autoantigen- Specific Human T Cells," *Journal of Immunological Methods.* 283(1-2): 173-183 (2003).

Mathur et al. "Universal SLAMF7-Specific CAR T-Cells as Treatment for Multiple Myeloma," *ASH Annual Meeting*, Abstract 502, 1-15 (2017).

Maude et al. "Chimeric Antigen Receptor T Cells for Sustained Remissions in Leukemia," *N. Engl. J. Med.* 371(16):1507-1517 (2014) Author Manuscript.

Mikkilineni et al. "Chimeric Antigen Receptor T-Cell Therapies for Multiple Myeloma," *Blood* 130 (24): 2594-2602 (2017).

Morgan et al. "Case Report of a Serious Adverse Event Following the Administration of T Cells Transduced With a Chimeric Antigen Receptor Recognizing ERBB2," *Molecular Therapy* 18(4):843-851 (2010).

(56) References Cited

OTHER PUBLICATIONS

Orange, JS. "Human natural killer cell deficiencies and susceptibility to infection," *Microbes and Infection.* 4: 1545-1558 (2002).
Orange, "Natural Killer Cell Deficiency," *J. Allergy Clin. Immunol.* 132(3):515- 526 (2013) Author Manuscript.
Philip et al., "A Highly Compact Epitope-Based Marker/Suicide Gene for Easier and Safer T-Cell Therapy," *Blood* 124(8): 1277-1287 (Aug. 2014).
Rajkumar, "Treatment of multiple myeloma," *Nat. Rev. Clin. Oncol.* 8(8):479- 491 (2011) Author Manuscript.
Ramos et al. "CD19-CAR Trials," *Cancer J.* 20(2):112-118 (2014) Author Manuscript.
Rubio et al. "Ex vivo identification, Isolation and Analysis of Tumor-Cytolytic T Cells," *Nature Medicine* 9(11):1377-1382 (2003).
Sadelain et al. "The Basic Principles of Chimeric Antigen Receptor Design," *Cancer Discov.* 3(4): 388-398 (2013).
Simmons et al. "Molecular Cloning of a Cdna Encoding CD34, A Sialomucin of Human Hematopoietic Stem Cells," *Journal of immunology* 148(1): 267-271 (1992).
Spencer et al., "Functional Analysis of Fas Signaling In Vivo Using Synthetic Inducers of Dimerization," *Current Biology* 6(7): 839-847 (Jul. 1996).
Straathof et al. "An Inducible Caspase 9 Safety Switch for T-Cell Therapy," *Blood* 105(11): 4247-4254 (2005).
Szymczak et al. "Correction of Multi-Gene Deficiency In Vivo Using a Single 'Self-Cleaving' 2A Peptide-Based Retroviral Vector," *Nature Biotechnology* 22(5): 589-594 (2004).
Tai et al. "Anti-CS1 Humanized Monoclonal Antibody Huluc63 Inhibits Myeloma Cell Adhesion and Induces Antibody-Dependent Cellular Cytotoxicity in the Bone Marrow Milieu," *Blood* 112(4): 1329-1337 (2008).

The International Bureau of WIPO, International Preliminary Report on Patentability in PCT/US2019/039239 dated Jan. 5, 2021, 9 pages.
Thomis et al., "A Fas-Based Suicide Switch in Human T Cells for the Treatment of Graft-Versus-Host Disease," *Blood* 97(5): 1249-1257 (Mar. 2001).
Veillette et al. "CS1, a SLAM Family Receptor Involved in Immune Regulation, Is a Therapeutic Target in Multiple Myeloma," *Critical Reviews in Oncology/Hematology* 88: 168-177 (2013).
Wang et al., "A Transgene-Encoded Cell Surface Polypeptide for Selection, In Vivo Tracking, and Ablation of Engineered Cells," *Blood* 118(5): 1255-1263 (Aug. 2011).
Wang et al. "Lenalidomide Enhances the Function of CS1 Chimeric Antigen Receptor-Redirected T Cells Against Multiple Myeloma," *Clin. Cancer Res.* 24(1): 106-119 (2017) Author Manuscript.
Woof et al., "Human Antibody-Fc Receptor Interactions Illuminated By Crystal Structures," *Nature Reviews Immunology* 4(2): 89-99 (Feb. 2004).
Wu et al., "Remote Control of Therapeutic T Cells Through a Small Molecule-Gated Chimeric Receptor," *Science*, 350(6258): (Oct. 2015) Author Manuscript.
Wu et al. "SLAM Family Receptors in Normal Immunity and Immune Pathologies," *Current Opinion in Immunology* 38: 45-51 (2016).
Zonder et al. "A Phase 1, Multicenter, Open-Label, Dose Escalation Study of Elotuzumab in Patients With Advanced Multiple Myeloma," *Blood* 120(3): 552-559 (2012).
Jena et al., "Redirecting T-cell specificity by introducing a tumor-specific chimeric antigen receptor", *Blood*, 116(7): 1035-1044 (2010).
Amatya et al., "Development of CAR T Cells Expressing a Suicide Gene Plus a Chimeric Antigen Receptor Targeting Signaling Lymphocytic-Activation Molecule F7", *Molecular Therapy*, 29(2): 1-16 (2020).

\* cited by examiner

SEQUENCE LISTING

```
<160> NUMBER OF SEQ ID NOS: 40

<210> SEQ ID NO 1
<211> LENGTH: 5
<212> TYPE: PRT
<213> ORGANISM: Mus musculus

<400> SEQUENCE: 1

Thr Tyr Trp Met Asn
1               5

<210> SEQ ID NO 2
<211> LENGTH: 17
<212> TYPE: PRT
<213> ORGANISM: Mus musculus

<400> SEQUENCE: 2

Met Ile His Pro Ser Asp Ser Glu Thr Arg Leu Asn Gln Lys Phe Lys
1               5                   10                  15

Asp

<210> SEQ ID NO 3
<211> LENGTH: 11
<212> TYPE: PRT
<213> ORGANISM: Mus musculus

<400> SEQUENCE: 3

Ser Thr Met Ile Ala Thr Arg Ala Met Asp Tyr
1               5                   10

<210> SEQ ID NO 4
<211> LENGTH: 11
<212> TYPE: PRT
<213> ORGANISM: Mus musculus

<400> SEQUENCE: 4

Lys Ala Ser Gln Asp Val Ile Thr Gly Val Ala
1               5                   10
```

```
<210> SEQ ID NO 5
<211> LENGTH: 7
<212> TYPE: PRT
<213> ORGANISM: Mus musculus

<400> SEQUENCE: 5

Ser Ala Ser Tyr Arg Tyr Thr
1               5

<210> SEQ ID NO 6
<211> LENGTH: 9
<212> TYPE: PRT
<213> ORGANISM: Mus musculus

<400> SEQUENCE: 6

Gln Gln His Tyr Ser Thr Pro Leu Thr
1               5

<210> SEQ ID NO 7
<211> LENGTH: 5
<212> TYPE: PRT
<213> ORGANISM: Mus musculus

<400> SEQUENCE: 7

Arg Tyr Trp Met Ser
1               5

<210> SEQ ID NO 8
<211> LENGTH: 17
<212> TYPE: PRT
<213> ORGANISM: Mus musculus

<400> SEQUENCE: 8

Glu Ile Asn Pro Asp Ser Ser Thr Ile Asn Tyr Ala Pro Ser Leu Lys
1               5                   10                  15

Asp

<210> SEQ ID NO 9
<211> LENGTH: 10
<212> TYPE: PRT
<213> ORGANISM: Mus musculus

<400> SEQUENCE: 9

Pro Asp Gly Asn Tyr Trp Tyr Phe Asp Val
1               5                   10

<210> SEQ ID NO 10
<211> LENGTH: 11
<212> TYPE: PRT
<213> ORGANISM: Mus musculus

<400> SEQUENCE: 10

Lys Ala Ser Gln Asp Val Gly Ile Ala Val Ala
1               5                   10

<210> SEQ ID NO 11
<211> LENGTH: 7
<212> TYPE: PRT
<213> ORGANISM: Mus musculus

<400> SEQUENCE: 11

Trp Ala Ser Thr Arg His Thr
1               5
```

<210> SEQ ID NO 12
<211> LENGTH: 9
<212> TYPE: PRT
<213> ORGANISM: Mus musculus

<400> SEQUENCE: 12

Gln Gln Tyr Ser Ser Tyr Pro Tyr Thr
1               5

<210> SEQ ID NO 13
<211> LENGTH: 120
<212> TYPE: PRT
<213> ORGANISM: Mus musculus

<400> SEQUENCE: 13

Gln Val Gln Leu Gln Gln Pro Gly Ala Glu Leu Val Arg Pro Gly Ala
1               5                   10                  15

Ser Val Lys Leu Ser Cys Lys Ala Ser Gly Tyr Ser Phe Thr Thr Tyr
                20                  25                  30

Trp Met Asn Trp Val Lys Gln Arg Pro Gly Gln Gly Leu Glu Trp Ile
            35                  40                  45

Gly Met Ile His Pro Ser Asp Ser Glu Thr Arg Leu Asn Gln Lys Phe
    50                  55                  60

Lys Asp Lys Ala Thr Leu Thr Val Asp Lys Ser Ser Ser Thr Ala Tyr
65                  70                  75                  80

Met Gln Leu Ser Ser Pro Thr Ser Glu Asp Ser Ala Val Tyr Tyr Cys
                85                  90                  95

Ala Arg Ser Thr Met Ile Ala Thr Arg Ala Met Asp Tyr Trp Gly Gln
            100                 105                 110

Gly Thr Ser Val Thr Val Ser Ser
        115                 120

<210> SEQ ID NO 14
<211> LENGTH: 107
<212> TYPE: PRT
<213> ORGANISM: Mus musculus

<400> SEQUENCE: 14

Asp Ile Val Met Thr Gln Ser Gln Lys Ser Met Ser Thr Ser Val Gly
1               5                   10                  15

Asp Arg Val Ser Ile Thr Cys Lys Ala Ser Gln Asp Val Ile Thr Gly
                20                  25                  30

Val Ala Trp Tyr Gln Gln Lys Pro Gly Gln Ser Pro Lys Leu Leu Ile
            35                  40                  45

Tyr Ser Ala Ser Tyr Arg Tyr Thr Gly Val Pro Asp Arg Phe Thr Gly
    50                  55                  60

Ser Gly Ser Gly Thr Asp Phe Thr Phe Thr Ile Ser Asn Val Gln Ala
65                  70                  75                  80

Glu Asp Leu Ala Val Tyr Tyr Cys Gln Gln His Tyr Ser Thr Pro Leu
                85                  90                  95

Thr Phe Gly Ala Gly Thr Lys Leu Glu Leu Lys
            100                 105

<210> SEQ ID NO 15
<211> LENGTH: 119
<212> TYPE: PRT
<213> ORGANISM: Artificial Sequence
<220> FEATURE:
<223> OTHER INFORMATION: Synthetic

<400> SEQUENCE: 15

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Asp Phe Ser Arg Tyr
            20                  25                  30

Trp Met Ser Trp Val Arg Gln Ala Pro Gly Lys Gly Leu Glu Trp Ile
        35                  40                  45

Gly Glu Ile Asn Pro Asp Ser Ser Thr Ile Asn Tyr Ala Pro Ser Leu
    50                  55                  60

Lys Asp Lys Phe Ile Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Pro Asp Gly Asn Tyr Trp Tyr Phe Asp Val Trp Gly Gln Gly
            100                 105                 110

Thr Leu Val Thr Val Ser Ser
            115

<210> SEQ ID NO 16
<211> LENGTH: 107
<212> TYPE: PRT
<213> ORGANISM: Artificial Sequence
<220> FEATURE:
<223> OTHER INFORMATION: Synthetic

<400> SEQUENCE: 16

Asp Ile Gln Met Thr Gln Ser Pro Ser Ser Leu Ser Ala Ser Val Gly
1               5                   10                  15

Asp Arg Val Thr Ile Thr Cys Lys Ala Ser Gln Asp Val Gly Ile Ala
            20                  25                  30

Val Ala Trp Tyr Gln Gln Lys Pro Gly Lys Val Pro Lys Leu Leu Ile
        35                  40                  45

Tyr Trp Ala Ser Thr Arg His Thr Gly Val Pro Asp Arg Phe Ser Gly
    50                  55                  60

Ser Gly Ser Gly Thr Asp Phe Thr Leu Thr Ile Ser Ser Leu Gln Pro
65                  70                  75                  80

Glu Asp Val Ala Thr Tyr Tyr Cys Gln Gln Tyr Ser Ser Tyr Pro Tyr
                85                  90                  95

Thr Phe Gly Gln Gly Thr Lys Val Glu Ile Lys
            100                 105

<210> SEQ ID NO 17
<211> LENGTH: 18
<212> TYPE: PRT
<213> ORGANISM: Artificial Sequence
<220> FEATURE:
<223> OTHER INFORMATION: Synthetic

<400> SEQUENCE: 17

Gly Ser Thr Ser Gly Ser Gly Lys Pro Gly Ser Gly Glu Gly Ser Thr
1               5                   10                  15

Lys Gly

<210> SEQ ID NO 18
<211> LENGTH: 83
<212> TYPE: PRT
<213> ORGANISM: Homo sapiens

<400> SEQUENCE: 18

Phe Val Pro Val Phe Leu Pro Ala Lys Pro Thr Thr Thr Pro Ala Pro
1               5                   10                  15

Arg Pro Pro Thr Pro Ala Pro Thr Ile Ala Ser Gln Pro Leu Ser Leu
            20                  25                  30

Arg Pro Glu Ala Cys Arg Pro Ala Ala Gly Gly Ala Val His Thr Arg
        35                  40                  45

Gly Leu Asp Phe Ala Cys Asp Ile Tyr Ile Trp Ala Pro Leu Ala Gly
    50                  55                  60

Thr Cys Gly Val Leu Leu Leu Ser Leu Val Ile Thr Leu Tyr Cys Asn
65                  70                  75                  80

His Arg Asn

<210> SEQ ID NO 19
<211> LENGTH: 41
<212> TYPE: PRT
<213> ORGANISM: Homo sapiens

<400> SEQUENCE: 19

Arg Ser Lys Arg Ser Arg Leu Leu His Ser Asp Tyr Met Asn Met Thr
1               5                   10                  15

Pro Arg Arg Pro Gly Pro Thr Arg Lys His Tyr Gln Pro Tyr Ala Pro
            20                  25                  30

Pro Arg Asp Phe Ala Ala Tyr Arg Ser
        35                  40

<210> SEQ ID NO 20
<211> LENGTH: 112
<212> TYPE: PRT
<213> ORGANISM: Homo sapiens

<400> SEQUENCE: 20

Arg Val Lys Phe Ser Arg Ser Ala Asp Ala Pro Ala Tyr Gln Gln Gly
1               5                   10                  15

Gln Asn Gln Leu Tyr Asn Glu Leu Asn Leu Gly Arg Arg Glu Glu Tyr
            20                  25                  30

Asp Val Leu Asp Lys Arg Arg Gly Arg Asp Pro Glu Met Gly Gly Lys
        35                  40                  45

Pro Arg Arg Lys Asn Pro Gln Glu Gly Leu Tyr Asn Glu Leu Gln Lys
    50                  55                  60

Asp Lys Met Ala Glu Ala Tyr Ser Glu Ile Gly Met Lys Gly Glu Arg
65                  70                  75                  80

Arg Arg Gly Lys Gly His Asp Gly Leu Tyr Gln Gly Leu Ser Thr Ala
                85                  90                  95

Thr Lys Asp Thr Tyr Asp Ala Leu His Met Gln Ala Leu Pro Pro Arg
            100                 105                 110

<210> SEQ ID NO 21
<211> LENGTH: 42
<212> TYPE: PRT
<213> ORGANISM: Homo sapiens

<400> SEQUENCE: 21

Lys Arg Gly Arg Lys Lys Leu Leu Tyr Ile Phe Lys Gln Pro Phe Met
1               5                   10                  15

Arg Pro Val Gln Thr Thr Gln Glu Glu Asp Gly Cys Ser Cys Arg Phe
            20                  25                  30

```
Pro Glu Glu Glu Gly Gly Cys Glu Leu
        35                  40
```

```
<210> SEQ ID NO 22
<211> LENGTH: 21
<212> TYPE: PRT
<213> ORGANISM: Homo sapiens

<400> SEQUENCE: 22

Met Ala Leu Pro Val Thr Ala Leu Leu Leu Pro Leu Ala Leu Leu Leu
1               5                   10                  15

His Ala Ala Arg Pro
            20

<210> SEQ ID NO 23
<211> LENGTH: 22
<212> TYPE: PRT
<213> ORGANISM: Thosea asigna virus 2A

<400> SEQUENCE: 23

Ala Ser Arg Ala Glu Gly Arg Gly Ser Leu Leu Thr Cys Gly Asp Val
1               5                   10                  15

Glu Glu Asn Pro Gly Pro
            20

<210> SEQ ID NO 24
<211> LENGTH: 110
<212> TYPE: PRT
<213> ORGANISM: Artificial Sequence
<220> FEATURE:
<223> OTHER INFORMATION: Synthetic

<400> SEQUENCE: 24

Met Val Glu Gly Val Gln Val Glu Thr Ile Ser Pro Gly Asp Gly Arg
1               5                   10                  15

Thr Phe Pro Lys Arg Gly Gln Thr Cys Val Val His Tyr Thr Gly Met
            20                  25                  30

Leu Glu Asp Gly Lys Lys Val Asp Ser Ser Arg Asp Arg Asn Lys Pro
        35                  40                  45

Phe Lys Phe Met Leu Gly Lys Gln Glu Val Ile Arg Gly Trp Glu Glu
    50                  55                  60

Gly Val Ala Gln Met Ser Val Gly Gln Arg Ala Lys Leu Thr Ile Ser
65                  70                  75                  80

Pro Asp Tyr Ala Tyr Gly Ala Thr Gly His Pro Gly Ile Ile Pro Pro
                85                  90                  95

His Ala Thr Leu Val Phe Asp Val Glu Leu Leu Lys Leu Glu
            100                 105                 110

<210> SEQ ID NO 25
<211> LENGTH: 285
<212> TYPE: PRT
<213> ORGANISM: Artificial Sequence
<220> FEATURE:
<223> OTHER INFORMATION: Synthetic

<400> SEQUENCE: 25

Gly Val Asp Gly Phe Gly Asp Val Gly Ala Leu Glu Ser Leu Arg Gly
1               5                   10                  15

Asn Ala Asp Leu Ala Tyr Ile Leu Ser Met Glu Pro Cys Gly His Cys
            20                  25                  30

Leu Ile Ile Asn Asn Val Asn Phe Cys Arg Glu Ser Gly Leu Arg Thr
```

```
                35                  40                  45
Arg Thr Gly Ser Asn Ile Asp Cys Glu Lys Leu Arg Arg Phe Ser
    50                  55                  60

Ser Leu His Phe Met Val Glu Val Lys Gly Asp Leu Thr Ala Lys Lys
65                  70                  75                  80

Met Val Leu Ala Leu Leu Glu Leu Ala Gln Gln Asp His Gly Ala Leu
                85                  90                  95

Asp Cys Cys Val Val Val Ile Leu Ser His Gly Cys Gln Ala Ser His
                100                 105                 110

Leu Gln Phe Pro Gly Ala Val Tyr Gly Thr Asp Gly Cys Pro Val Ser
            115                 120                 125

Val Glu Lys Ile Val Asn Ile Phe Asn Gly Thr Ser Cys Pro Ser Leu
        130                 135                 140

Gly Gly Lys Pro Lys Leu Phe Phe Ile Gln Ala Cys Gly Gly Glu Gln
145                 150                 155                 160

Lys Asp His Gly Phe Glu Val Ala Ser Thr Ser Pro Glu Asp Glu Ser
                165                 170                 175

Pro Gly Ser Asn Pro Glu Pro Asp Ala Thr Pro Phe Gln Glu Gly Leu
            180                 185                 190

Arg Thr Phe Asp Gln Leu Asp Ala Ile Ser Ser Leu Pro Thr Pro Ser
        195                 200                 205

Asp Ile Phe Val Ser Tyr Ser Thr Phe Pro Gly Phe Val Ser Trp Arg
210                 215                 220

Asp Pro Lys Ser Gly Ser Trp Tyr Val Glu Thr Leu Asp Asp Ile Phe
225                 230                 235                 240

Glu Gln Trp Ala His Ser Glu Asp Leu Gln Ser Leu Leu Arg Val
                245                 250                 255

Ala Asn Ala Val Ser Val Lys Gly Ile Tyr Lys Gln Met Pro Gly Cys
            260                 265                 270

Phe Asn Phe Leu Arg Lys Lys Leu Phe Phe Lys Thr Ser
        275                 280                 285

<210> SEQ ID NO 26
<211> LENGTH: 5
<212> TYPE: PRT
<213> ORGANISM: Artificial Sequence
<220> FEATURE:
<223> OTHER INFORMATION: Synthetic

<400> SEQUENCE: 26

Ser Gly Gly Gly Ser
1               5

<210> SEQ ID NO 27
<211> LENGTH: 502
<212> TYPE: PRT
<213> ORGANISM: Artificial Sequence
<220> FEATURE:
<223> OTHER INFORMATION: Synthetic

<400> SEQUENCE: 27

Met Ala Leu Pro Val Thr Ala Leu Leu Leu Pro Leu Ala Leu Leu Leu
1               5                   10                  15

His Ala Ala Arg Pro Asp Ile Val Met Thr Gln Ser Gln Lys Ser Met
                20                  25                  30

Ser Thr Ser Val Gly Asp Arg Val Ser Ile Thr Cys Lys Ala Ser Gln
            35                  40                  45
```

-continued

Asp Val Ile Thr Gly Val Ala Trp Tyr Gln Gln Lys Pro Gly Gln Ser
50                  55                  60

Pro Lys Leu Leu Ile Tyr Ser Ala Ser Tyr Arg Tyr Thr Gly Val Pro
65                  70                  75                  80

Asp Arg Phe Thr Gly Ser Gly Ser Gly Thr Asp Phe Thr Phe Thr Ile
                85                  90                  95

Ser Asn Val Gln Ala Glu Asp Leu Ala Val Tyr Tyr Cys Gln Gln His
                100                 105                 110

Tyr Ser Thr Pro Leu Thr Phe Gly Ala Gly Thr Lys Leu Glu Leu Lys
                115                 120                 125

Gly Ser Thr Ser Gly Ser Gly Lys Pro Gly Ser Gly Glu Gly Ser Thr
130                 135                 140

Lys Gly Gln Val Gln Leu Gln Gln Pro Gly Ala Glu Leu Val Arg Pro
145                 150                 155                 160

Gly Ala Ser Val Lys Leu Ser Cys Lys Ala Ser Gly Tyr Ser Phe Thr
                165                 170                 175

Thr Tyr Trp Met Asn Trp Val Lys Gln Arg Pro Gly Gln Gly Leu Glu
                180                 185                 190

Trp Ile Gly Met Ile His Pro Ser Asp Ser Glu Thr Arg Leu Asn Gln
                195                 200                 205

Lys Phe Lys Asp Lys Ala Thr Leu Thr Val Asp Lys Ser Ser Ser Thr
210                 215                 220

Ala Tyr Met Gln Leu Ser Ser Pro Thr Ser Glu Asp Ser Ala Val Tyr
225                 230                 235                 240

Tyr Cys Ala Arg Ser Thr Met Ile Ala Thr Arg Ala Met Asp Tyr Trp
                245                 250                 255

Gly Gln Gly Thr Ser Val Thr Val Ser Ser Phe Val Pro Val Phe Leu
                260                 265                 270

Pro Ala Lys Pro Thr Thr Thr Pro Ala Pro Arg Pro Pro Thr Pro Ala
                275                 280                 285

Pro Thr Ile Ala Ser Gln Pro Leu Ser Leu Arg Pro Glu Ala Cys Arg
                290                 295                 300

Pro Ala Ala Gly Gly Ala Val His Thr Arg Gly Leu Asp Phe Ala Cys
305                 310                 315                 320

Asp Ile Tyr Ile Trp Ala Pro Leu Ala Gly Thr Cys Gly Val Leu Leu
                325                 330                 335

Leu Ser Leu Val Ile Thr Leu Tyr Cys Asn His Arg Asn Arg Ser Lys
                340                 345                 350

Arg Ser Arg Leu Leu His Ser Asp Tyr Met Asn Met Thr Pro Arg Arg
                355                 360                 365

Pro Gly Pro Thr Arg Lys His Tyr Gln Pro Tyr Ala Pro Pro Arg Asp
                370                 375                 380

Phe Ala Ala Tyr Arg Ser Arg Val Lys Phe Ser Arg Ser Ala Asp Ala
385                 390                 395                 400

Pro Ala Tyr Gln Gln Gly Gln Asn Gln Leu Tyr Asn Glu Leu Asn Leu
                405                 410                 415

Gly Arg Arg Glu Glu Tyr Asp Val Leu Asp Lys Arg Gly Arg Asp
                420                 425                 430

Pro Glu Met Gly Gly Lys Pro Arg Arg Lys Asn Pro Gln Glu Gly Leu
                435                 440                 445

Tyr Asn Glu Leu Gln Lys Asp Lys Met Ala Glu Ala Tyr Ser Glu Ile
450                 455                 460

Gly Met Lys Gly Glu Arg Arg Arg Gly Lys Gly His Asp Gly Leu Tyr

```
            465                 470                 475                 480
Gln Gly Leu Ser Thr Ala Thr Lys Asp Thr Tyr Asp Ala Leu His Met
                485                 490                 495

Gln Ala Leu Pro Pro Arg
                500

<210> SEQ ID NO 28
<211> LENGTH: 501
<212> TYPE: PRT
<213> ORGANISM: Artificial Sequence
<220> FEATURE:
<223> OTHER INFORMATION: Synthetic

<400> SEQUENCE: 28

Met Ala Leu Pro Val Thr Ala Leu Leu Leu Pro Leu Ala Leu Leu Leu
1               5                   10                  15

His Ala Ala Arg Pro Asp Ile Gln Met Thr Gln Ser Pro Ser Ser Leu
                20                  25                  30

Ser Ala Ser Val Gly Asp Arg Val Thr Ile Thr Cys Lys Ala Ser Gln
            35                  40                  45

Asp Val Gly Ile Ala Val Ala Trp Tyr Gln Gln Lys Pro Gly Lys Val
    50                  55                  60

Pro Lys Leu Leu Ile Tyr Trp Ala Ser Thr Arg His Thr Gly Val Pro
65                  70                  75                  80

Asp Arg Phe Ser Gly Ser Gly Ser Gly Thr Asp Phe Thr Leu Thr Ile
                85                  90                  95

Ser Ser Leu Gln Pro Glu Asp Val Ala Thr Tyr Tyr Cys Gln Gln Tyr
            100                 105                 110

Ser Ser Tyr Pro Tyr Thr Phe Gly Gln Gly Thr Lys Val Glu Ile Lys
        115                 120                 125

Gly Ser Thr Ser Gly Ser Gly Lys Pro Gly Ser Gly Glu Gly Ser Thr
    130                 135                 140

Lys Gly Glu Val Gln Leu Val Glu Ser Gly Gly Gly Leu Val Gln Pro
145                 150                 155                 160

Gly Gly Ser Leu Arg Leu Ser Cys Ala Ala Ser Gly Phe Asp Phe Ser
                165                 170                 175

Arg Tyr Trp Met Ser Trp Val Arg Gln Ala Pro Gly Lys Gly Leu Glu
            180                 185                 190

Trp Ile Gly Glu Ile Asn Pro Asp Ser Ser Thr Ile Asn Tyr Ala Pro
        195                 200                 205

Ser Leu Lys Asp Lys Phe Ile Ile Ser Arg Asp Asn Ala Lys Asn Ser
    210                 215                 220

Leu Tyr Leu Gln Met Asn Ser Leu Arg Ala Glu Asp Thr Ala Val Tyr
225                 230                 235                 240

Tyr Cys Ala Arg Pro Asp Gly Asn Tyr Trp Tyr Phe Asp Val Trp Gly
                245                 250                 255

Gln Gly Thr Leu Val Thr Val Ser Phe Val Pro Val Phe Leu Pro
            260                 265                 270

Ala Lys Pro Thr Thr Thr Pro Ala Pro Arg Pro Pro Thr Pro Ala Pro
        275                 280                 285

Thr Ile Ala Ser Gln Pro Leu Ser Leu Arg Pro Glu Ala Cys Arg Pro
    290                 295                 300

Ala Ala Gly Gly Ala Val His Thr Arg Gly Leu Asp Phe Ala Cys Asp
305                 310                 315                 320

Ile Tyr Ile Trp Ala Pro Leu Ala Gly Thr Cys Gly Val Leu Leu Leu
```

```
            325                 330                 335
Ser Leu Val Ile Thr Leu Tyr Cys Asn His Arg Asn Arg Ser Lys Arg
        340                 345                 350

Ser Arg Leu Leu His Ser Asp Tyr Met Asn Met Thr Pro Arg Arg Pro
    355                 360                 365

Gly Pro Thr Arg Lys His Tyr Gln Pro Tyr Ala Pro Pro Arg Asp Phe
370                 375                 380

Ala Ala Tyr Arg Ser Arg Val Lys Phe Ser Arg Ser Ala Asp Ala Pro
385                 390                 395                 400

Ala Tyr Gln Gln Gly Gln Asn Gln Leu Tyr Asn Glu Leu Asn Leu Gly
                405                 410                 415

Arg Arg Glu Glu Tyr Asp Val Leu Asp Lys Arg Arg Gly Arg Asp Pro
            420                 425                 430

Glu Met Gly Gly Lys Pro Arg Arg Lys Asn Pro Gln Glu Gly Leu Tyr
        435                 440                 445

Asn Glu Leu Gln Lys Asp Lys Met Ala Glu Ala Tyr Ser Glu Ile Gly
    450                 455                 460

Met Lys Gly Glu Arg Arg Arg Gly Lys Gly His Asp Gly Leu Tyr Gln
465                 470                 475                 480

Gly Leu Ser Thr Ala Thr Lys Asp Thr Tyr Asp Ala Leu His Met Gln
                485                 490                 495

Ala Leu Pro Pro Arg
            500

<210> SEQ ID NO 29
<211> LENGTH: 503
<212> TYPE: PRT
<213> ORGANISM: Artificial Sequence
<220> FEATURE:
<223> OTHER INFORMATION: Synthetic

<400> SEQUENCE: 29

Met Ala Leu Pro Val Thr Ala Leu Leu Leu Pro Leu Ala Leu Leu Leu
1               5                   10                  15

His Ala Ala Arg Pro Asp Ile Val Met Thr Gln Ser Gln Lys Ser Met
            20                  25                  30

Ser Thr Ser Val Gly Asp Arg Val Ser Ile Thr Cys Lys Ala Ser Gln
        35                  40                  45

Asp Val Ile Thr Gly Val Ala Trp Tyr Gln Gln Lys Pro Gly Gln Ser
    50                  55                  60

Pro Lys Leu Leu Ile Tyr Ser Ala Ser Tyr Arg Tyr Thr Gly Val Pro
65                  70                  75                  80

Asp Arg Phe Thr Gly Ser Gly Ser Gly Thr Asp Phe Thr Phe Thr Ile
                85                  90                  95

Ser Asn Val Gln Ala Glu Asp Leu Ala Val Tyr Tyr Cys Gln Gln His
            100                 105                 110

Tyr Ser Thr Pro Leu Thr Phe Gly Ala Gly Thr Lys Leu Glu Leu Lys
        115                 120                 125

Gly Ser Thr Ser Gly Ser Gly Lys Pro Gly Ser Gly Glu Gly Ser Thr
    130                 135                 140

Lys Gly Gln Val Gln Leu Gln Gln Pro Gly Ala Glu Leu Val Arg Pro
145                 150                 155                 160

Gly Ala Ser Val Lys Leu Ser Cys Lys Ala Ser Gly Tyr Ser Phe Thr
                165                 170                 175

Thr Tyr Trp Met Asn Trp Val Lys Gln Arg Pro Gly Gln Gly Leu Glu
```

```
            180                 185                 190
Trp Ile Gly Met Ile His Pro Ser Asp Ser Glu Thr Arg Leu Asn Gln
            195                 200                 205

Lys Phe Lys Asp Lys Ala Thr Leu Thr Val Asp Lys Ser Ser Ser Thr
        210                 215                 220

Ala Tyr Met Gln Leu Ser Ser Pro Thr Ser Glu Asp Ser Ala Val Tyr
225                 230                 235                 240

Tyr Cys Ala Arg Ser Thr Met Ile Ala Thr Arg Ala Met Asp Tyr Trp
                245                 250                 255

Gly Gln Gly Thr Ser Val Thr Val Ser Ser Phe Val Pro Val Phe Leu
            260                 265                 270

Pro Ala Lys Pro Thr Thr Thr Pro Ala Pro Arg Pro Pro Thr Pro Ala
        275                 280                 285

Pro Thr Ile Ala Ser Gln Pro Leu Ser Leu Arg Pro Glu Ala Cys Arg
    290                 295                 300

Pro Ala Ala Gly Gly Ala Val His Thr Arg Gly Leu Asp Phe Ala Cys
305                 310                 315                 320

Asp Ile Tyr Ile Trp Ala Pro Leu Ala Gly Thr Cys Gly Val Leu Leu
                325                 330                 335

Leu Ser Leu Val Ile Thr Leu Tyr Cys Asn His Arg Asn Lys Arg Gly
            340                 345                 350

Arg Lys Lys Leu Leu Tyr Ile Phe Lys Gln Pro Phe Met Arg Pro Val
        355                 360                 365

Gln Thr Thr Gln Glu Glu Asp Gly Cys Ser Cys Arg Phe Pro Glu Glu
    370                 375                 380

Glu Glu Gly Gly Cys Glu Leu Arg Val Lys Phe Ser Arg Ser Ala Asp
385                 390                 395                 400

Ala Pro Ala Tyr Gln Gln Gly Gln Asn Gln Leu Tyr Asn Glu Leu Asn
                405                 410                 415

Leu Gly Arg Arg Glu Glu Tyr Asp Val Leu Asp Lys Arg Arg Gly Arg
            420                 425                 430

Asp Pro Glu Met Gly Gly Lys Pro Arg Arg Lys Asn Pro Gln Glu Gly
        435                 440                 445

Leu Tyr Asn Glu Leu Gln Lys Asp Lys Met Ala Glu Ala Tyr Ser Glu
    450                 455                 460

Ile Gly Met Lys Gly Glu Arg Arg Arg Gly Lys Gly His Asp Gly Leu
465                 470                 475                 480

Tyr Gln Gly Leu Ser Thr Ala Thr Lys Asp Thr Tyr Asp Ala Leu His
                485                 490                 495

Met Gln Ala Leu Pro Pro Arg
            500

<210> SEQ ID NO 30
<211> LENGTH: 922
<212> TYPE: PRT
<213> ORGANISM: Artificial Sequence
<220> FEATURE:
<223> OTHER INFORMATION: Synthetic

<400> SEQUENCE: 30

Met Ala Leu Pro Val Thr Ala Leu Leu Leu Pro Leu Ala Leu Leu Leu
1               5                   10                  15

His Ala Ala Arg Pro Asp Ile Val Met Thr Gln Ser Gln Lys Ser Met
            20                  25                  30

Ser Thr Ser Val Gly Asp Arg Val Ser Ile Thr Cys Lys Ala Ser Gln
```

```
            35                  40                  45
Asp Val Ile Thr Gly Val Ala Trp Tyr Gln Gln Lys Pro Gly Gln Ser
 50                  55                  60

Pro Lys Leu Leu Ile Tyr Ser Ala Ser Tyr Arg Tyr Thr Gly Val Pro
 65                  70                  75                  80

Asp Arg Phe Thr Gly Ser Gly Ser Gly Thr Asp Phe Thr Phe Thr Ile
                     85                  90                  95

Ser Asn Val Gln Ala Glu Asp Leu Ala Val Tyr Tyr Cys Gln Gln His
                    100                 105                 110

Tyr Ser Thr Pro Leu Thr Phe Gly Ala Gly Thr Lys Leu Glu Leu Lys
                115                 120                 125

Gly Ser Thr Gly Ser Gly Lys Pro Gly Ser Gly Glu Gly Ser Thr
                130                 135                 140

Lys Gly Gln Val Gln Leu Gln Gln Pro Gly Ala Glu Leu Val Arg Pro
145                 150                 155                 160

Gly Ala Ser Val Lys Leu Ser Cys Lys Ala Ser Gly Tyr Ser Phe Thr
                    165                 170                 175

Thr Tyr Trp Met Asn Trp Val Lys Gln Arg Pro Gly Gln Gly Leu Glu
                180                 185                 190

Trp Ile Gly Met Ile His Pro Ser Asp Ser Glu Thr Arg Leu Asn Gln
                195                 200                 205

Lys Phe Lys Asp Lys Ala Thr Leu Thr Val Asp Lys Ser Ser Ser Thr
210                 215                 220

Ala Tyr Met Gln Leu Ser Ser Pro Thr Ser Glu Asp Ser Ala Val Tyr
225                 230                 235                 240

Tyr Cys Ala Arg Ser Thr Met Ile Ala Thr Arg Ala Met Asp Tyr Trp
                245                 250                 255

Gly Gln Gly Thr Ser Val Thr Val Ser Ser Phe Val Pro Val Phe Leu
                260                 265                 270

Pro Ala Lys Pro Thr Thr Thr Pro Ala Pro Arg Pro Pro Thr Pro Ala
                275                 280                 285

Pro Thr Ile Ala Ser Gln Pro Leu Ser Leu Arg Pro Glu Ala Cys Arg
290                 295                 300

Pro Ala Ala Gly Gly Ala Val His Thr Arg Gly Leu Asp Phe Ala Cys
305                 310                 315                 320

Asp Ile Tyr Ile Trp Ala Pro Leu Ala Gly Thr Cys Gly Val Leu Leu
                325                 330                 335

Leu Ser Leu Val Ile Thr Leu Tyr Cys Asn His Arg Asn Arg Ser Lys
                340                 345                 350

Arg Ser Arg Leu Leu His Ser Asp Tyr Met Asn Met Thr Pro Arg Arg
                355                 360                 365

Pro Gly Pro Thr Arg Lys His Tyr Gln Pro Tyr Ala Pro Pro Arg Asp
                370                 375                 380

Phe Ala Ala Tyr Arg Ser Arg Val Lys Phe Ser Arg Ser Ala Asp Ala
385                 390                 395                 400

Pro Ala Tyr Gln Gln Gly Gln Asn Gln Leu Tyr Asn Glu Leu Asn Leu
                    405                 410                 415

Gly Arg Arg Glu Glu Tyr Asp Val Leu Asp Lys Arg Arg Gly Arg Asp
                420                 425                 430

Pro Glu Met Gly Gly Lys Pro Arg Arg Lys Asn Pro Gln Glu Gly Leu
                435                 440                 445

Tyr Asn Glu Leu Gln Lys Asp Lys Met Ala Glu Ala Tyr Ser Glu Ile
                450                 455                 460
```

```
Gly Met Lys Gly Glu Arg Arg Gly Lys Gly His Asp Gly Leu Tyr
465                 470                 475                 480

Gln Gly Leu Ser Thr Ala Thr Lys Asp Thr Tyr Asp Ala Leu His Met
                485                 490                 495

Gln Ala Leu Pro Pro Arg Arg Ala Glu Gly Arg Gly Ser Leu Leu Thr
            500                 505                 510

Cys Gly Asp Val Glu Glu Asn Pro Gly Pro Met Leu Glu Gly Val Gln
        515                 520                 525

Val Glu Thr Ile Ser Pro Gly Asp Gly Arg Thr Phe Pro Lys Arg Gly
530                 535                 540

Gln Thr Cys Val Val His Tyr Thr Gly Met Leu Glu Asp Gly Lys Lys
545                 550                 555                 560

Val Asp Ser Ser Arg Asp Arg Asn Lys Pro Phe Lys Phe Met Leu Gly
                565                 570                 575

Lys Gln Glu Val Ile Arg Gly Trp Glu Glu Gly Val Ala Gln Met Ser
            580                 585                 590

Val Gly Gln Arg Ala Lys Leu Thr Ile Ser Pro Asp Tyr Ala Tyr Gly
        595                 600                 605

Ala Thr Gly His Pro Gly Ile Ile Pro Pro His Ala Thr Leu Val Phe
610                 615                 620

Asp Val Glu Leu Leu Lys Leu Glu Ser Gly Gly Ser Gly Val Asp
625                 630                 635                 640

Gly Phe Gly Asp Val Gly Ala Leu Glu Ser Leu Arg Gly Asn Ala Asp
                645                 650                 655

Leu Ala Tyr Ile Leu Ser Met Glu Pro Cys Gly His Cys Leu Ile Ile
            660                 665                 670

Asn Asn Val Asn Phe Cys Arg Glu Ser Gly Leu Arg Thr Arg Thr Gly
        675                 680                 685

Ser Asn Ile Asp Cys Glu Lys Leu Arg Arg Arg Phe Ser Ser Leu His
690                 695                 700

Phe Met Val Glu Val Lys Gly Asp Leu Thr Ala Lys Lys Met Val Leu
705                 710                 715                 720

Ala Leu Leu Glu Leu Ala Gln Gln Asp His Gly Ala Leu Asp Cys Cys
                725                 730                 735

Val Val Val Ile Leu Ser His Gly Cys Gln Ala Ser His Leu Gln Phe
            740                 745                 750

Pro Gly Ala Val Tyr Gly Thr Asp Gly Cys Pro Val Ser Val Glu Lys
        755                 760                 765

Ile Val Asn Ile Phe Asn Gly Thr Ser Cys Pro Ser Leu Gly Gly Lys
770                 775                 780

Pro Lys Leu Phe Phe Ile Gln Ala Cys Gly Gly Glu Gln Lys Asp His
785                 790                 795                 800

Gly Phe Glu Val Ala Ser Thr Ser Pro Glu Asp Glu Ser Pro Gly Ser
                805                 810                 815

Asn Pro Glu Pro Asp Ala Thr Pro Phe Gln Glu Gly Leu Arg Thr Phe
            820                 825                 830

Asp Gln Leu Asp Ala Ile Ser Ser Leu Pro Thr Pro Ser Asp Ile Phe
        835                 840                 845

Val Ser Tyr Ser Thr Phe Pro Gly Phe Val Ser Trp Arg Asp Pro Lys
850                 855                 860

Ser Gly Ser Trp Tyr Val Glu Thr Leu Asp Asp Ile Phe Glu Gln Trp
865                 870                 875                 880
```

```
Ala His Ser Glu Asp Leu Gln Ser Leu Leu Arg Val Ala Asn Ala
            885                 890                 895

Val Ser Val Lys Gly Ile Tyr Lys Gln Met Pro Gly Cys Phe Asn Phe
        900                 905                 910

Leu Arg Lys Lys Leu Phe Phe Lys Thr Ser
        915                 920

<210> SEQ ID NO 31
<211> LENGTH: 924
<212> TYPE: PRT
<213> ORGANISM: Artificial Sequence
<220> FEATURE:
<223> OTHER INFORMATION: Synthetic

<400> SEQUENCE: 31

Met Val Glu Gly Val Gln Val Glu Thr Ile Ser Pro Gly Asp Gly Arg
1               5                   10                  15

Thr Phe Pro Lys Arg Gly Gln Thr Cys Val Val His Tyr Thr Gly Met
            20                  25                  30

Leu Glu Asp Gly Lys Lys Val Asp Ser Ser Arg Asp Arg Asn Lys Pro
        35                  40                  45

Phe Lys Phe Met Leu Gly Lys Gln Glu Val Ile Arg Gly Trp Glu Glu
50                  55                  60

Gly Val Ala Gln Met Ser Val Gly Gln Arg Ala Lys Leu Thr Ile Ser
65                  70                  75                  80

Pro Asp Tyr Ala Tyr Gly Ala Thr Gly His Pro Gly Ile Ile Pro Pro
                85                  90                  95

His Ala Thr Leu Val Phe Asp Val Glu Leu Leu Lys Leu Glu Ser Gly
            100                 105                 110

Gly Gly Ser Gly Val Asp Gly Phe Gly Asp Val Gly Ala Leu Glu Ser
        115                 120                 125

Leu Arg Gly Asn Ala Asp Leu Ala Tyr Ile Leu Ser Met Glu Pro Cys
130                 135                 140

Gly His Cys Leu Ile Ile Asn Asn Val Asn Phe Cys Arg Glu Ser Gly
145                 150                 155                 160

Leu Arg Thr Arg Thr Gly Ser Asn Ile Asp Cys Glu Lys Leu Arg Arg
                165                 170                 175

Arg Phe Ser Ser Leu His Phe Met Val Glu Val Lys Gly Asp Leu Thr
            180                 185                 190

Ala Lys Lys Met Val Leu Ala Leu Leu Glu Leu Ala Gln Gln Asp His
        195                 200                 205

Gly Ala Leu Asp Cys Cys Val Val Val Ile Leu Ser His Gly Cys Gln
    210                 215                 220

Ala Ser His Leu Gln Phe Pro Gly Ala Val Tyr Gly Thr Asp Gly Cys
225                 230                 235                 240

Pro Val Ser Val Glu Lys Ile Val Asn Ile Phe Asn Gly Thr Ser Cys
                245                 250                 255

Pro Ser Leu Gly Gly Lys Pro Lys Leu Phe Phe Ile Gln Ala Cys Gly
            260                 265                 270

Gly Glu Gln Lys Asp His Gly Phe Glu Val Ala Ser Thr Ser Pro Glu
        275                 280                 285

Asp Glu Ser Pro Gly Ser Asn Pro Glu Pro Asp Ala Thr Pro Phe Gln
    290                 295                 300

Glu Gly Leu Arg Thr Phe Asp Gln Leu Asp Ala Ile Ser Ser Leu Pro
305                 310                 315                 320
```

-continued

```
Thr Pro Ser Asp Ile Phe Val Ser Tyr Ser Thr Phe Pro Gly Phe Val
            325                 330                 335

Ser Trp Arg Asp Pro Lys Ser Gly Ser Trp Tyr Val Glu Thr Leu Asp
340                 345                 350

Asp Ile Phe Glu Gln Trp Ala His Ser Glu Asp Leu Gln Ser Leu Leu
        355                 360                 365

Leu Arg Val Ala Asn Ala Val Ser Val Lys Gly Ile Tyr Lys Gln Met
370                 375                 380

Pro Gly Cys Phe Asn Phe Leu Arg Lys Lys Leu Phe Phe Lys Thr Ser
385                 390                 395                 400

Ala Ser Arg Ala Glu Gly Arg Gly Ser Leu Leu Thr Cys Gly Asp Val
                405                 410                 415

Glu Glu Asn Pro Gly Pro Met Ala Leu Pro Val Thr Ala Leu Leu Leu
            420                 425                 430

Pro Leu Ala Leu Leu Leu His Ala Ala Arg Pro Asp Ile Val Met Thr
            435                 440                 445

Gln Ser Gln Lys Ser Met Ser Thr Ser Val Gly Asp Arg Val Ser Ile
    450                 455                 460

Thr Cys Lys Ala Ser Gln Asp Val Ile Thr Gly Val Ala Trp Tyr Gln
465                 470                 475                 480

Gln Lys Pro Gly Gln Ser Pro Lys Leu Leu Ile Tyr Ser Ala Ser Tyr
                485                 490                 495

Arg Tyr Thr Gly Val Pro Asp Arg Phe Thr Gly Ser Gly Ser Gly Thr
            500                 505                 510

Asp Phe Thr Phe Thr Ile Ser Asn Val Gln Ala Glu Asp Leu Ala Val
        515                 520                 525

Tyr Tyr Cys Gln Gln His Tyr Ser Thr Pro Leu Thr Phe Gly Ala Gly
530                 535                 540

Thr Lys Leu Glu Leu Lys Gly Ser Thr Ser Gly Ser Gly Lys Pro Gly
545                 550                 555                 560

Ser Gly Glu Gly Ser Thr Lys Gly Gln Val Gln Leu Gln Gln Pro Gly
                565                 570                 575

Ala Glu Leu Val Arg Pro Gly Ala Ser Val Lys Leu Ser Cys Lys Ala
            580                 585                 590

Ser Gly Tyr Ser Phe Thr Thr Tyr Trp Met Asn Trp Val Lys Gln Arg
            595                 600                 605

Pro Gly Gln Gly Leu Glu Trp Ile Gly Met Ile His Pro Ser Asp Ser
            610                 615                 620

Glu Thr Arg Leu Asn Gln Lys Phe Lys Asp Lys Ala Thr Leu Thr Val
625                 630                 635                 640

Asp Lys Ser Ser Ser Thr Ala Tyr Met Gln Leu Ser Ser Pro Thr Ser
                645                 650                 655

Glu Asp Ser Ala Val Tyr Tyr Cys Ala Arg Ser Thr Met Ile Ala Thr
            660                 665                 670

Arg Ala Met Asp Tyr Trp Gly Gln Gly Thr Ser Val Thr Val Ser Ser
            675                 680                 685

Phe Val Pro Val Phe Leu Pro Ala Lys Pro Thr Thr Thr Pro Ala Pro
690                 695                 700

Arg Pro Pro Thr Pro Ala Pro Thr Ile Ala Ser Gln Pro Leu Ser Leu
705                 710                 715                 720

Arg Pro Glu Ala Cys Arg Pro Ala Ala Gly Gly Ala Val His Thr Arg
                725                 730                 735

Gly Leu Asp Phe Ala Cys Asp Ile Tyr Ile Trp Ala Pro Leu Ala Gly
```

```
                    740               745               750
Thr Cys Gly Val Leu Leu Leu Ser Leu Val Ile Thr Leu Tyr Cys Asn
            755                 760                 765
His Arg Asn Arg Ser Lys Arg Ser Arg Leu Leu His Ser Asp Tyr Met
770                 775                 780
Asn Met Thr Pro Arg Pro Gly Pro Thr Arg Lys His Tyr Gln Pro
785                 790                 795                 800
Tyr Ala Pro Pro Arg Asp Phe Ala Ala Tyr Arg Ser Arg Val Lys Phe
                805                 810                 815
Ser Arg Ser Ala Asp Ala Pro Ala Tyr Gln Gln Gly Gln Asn Gln Leu
            820                 825                 830
Tyr Asn Glu Leu Asn Leu Gly Arg Arg Glu Glu Tyr Asp Val Leu Asp
        835                 840                 845
Lys Arg Arg Gly Arg Asp Pro Glu Met Gly Gly Lys Pro Arg Arg Lys
    850                 855                 860
Asn Pro Gln Glu Gly Leu Tyr Asn Glu Leu Gln Lys Asp Lys Met Ala
865                 870                 875                 880
Glu Ala Tyr Ser Glu Ile Gly Met Lys Gly Glu Arg Arg Arg Gly Lys
                885                 890                 895
Gly His Asp Gly Leu Tyr Gln Gly Leu Ser Thr Ala Thr Lys Asp Thr
            900                 905                 910
Tyr Asp Ala Leu His Met Gln Ala Leu Pro Pro Arg
        915                 920
```

<210> SEQ ID NO 32
<211> LENGTH: 1509
<212> TYPE: DNA
<213> ORGANISM: Artificial Sequence
<220> FEATURE:
<223> OTHER INFORMATION: Synthetic

<400> SEQUENCE: 32

```
atggccctgc ctgttacagc tctgctgctg cctctggctc tgcttctgca tgccgccaga    60
cctgacatcg tgatgaccca gtctcagaaa tccatgagca ccagcgtggg cgacagagtg   120
tccatcacct gtaaagccag ccaggacgtg atcacaggcg tggcctggta tcagcagaag   180
cctggccagt ctcctaagct gctgatctac agcgccagct acagatacac cggcgtgccc   240
gatagattca caggcagcgg ctctggcacc gacttcacct tcaccatcag caacgtgcag   300
gccgaggatc tggccgtgta ctactgtcag cagcactaca gcacccctct gacctttggc   360
gccggaacaa agctggaact gaagggcagc acaagcggag cggaaaaacc tggatctggc   420
gagggctcta ccaaaggcca ggttcagctt cagcagcctg cgccgaact  tgttagacct   480
ggcgcctctg tgaagctgtc ctgcaaggcc agcggctact ccttcaccac ctactggatg   540
aactgggtca gcagaggcc tggacagggc ctcgagtgga tcggaatgat tcaccccagc   600
gacagcgaga cacggctgaa ccagaagttc aaggacaagg ccacactgac cgtggacaag   660
agcagcagca ccgcctacat gcagctgtct agccctacca gcgaggacag cgccgtgtat   720
tattgcgccc ggtccaccat gatcgccacc agagctatgg attactgggg ccagggcaca   780
agcgtgaccg tgtctagttt cgtgcccgtg ttcctgcctg ccaagcctac aacaaccct   840
gctcctagac tcctacacc agctcctaca atcgccagcc agcctctgtc tctgaggcct   900
gaagcttgta gacctgctgc tggcggagcc gtgcatacca gaggactgga tttcgcctgc   960
gacatctaca tctgggcccc tctggctgga acatgtggcg ttttgctgct gagcctcgtg  1020
```

```
atcaccctgt actgcaacca ccggaacaga agcaagcgga gccggctgct gcacagcgac    1080
tacatgaaca tgaccccccag acggcctggc cccaccagaa agcactacca gccttacgcc    1140
cctcccagag acttcgccgc ctaccggtcc agagtgaagt tcagcagaag cgccgacgcc    1200
cctgcctatc agcagggcca gaaccagctg tacaacgagc tgaacctggg cagacgggaa    1260
gagtacgatg tgctggacaa aagacgtggc cgggaccctg agatggggg aaagccgaga     1320 aggaagaacc ctcaggaagg cctgtacaat gaactgcaga agataagat ggcggaggcc     1380 tacagtgaga ttgggatgaa aggcgagcgc cggaggggca aggggcacga tggcctttac    1440
cagggtctca gtacagccac caaggacacc tacgacgccc ttcacatgca ggccctgccc    1500
cctcgctaa                                                            1509

<210> SEQ ID NO 33
<211> LENGTH: 1506
<212> TYPE: DNA
<213> ORGANISM: Artificial Sequence
<220> FEATURE:
<223> OTHER INFORMATION: Synthetic

<400> SEQUENCE: 33
atggccctgc ctgttacagc tctgctgctg cctctggctc tgcttctgca tgccgccaga      60
cctgacatcc agatgacaca gagccctagc agcctgtctg ccagcgtggg agacagagtg     120
accatcacat gcaaggccag ccaggacgtg gaattgccg tggcttggta tcagcagaaa      180
cccggcaagg tgcccaagct gctgatctac tgggccagca agacacac ggcgtgccc        240 gatagatttt ctggcagcgg ctctggcacc gacttcaccc tgaccatatc tagcctgcag     300
cctgaggacg tggccaccta ctactgtcag cagtacagca gctacccta caccttggc      360 cagggcacca aggtggaaat caagggcagc acaagcggca cggcaaaacc tggatctggc     420
gagggatcta ccaagggcga agtgcagctg gtggaatctg gcggaggact ggttcaacct    480
ggcggctctc tgagactgag ctgtgccgcc agcggcttcg acttcagcag atactggatg    540
agctgggtcc gacaggcccc tggcaaagga ctggaatgga tcggcgagat caaccccgac    600
agcagcacca tcaattacgc ccctagcctg aaggacaagt tcatcatcag ccgggacaac    660
gccaagaaca gcctgtacct gcagatgaac tccctgagag ccgaggacac cgccgtgtac    720
tattgcgcca gaccagacgg caactactgg tacttcgatg tgtggggcca gggaaccctg    780
gtcaccgtgt catctttcgt gcccgtgttc ctgcctgcca gcctacaac aacccctgct    840 cctagacctc ctacaccagc tcctacaatc gccagccagc tctgtctct gaggccagaa    900 gcttgtagac ctgctgctgg cggagccgtg catacaagag actggattt cgcctgcgac    960 atctacatct gggcccctct ggctggaaca tgtggcgtgt gctgctgag cctcgtgatc    1020 accctgtact gcaaccaccg gaacagaagc aagcggagcc ggctgctgca cagcgactac    1080
atgaacatga cccccagacg gcctggcccc accagaaagc actaccagcc ttacgcccct    1140
cccagagact tcgccgccta ccggtccaga gtgaagttca gcagaagcgc cgacgcccct    1200
gcctatcagc agggccagaa ccagctgtac aacgagctga acctgggcag acgggaagag   1260
tacgatgtgc tggacaaaag acgtggccgg gaccctgaga tggggggaaa gccgagaagg    1320
aagaaccctc aggaaggcct gtacaatgaa ctgcagaaag ataagatggc ggaggcctac    1380
agtgagattg ggatgaaagg cgagcgccgg aggggcaagg gcacgatgg cctttaccag    1440 ggtctcagta cagccaccaa ggacacctac gacgccttc acatgcaggc cctgccccct    1500
cgctaa                                                               1506
```

<210> SEQ ID NO 34
<211> LENGTH: 1512
<212> TYPE: DNA
<213> ORGANISM: Artificial Sequence
<220> FEATURE:
<223> OTHER INFORMATION: Synthetic

<400> SEQUENCE: 34

| | |
|---|---:|
| atggccctgc ctgttacagc tctgctgctg cctctggctc tgcttctgca tgccgccaga | 60 |
| cctgacatcg tgatgaccca gtctcagaaa tccatgagca ccagcgtggg cgacagagtg | 120 |
| tccatcacct gtaaagccag ccaggacgtg atcacaggcg tggcctggta tcagcagaag | 180 |
| cctggccagt ctcctaagct gctgatctac agcgccagct acagatacac cggcgtgccc | 240 |
| gatagattca caggcagcgg ctctggcacc gacttcacct tcaccatcag caacgtgcag | 300 |
| gccgaggatc tggccgtgta ctactgtcag cagcactaca gcacccctct gacctttggc | 360 |
| gccgaacaa agctggaact gaagggcagc acaagcggca gcgaaaaacc tggatctggc | 420 |
| gagggctcta ccaaaggcca ggttcagctt cagcagcctg gcgccgaact tgttagacct | 480 |
| ggcgcctctg tgaagctgtc ctgcaaggcc agcggctact ccttcaccac ctactggatg | 540 |
| aactgggtca gcagaggcc tggacagggc ctcgagtgga tcggaatgat tcaccccagc | 600 |
| gacagcgaga cacggctgaa ccagaagttc aaggacaagg ccacactgac cgtggacaag | 660 |
| agcagcagca ccgcctacat gcagctgtct agccctacca gcgaggacag cgccgtgtat | 720 |
| tattgcgccc ggtccaccat gatcgccacc agagctatgg attactgggg ccagggcaca | 780 |
| agcgtgaccg tgtctagttt cgtgcccgtg ttcctgcctg ccaagcctac aacaacccct | 840 |
| gctcctagac ctcctacacc agctcctaca atcgccagcc agcctctgtc tctgaggcct | 900 |
| gaagcttgta gacctgctgc tggcggagcc gtgcatacca gaggactgga tttcgcctgc | 960 |
| gacatctaca ctctgggcccc tctgctggaa catgtggcg ttttgctgct gagcctcgtg | 1020 |
| atcaccctgt actgcaacca ccggaacaag cggggcagaa agaagctgct gtacatcttc | 1080 |
| aagcagccct tcatgcggcc cgtgcagacc acccaggaag aggacggctg ctcctgcaga | 1140 |
| ttccccgagg aagaagaagg cggctgcgag ctgagagtga agttcagcag aagcgccgac | 1200 |
| gcccctgcct atcagcaggg ccagaaccag ctgtacaacg agctgaacct gggcagacgg | 1260 |
| gaagagtacg acgtgctgga caagcggaga ggcagggacc ctgagatggg cggcaagccc | 1320 |
| agaagaaaga ccccccagga aggcctgtat aacgaactgc agaaagacaa gatggccgag | 1380 |
| gcctacagcg agatcggaat gaagggcgag cggagaagag caagggcca cgatggcctg | 1440 |
| taccagggcc tgagcaccgc caccaaggac acctatgacg ccctgcacat gcaggccctg | 1500 |
| cccccccagat ga | 1512 |

<210> SEQ ID NO 35
<211> LENGTH: 2771
<212> TYPE: DNA
<213> ORGANISM: Artificial Sequence
<220> FEATURE:
<223> OTHER INFORMATION: Synthetic

<400> SEQUENCE: 35

| | |
|---|---:|
| atggccctgc ctgttacagc tctgctgctg cctctggctc tgcttctgca tgccgccaga | 60 |
| cctgacatcg tgatgaccca gtctcagaaa tccatgagca ccagcgtggg cgacagagtg | 120 |
| tccatcacct gtaaagccag ccaggacgtg atcacaggcg tggcctggta tcagcagaag | 180 |

```
cctggccagt ctcctaagct gctgatctac agcgccagct acagatacac cggcgtgccc    240
gatagattca caggcagcgg ctctggcacc gacttcacct tcaccatcag caacgtgcag    300
gccgaggatc tggccgtgta ctactgtcag cagcactaca gcacccctct gacctttggc    360 gccgaacaa agctggaact gaagggcagc acaagcggca gcggaaaacc tggatctggc    420
gagggctcta ccaaaggcca ggttcagctt cagcagcctg gcgccgaact tgttagacct    480
ggcgcctctg tgaagctgtc ctgcaaggcc agcggctact ccttcaccac ctactggatg    540
aactgggtca agcagaggcc tggacagggc ctcgagtgga tcggaatgat tcaccccagc    600
gacagcgaga cacggctgaa ccagaagttc aaggacaagg ccacactgac cgtggacaag    660
agcagcagca ccgcctacat gcagctgtct agccctacca gcgaggacag cgccgtgtat    720
tattgcgccc ggtccaccat gatcgccacc agagctatgg attactgggg ccagggcaca    780
agcgtgaccg tgtctagttt cgtgcccgtg ttcctgcctg ccaagcctac aacaaccct    840 gctcctagac ctcctacacc agctcctaca atcgccagcc agcctctgtc tctgaggcct    900
gaagcttgta gacctgctgc tggcggagcc gtgcatacca gaggactgga tttcgcctgc    960
gacatctaca tctgggcccc tctggctgga acatgtggcg ttttgctgct gagcctcgtg    1020
atcaccctgt actgcaacca ccggaacaga agcaagcgga gccggctgct gcacagcgac    1080
tacatgaaca tgaccccag acggcctggc cccaccagaa agcactacca gccttacgcc    1140
cctcccagag acttcgccgc ctaccggtcc agagtgaagt tcagcagaag cgccgacgcc    1200
cctgcctatc agcagggcca gaaccagctg tacaacgagc tgaacctggg cagacgggaa    1260
gagtacgatg tgctggacaa aagacgtggc cgggaccctg agatgggggg aaagccgaga    1320
aggaagaacc ctcaggaagg cctgtacaat gaactgcaga agataagat ggcggaggcc    1380 tacagtgaga ttgggatgaa aggcgagcgc cggaggggca aggggcacga tggcctttac    1440
cagggtctca gtacagccac caaggacacc tacgacgccc ttcacatgca ggccctgccc    1500
cctcgcagag ccgagggcag gggaagtctt ctaacatgcg gggacgtgga ggaaaatccc    1560
gggcccatgc tcgagggagt gcaggtggaa accatctccc caggagacgg gcgcaccttc    1620
cccaagcgcg gccagacctg cgtggtgcac tacaccggga tgcttgaaga tggaaagaaa    1680
gttgattcct cccgggacag aaacaagccc tttaagttta tgctaggcaa gcaggaggtg    1740
atccgaggct gggaagaagg ggttgcccag atgagtgtgg gtcagagagc caaactgact    1800
atatctccag attatgccta tggtgccact gggcacccag gcatcatccc accacatgcc    1860
actctcgtct tcgatgtgga gcttctaaaa ctggaatctg gcggtggatc cggagtcgac    1920
ggatttggtg atgtcggtgc tcttgagagt ttgagggaa atgcagattt ggcttacatc    1980
ctgagcatgg agccctgtgg ccactgcctc attatcaaca atgtgaactt ctgccgtgag    2040
tccgggctcc gcacccgcac tggctccaac atcgactgtg agaagttgcg gcgtcgcttc    2100
tcctcgctgc atttcatggt ggaggtgaag ggcgacctga ctgccaagaa aatggtgctg    2160
gctttgctgg agctggcgca gcaggaccac ggtgctctgg actgctgcgt ggtggtcatt    2220
ctctctcacg gctgtcaggc cagccacctg cagttcccag ggctgtctca cggcacagat    2280
ggatgccctg tgtcggtcga aagattgtg aacatcttca atgggaccag ctgccccagc    2340
ctgggaggga agcccaagct cttttttcatc caggcctgtg gtgggagca gaaagaccat    2400 gggtttgagg tggcctccac ttcccctgaa gacgagtccc ctggcagtaa ccccgagcca    2460
gatgccaccc cgttccagga aggtttgagg accttcgacc agctggacgc catatctagt    2520
ttgcccacac ccagtgacat cttttgtgtcc tactctactt tcccaggttt tgtttcctgg    2580
```

```
agggacccca agagtggctc ctggtacgtt gagaccctgg acgacatctt tgagcagtgg    2640
gctcactctg aagacctgca gtccctcctg cttagggtcg ctaatgctgt ttcggtgaaa    2700
gggatttata aacagatgcc tggttgcttt aatttcctcc ggaaaaaact tttctttaaa    2760
acatcagctt a                                                         2771

<210> SEQ ID NO 36
<211> LENGTH: 2775
<212> TYPE: DNA
<213> ORGANISM: Artificial Sequence
<220> FEATURE:
<223> OTHER INFORMATION: Synthetic

<400> SEQUENCE: 36
atggtcgagg gagtgcaggt ggaaaccatc tccccaggag acgggcgcac cttccccaag      60
cgcggccaga cctgcgtggt gcactacacc gggatgcttg aagatggaaa gaaagttgat     120
tcctcccggg acagaaacaa gccctttaag tttatgctag caagcagga ggtgatccga      180 ggctgggaag aaggggttgc ccagatgagt gtgggtcaga gagccaaact gactatatct     240
ccagattatg cctatggtgc cactgggcac ccaggcatca tcccaccaca tgccactctc     300
gtcttcgatg tggagcttct aaaactggaa tctggcggtg gatccggagt cgacggattt     360
ggtgatgtcg gtgctcttga gagtttgagg ggaaatgcag atttggctta catcctgagc     420
atggagccct gtggccactg cctcattatc aacaatgtga acttctgccg tgagtccggg     480
ctccgcaccc gcactggctc caacatcgac tgtgagaagt gcggcgtcg cttctcctcg      540 ctgcatttca tggtggaggt gaagggcgac ctgactgcca agaaaatggt gctggctttg     600
ctggagctgg cgcagcagga ccacggtgct ctggactgct gcgtggtggt cattctctct     660
cacggctgtc aggccagcca cctgcagttc ccaggggctg tctacggcac agatggatgc     720
cctgtgtcgg tcgagaagat tgtgaacatc ttcaatggga ccagctgccc cagcctggga     780
gggaagccca agctcttttt catccaggcc tgtggtgggg agcagaaaga tcatgggttt     840
gaggtggcct ccacttcccc tgaagacgag tccctggca gtaaccccga gccagatgcc      900
accccgttcc aggaaggttt gaggaccttc gaccagctgg acgccatatc tagttttgccc    960 acacccagtg acatctttgt gtcctactct actttcccag ttttgtttc ctggagggac     1020 cccaagagtg gctcctggta cgttgagacc ctggacgaca tctttgagca gtgggctcac    1080
tctgaagacc tgcagtccct cctgcttagg gtcgctaatg ctgtttcggt gaaagggatt    1140
tataaacaga tgcctggttg cttaatttc ctccggaaaa aacttttctt taaaacatca    1200
gctagcagag ccgagggcag gggaagtctt ctaacatgcg gggacgtgga ggaaaatccc    1260
gggcccatgg ccctgcctgt tacagctctg ctgctgcctc tggctctgct tctgcatgcc    1320
gccagacctg acatcgtgat gacccagtct cagaaatcca tgagcaccag cgtgggcgac    1380
agagtgtcca tcacctgtaa agccagccag gacgtgatca caggcgtggc ctggtatcag    1440
cagaagcctg gccagtctcc taagctgctg atctacagcg ccagctacag atacaccggc    1500
gtgcccgata gattcacagg cagcggctct ggcaccgact tcaccttcac catcagcaac    1560
gtgcaggcca aggatctggc cgtgtactac tgtcagcagc actacagcac ccctctgacc    1620
tttggcgccg gaacaaagct ggaactgaag ggcagcacaa gcggcagcgg aaaacctgga    1680
tctggcgagg gctctaccaa aggccaggtt cagcttcagc agcctggcgc cgaacttgtt    1740
agacctggcg cctctgtgaa gctgtcctgc aaggccagcg gctactcctt caccacctac    1800
```

```
tggatgaact gggtcaagca gaggcctgga cagggcctcg agtggatcgg aatgattcac   1860
cccagcgaca gcgagacacg gctgaaccag aagttcaagg acaaggccac actgaccgtg   1920
gacaagagca gcagcaccgc ctacatgcag ctgtctagcc ctaccagcga ggacagcgcc   1980
gtgtattatt gcgcccggtc caccatgatc gccaccagag ctatggatta ctggggccag   2040
ggcacaagcg tgaccgtgtc tagtttcgtg cccgtgttcc tgcctgccaa gcctacaaca   2100
acccctgctc ctagacctcc tacaccagct cctacaatcg ccagccagcc tctgtctctg   2160
aggcctgaag cttgtagacc tgctgctggc ggagccgtgc ataccagagg actggatttc   2220
gcctgcgaca tctacatctg gcccctctg gctggaacat gtggcgtttt gctgctgagc   2280
ctcgtgatca ccctgtactg caaccaccgg aacagaagca gcggagccg gctgctgcac   2340 agcgactaca tgaacatgac ccccagacgg cctggcccca ccagaaagca ctaccagcct   2400
tacgcccctc ccagagactt cgccgcctac cggtccagag tgaagttcag cagaagcgcc   2460 gacgccctg cctatcagca gggccagaac cagctgtaca cgagctgaa cctgggcaga   2520 cgggaagagt acgatgtgct ggacaaaaga cgtggccggg accctgagat ggggggaaag   2580
ccgagaagga agaaccctca ggaaggcctg tacaatgaac tgcagaaaga taagatggcg   2640
gaggcctaca gtgagattgg gatgaaaggc gagcgccgga ggggcaaggg gcacgatggc   2700
ctttaccagg gtctcagtac agccaccaag gacacctacg acgcccttca catgcaggcc   2760
ctgccccctc gctaa                                                    2775

<210> SEQ ID NO 37
<211> LENGTH: 335
<212> TYPE: PRT
<213> ORGANISM: Homo sapiens

<400> SEQUENCE: 37

Met Ala Gly Ser Pro Thr Cys Leu Thr Leu Ile Tyr Ile Leu Trp Gln
1               5                   10                  15

Leu Thr Gly Ser Ala Ala Ser Gly Pro Val Lys Glu Leu Val Gly Ser
            20                  25                  30

Val Gly Gly Ala Val Thr Phe Pro Leu Lys Ser Lys Val Lys Gln Val
        35                  40                  45

Asp Ser Ile Val Trp Thr Phe Asn Thr Thr Pro Leu Val Thr Ile Gln
    50                  55                  60

Pro Glu Gly Gly Thr Ile Val Thr Gln Asn Arg Asn Arg Glu Arg
65                  70                  75                  80

Val Asp Phe Pro Asp Gly Gly Tyr Ser Leu Lys Leu Ser Lys Leu Lys
                85                  90                  95

Lys Asn Asp Ser Gly Ile Tyr Tyr Val Gly Ile Tyr Ser Ser Ser Leu
            100                 105                 110

Gln Gln Pro Ser Thr Gln Glu Tyr Val Leu His Val Tyr Glu His Leu
        115                 120                 125

Ser Lys Pro Lys Val Thr Met Gly Leu Gln Ser Asn Lys Asn Gly Thr
    130                 135                 140

Cys Val Thr Asn Leu Thr Cys Cys Met Glu His Gly Glu Glu Asp Val
145                 150                 155                 160

Ile Tyr Thr Trp Lys Ala Leu Gly Gln Ala Ala Asn Glu Ser His Asn
                165                 170                 175

Gly Ser Ile Leu Pro Ile Ser Trp Arg Trp Gly Glu Ser Asp Met Thr
            180                 185                 190

Phe Ile Cys Val Ala Arg Asn Pro Val Ser Arg Asn Phe Ser Ser Pro
```

```
            195                 200                 205
Ile Leu Ala Arg Lys Leu Cys Glu Gly Ala Ala Asp Pro Asp Ser
    210                 215                 220
Ser Met Val Leu Leu Cys Leu Leu Val Pro Leu Leu Leu Ser Leu
225                 230                 235                 240
Phe Val Leu Gly Leu Phe Leu Trp Phe Leu Lys Arg Glu Arg Gln Glu
                245                 250                 255
Glu Tyr Ile Glu Glu Lys Lys Arg Val Asp Ile Cys Arg Glu Thr Pro
            260                 265                 270
Asn Ile Cys Pro His Ser Gly Glu Asn Thr Glu Tyr Asp Thr Ile Pro
            275                 280                 285
His Thr Asn Arg Thr Ile Leu Lys Glu Asp Pro Ala Asn Thr Val Tyr
            290                 295                 300
Ser Thr Val Glu Ile Pro Lys Lys Met Glu Asn Pro His Ser Leu Leu
305                 310                 315                 320
Thr Met Pro Asp Thr Pro Arg Leu Phe Ala Tyr Glu Asn Val Ile
                325                 330                 335

<210> SEQ ID NO 38
<211> LENGTH: 400
<212> TYPE: PRT
<213> ORGANISM: Artificial Sequence
<220> FEATURE:
<223> OTHER INFORMATION: synthetic

<400> SEQUENCE: 38

Met Val Glu Gly Val Gln Val Glu Thr Ile Ser Pro Gly Asp Gly Arg
1               5                   10                  15
Thr Phe Pro Lys Arg Gly Gln Thr Cys Val Val His Tyr Thr Gly Met
                20                  25                  30
Leu Glu Asp Gly Lys Lys Val Asp Ser Ser Arg Asp Arg Asn Lys Pro
            35                  40                  45
Phe Lys Phe Met Leu Gly Lys Gln Glu Val Ile Arg Gly Trp Glu Glu
    50                  55                  60
Gly Val Ala Gln Met Ser Val Gly Gln Arg Ala Lys Leu Thr Ile Ser
65                  70                  75                  80
Pro Asp Tyr Ala Tyr Gly Ala Thr Gly His Pro Gly Ile Ile Pro Pro
                85                  90                  95
His Ala Thr Leu Val Phe Asp Val Glu Leu Leu Lys Leu Glu Ser Gly
                100                 105                 110
Gly Gly Ser Gly Val Asp Gly Phe Gly Asp Val Gly Ala Leu Glu Ser
            115                 120                 125
Leu Arg Gly Asn Ala Asp Leu Ala Tyr Ile Leu Ser Met Glu Pro Cys
    130                 135                 140
Gly His Cys Leu Ile Ile Asn Asn Val Asn Phe Cys Arg Glu Ser Gly
145                 150                 155                 160
Leu Arg Thr Arg Thr Gly Ser Asn Ile Asp Cys Glu Lys Leu Arg Arg
                165                 170                 175
Arg Phe Ser Ser Leu His Phe Met Val Glu Val Lys Gly Asp Leu Thr
            180                 185                 190
Ala Lys Lys Met Val Leu Ala Leu Leu Glu Leu Ala Gln Gln Asp His
            195                 200                 205
Gly Ala Leu Asp Cys Cys Val Val Val Ile Leu Ser His Gly Cys Gln
    210                 215                 220
Ala Ser His Leu Gln Phe Pro Gly Ala Val Tyr Gly Thr Asp Gly Cys
```

```
                    225                 230                 235                 240

Pro Val Ser Val Glu Lys Ile Val Asn Ile Phe Asn Gly Thr Ser Cys
                245                 250                 255

Pro Ser Leu Gly Gly Lys Pro Lys Leu Phe Phe Ile Gln Ala Cys Gly
                260                 265                 270

Gly Glu Gln Lys Asp His Gly Phe Glu Val Ala Ser Thr Ser Pro Glu
                275                 280                 285

Asp Glu Ser Pro Gly Ser Asn Pro Glu Pro Asp Ala Thr Pro Phe Gln
                290                 295                 300

Glu Gly Leu Arg Thr Phe Asp Gln Leu Asp Ala Ile Ser Ser Leu Pro
305                 310                 315                 320

Thr Pro Ser Asp Ile Phe Val Ser Tyr Ser Thr Phe Pro Gly Phe Val
                325                 330                 335

Ser Trp Arg Asp Pro Lys Ser Gly Ser Trp Tyr Val Glu Thr Leu Asp
                340                 345                 350

Asp Ile Phe Glu Gln Trp Ala His Ser Glu Asp Leu Gln Ser Leu Leu
                355                 360                 365

Leu Arg Val Ala Asn Ala Val Ser Val Lys Gly Ile Tyr Lys Gln Met
                370                 375                 380

Pro Gly Cys Phe Asn Phe Leu Arg Lys Lys Leu Phe Phe Lys Thr Ser
385                 390                 395                 400

<210> SEQ ID NO 39
<211> LENGTH: 9
<212> TYPE: PRT
<213> ORGANISM: Artificial Sequence
<220> FEATURE:
<223> OTHER INFORMATION: synthetic
<220> FEATURE:
<221> NAME/KEY: miscellaneous
<222> LOCATION: (5)..(5)
<223> OTHER INFORMATION: X is any naturally occurring amino acid residue

<400> SEQUENCE: 39

Gly Asp Val Glu Xaa Asn Pro Gly Pro
1               5

<210> SEQ ID NO 40
<211> LENGTH: 4
<212> TYPE: PRT
<213> ORGANISM: Artificial Sequence
<220> FEATURE:
<223> OTHER INFORMATION: synthetic
<220> FEATURE:
<221> NAME/KEY: miscellaneous
<222> LOCATION: (2)..(2)
<223> OTHER INFORMATION: X is any naturally occurring amino acid
<220> FEATURE:
<221> NAME/KEY: miscellaneous
<222> LOCATION: (3)..(3)
<223> OTHER INFORMATION: X is arginine or lysine

<400> SEQUENCE: 40

Arg Xaa Xaa Arg
1
```

ANTI-SLAMF7 CHIMERIC ANTIGEN RECEPTORS

CROSS-REFERENCE TO RELATED APPLICATIONS

This patent application is a U.S. National Phase Patent Application of co-pending International Patent Application No. PCT/US2019/039239, filed Jun. 26, 2019, which claims the benefit of U.S. Provisional Patent Application No. 62/693,779, filed Jul. 3, 2018, each of which is incorporated by reference in its entirety herein.

STATEMENT REGARDING FEDERALLY SPONSORED RESEARCH OR DEVELOPMENT

This invention was made with Government support under project number Z01ZIABC01143906 by the National Institutes of Health, National Cancer Institute. The Government has certain rights in the invention.

INCORPORATION-BY-REFERENCE OF MATERIAL SUBMITTED ELECTRONICALLY

Incorporated by reference in its entirety herein is a computer-readable nucleotide/amino acid sequence listing submitted concurrently herewith and identified as follows: One 63,653 Byte ASCII (Text) file named "751339 ST25.TXT," dated Dec. 18, 2020.

BACKGROUND OF THE INVENTION

Cancer is a public health concern. Despite advances in treatments such as chemotherapy, the prognosis for many cancers may be poor. For example, therapies for multiple myeloma (MM) may cause remissions, but many patients eventually relapse and die. Accordingly, there exists an unmet need for additional treatments for cancer.

BRIEF SUMMARY OF THE INVENTION

An embodiment of the invention provides a nucleic acid comprising: (a) a suicide gene; and (b) a nucleotide sequence encoding a chimeric antigen receptor (CAR), wherein the CAR comprises an antigen recognition domain, a transmembrane (TM) domain, and a T cell activation domain, and wherein the CAR has antigenic specificity for signaling lymphocyte activating molecule F7 (SLAMF7).

Another embodiment of the invention provides a nucleic acid comprising a nucleotide sequence encoding a CAR, wherein the CAR comprises an antigen recognition domain, a TM domain, and a T cell activation domain, and wherein the CAR has antigenic specificity for SLAMF7.

Still another embodiment of the invention provides a CAR comprising an antigen recognition domain, a TM domain, and a T cell activation domain, wherein the CAR has antigenic specificity for SLAMF7, wherein the CAR does not comprise any of a Myc tag, an IgG4-Fc spacer, or an IgG4-Fc spacer which has been modified to prevent binding of an Fc receptor.

Further embodiments of the invention provide related protein(s) encoded by the nucleic acids, recombinant expression vectors, host cells, populations of cells, and pharmaceutical compositions.

Additional embodiments of the invention provide related methods of treating or preventing cancer in a mammal.

BRIEF DESCRIPTION OF THE SEVERAL VIEWS OF THE DRAWING(S)

Figure 1B:
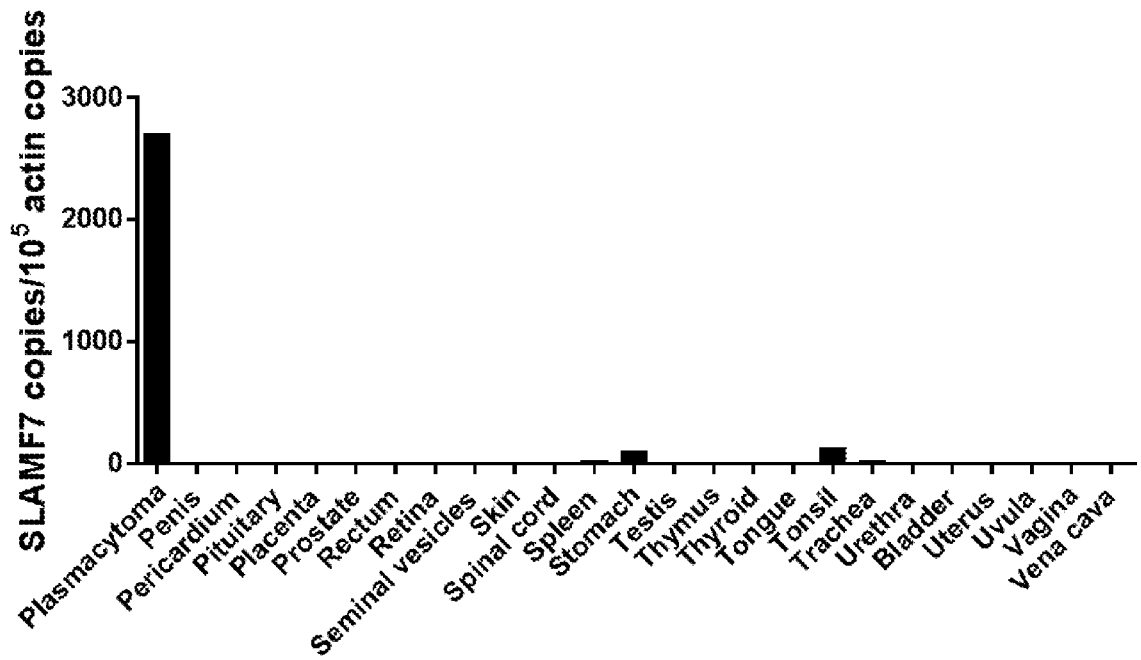

FIGS. 1A and 1B are graphs showing the number of SLAM7 copies per $10^5$ copies of β-actin cDNA measured by qPCR in plasmacytoma from a patient with multiple myeloma (positive control) or in the indicated normal tissues. Neoplastic plasma cells made up 93% of the total cells in the plasmacytoma sample.

Figure 2:
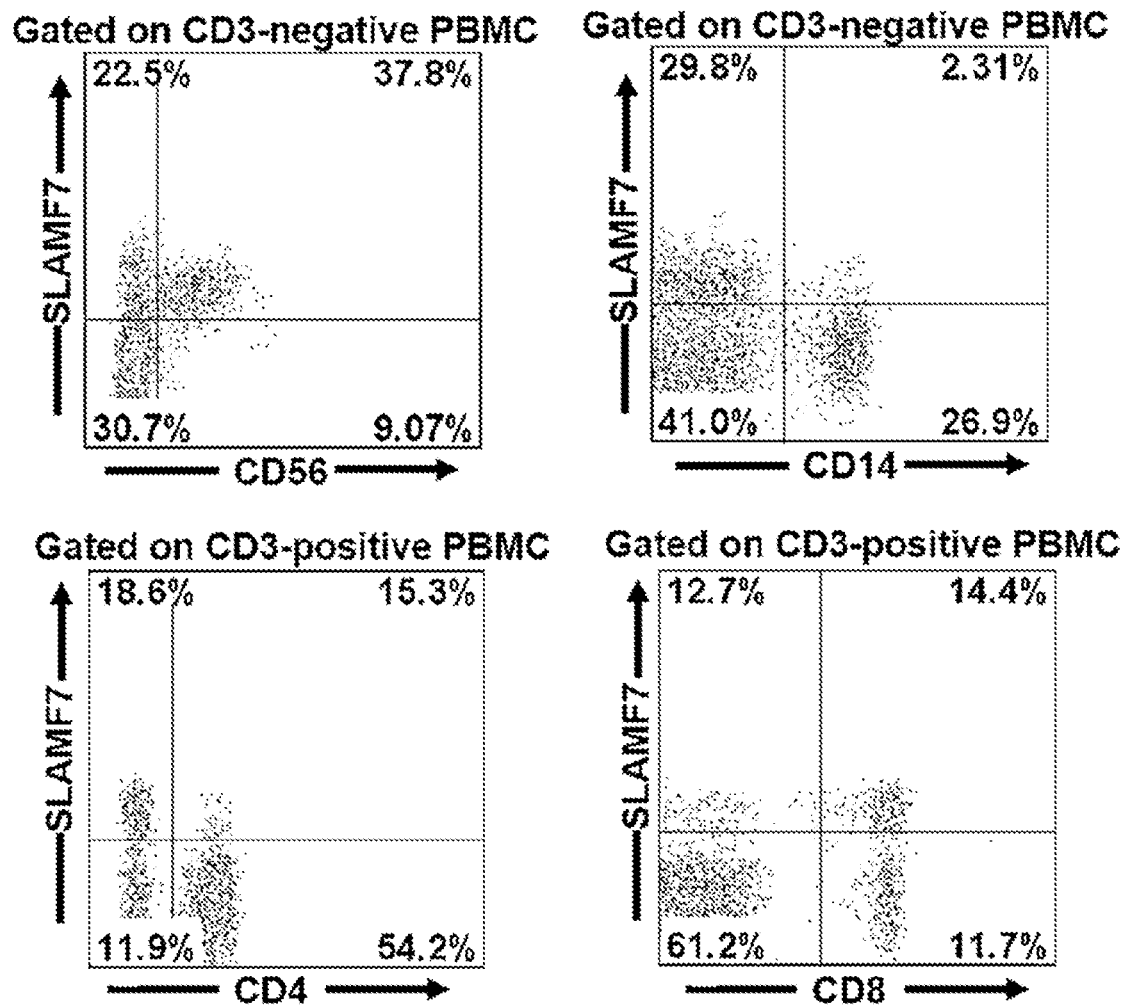

FIG. 2 is a set of plots showing the level of SLAMF7 expression on peripheral blood mononuclear cells gated on CD3 lymphocytes. The upper left plot was gated on CD3-negative lymphocytes. It shows SLAMF7 expression on most CD3-negative, CD56+ cells, which are NK cells. The upper right plot was gated on CD3-negative lymphocytes. It shows SLAMF7 expression on a small fraction of CD3-negative, CD14+ cells, which are monocytes. The lower left plot was gated on CD3+ lymphocytes. It shows SLAMF7 expression on a minority of $CD3^+CD4^+$ cells. The lower right plot is gated on CD3+ lymphocytes. It shows SLAMF7 expression on a substantial fraction of $CD3^+CD8^+$ cells. Results are representative of 4 different experiments with cells from 4 different donors.

Figure 3:
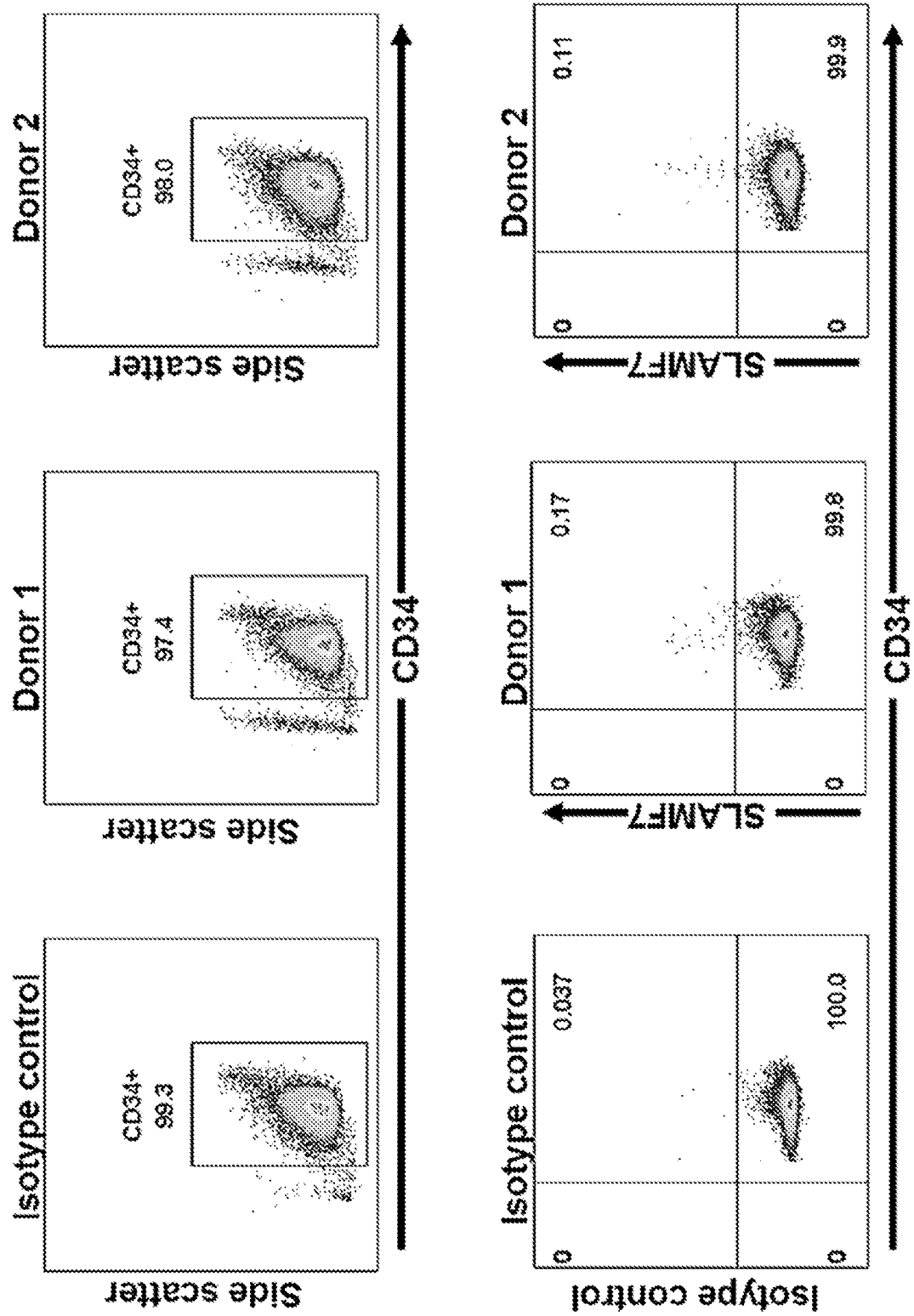

FIG. 3 is a set of plots showing that $CD34^+$ hematopoietic stem cells do not express SLAMF7. The upper row of plots shows data from 2 donors that were sorted for CD34 expression. The cells were stained for CD34 and analyzed by flow cytometry. Greater than 97% of the cells expressed CD34. The lower row of plots shows sorted $CD34^+$ cells that were stained for SLAMF7 and CD34 expression. The $CD34^+$ cells did not express SLAMF7. Staining by an isotype matched control antibody is also shown.

Figure 4A:
Figure 4B:
Figure 4C:
Figure 4D:
Figure 4E:

FIGS. 4A-4E are schematics illustrating the structures of CARs. FIG. 4A illustrates that Luc90-CD828Z includes a signal sequence (SS) from human CD8a. After the SS is a scFv made up from N-terminus to C-terminus of the light chain variable region of Luc90, the 218 linker, and the heavy chain variable region of Luc90. After the scFv, there is a CD8a hinge and transmembrane domain followed by cytoplasmic CD28 and CD3ζ domains. FIG. 4B illustrates that HuLuc63-CD828Z has the same sequence as Luc90-CD828Z except the huLuc63 light chain and heavy chain variable regions were substituted for the Luc90 light chain and heavy chain variable regions. FIG. 4C illustrates that Luc90-CD8BBZ has the same sequence as Luc90-CD828Z except that the CD28 moiety in Luc90-CD828Z is replaced with a 4-1BB moiety. FIG. 4D illustrates that Luc90-CD828Z-IC9 is made up of the same CAR sequence illustrated in FIG. 4A followed by the IC9 suicide gene. IC9 is made up of a modified FKBP12 domain followed by a modified caspase 9 sequence. FIG. 4E illustrates that IC9-Luc90-CD828Z is made up of IC9 followed by the same CAR sequence illustrated in FIG. 4A.

Figure 5:
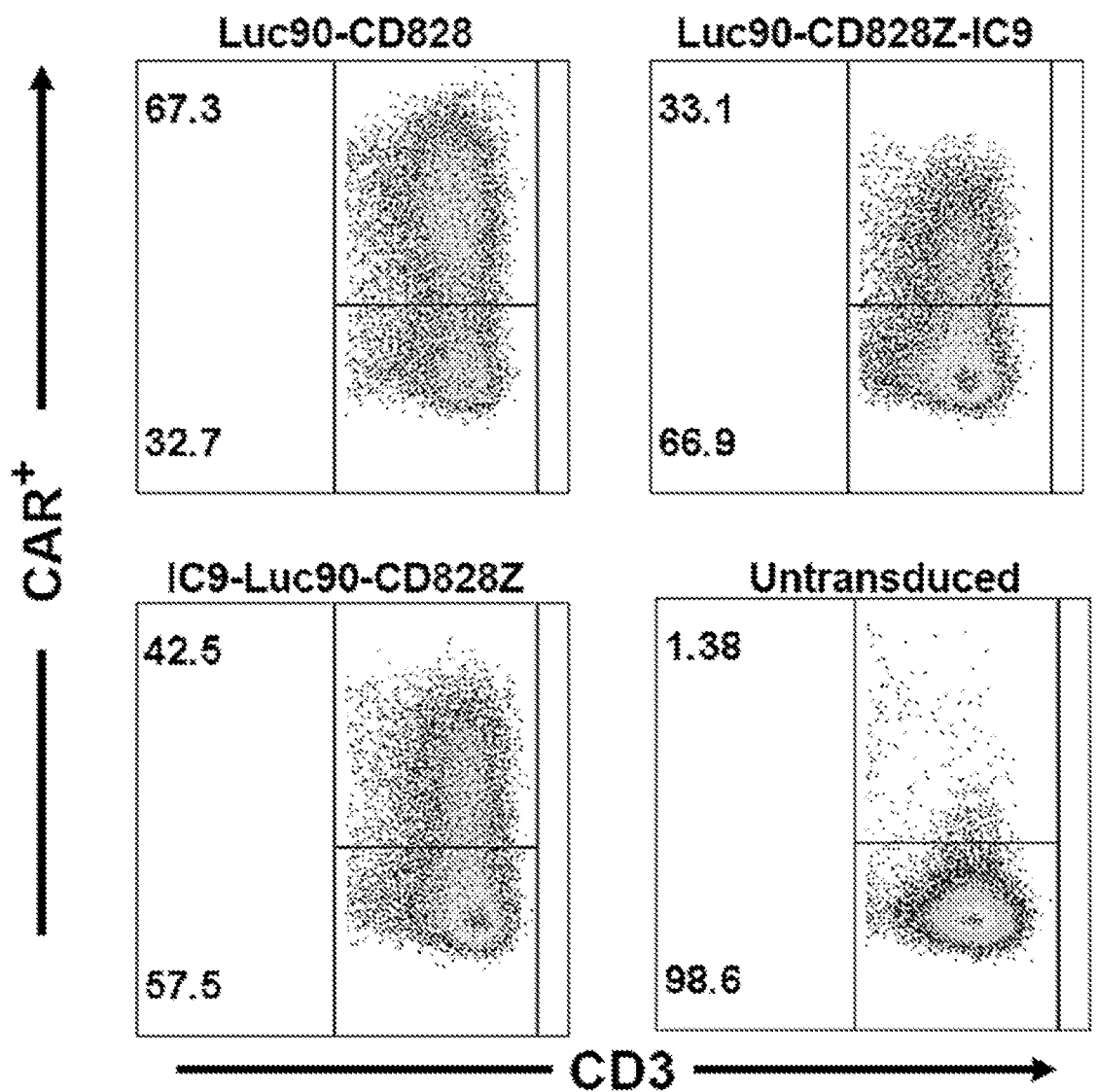

FIG. 5 is a set of plots showing that anti-SLAMF7 CARs are expressed on primary human T cells. T cells were transduced with gamma-retroviruses encoding the indicated CARs. Seven days after the start of T-cell cultures (4 days after transduction), CAR expression was measured by protein L staining followed by flow cytometry. The plots were gated on live lymphocytes. Results are representative of 7 experiments with 7 different donors.

Figure 6:
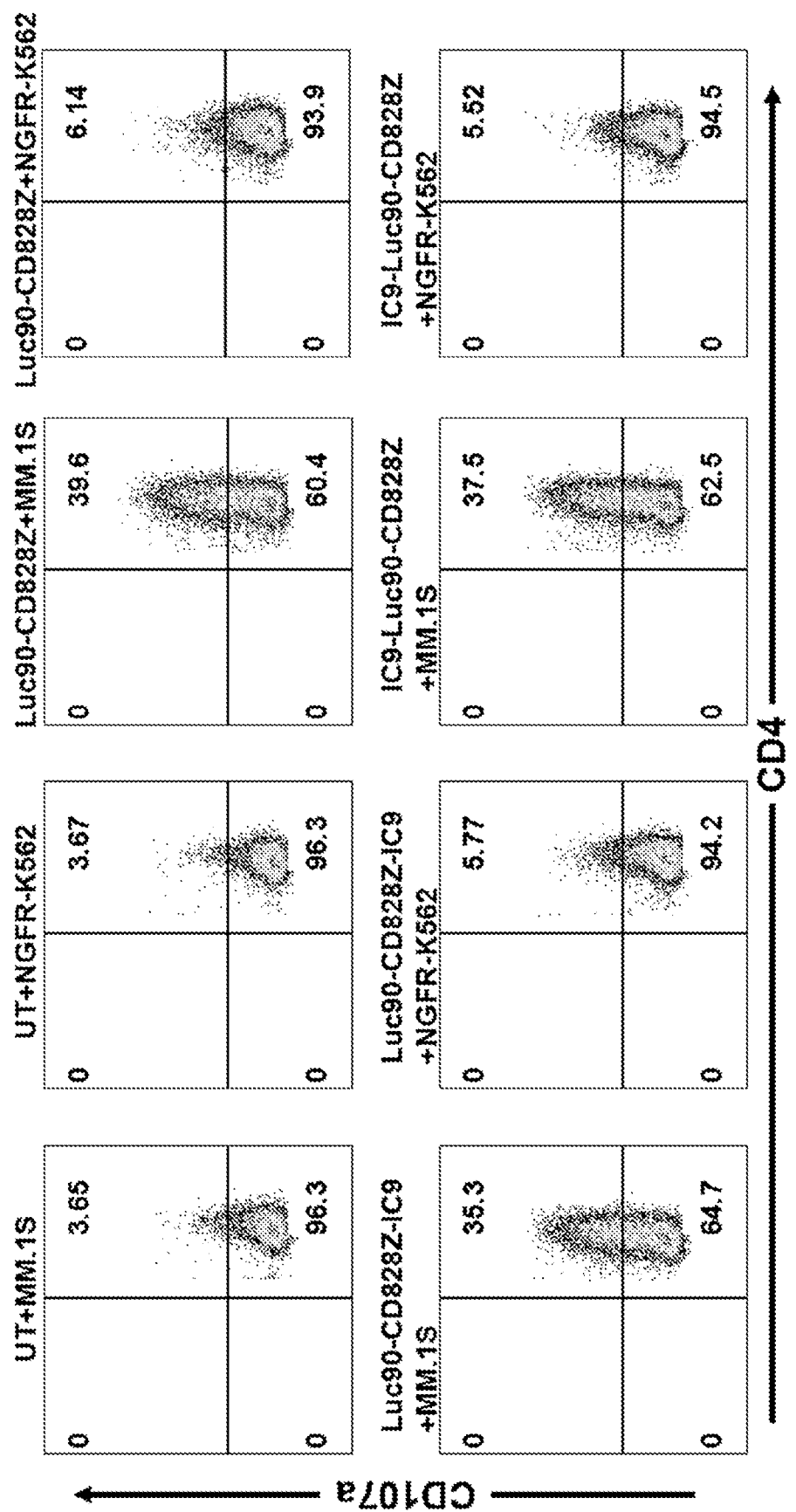

FIG. 6 is a set of plots showing that $CD4^+$ T cells expressing anti-SLAMF7 CAR constructs degranulate specifically in response to $SLAMF7^+$ target cells. The plots were gated on live, $CD3^+$ lymphocytes. T cells that were either untransduced (UT) or transduced with the indicated CAR construct were cultured with either $SLAMF7^+$ MM.1S cells or SLAMF7-negative NGFR-K562 cells as the plot titles indicate. CD107a upregulation occurred when CAR-expressing T cells were cultured with MM.1S cells. Results are representative of 4 experiments with 4 different donors.

Figure 7:
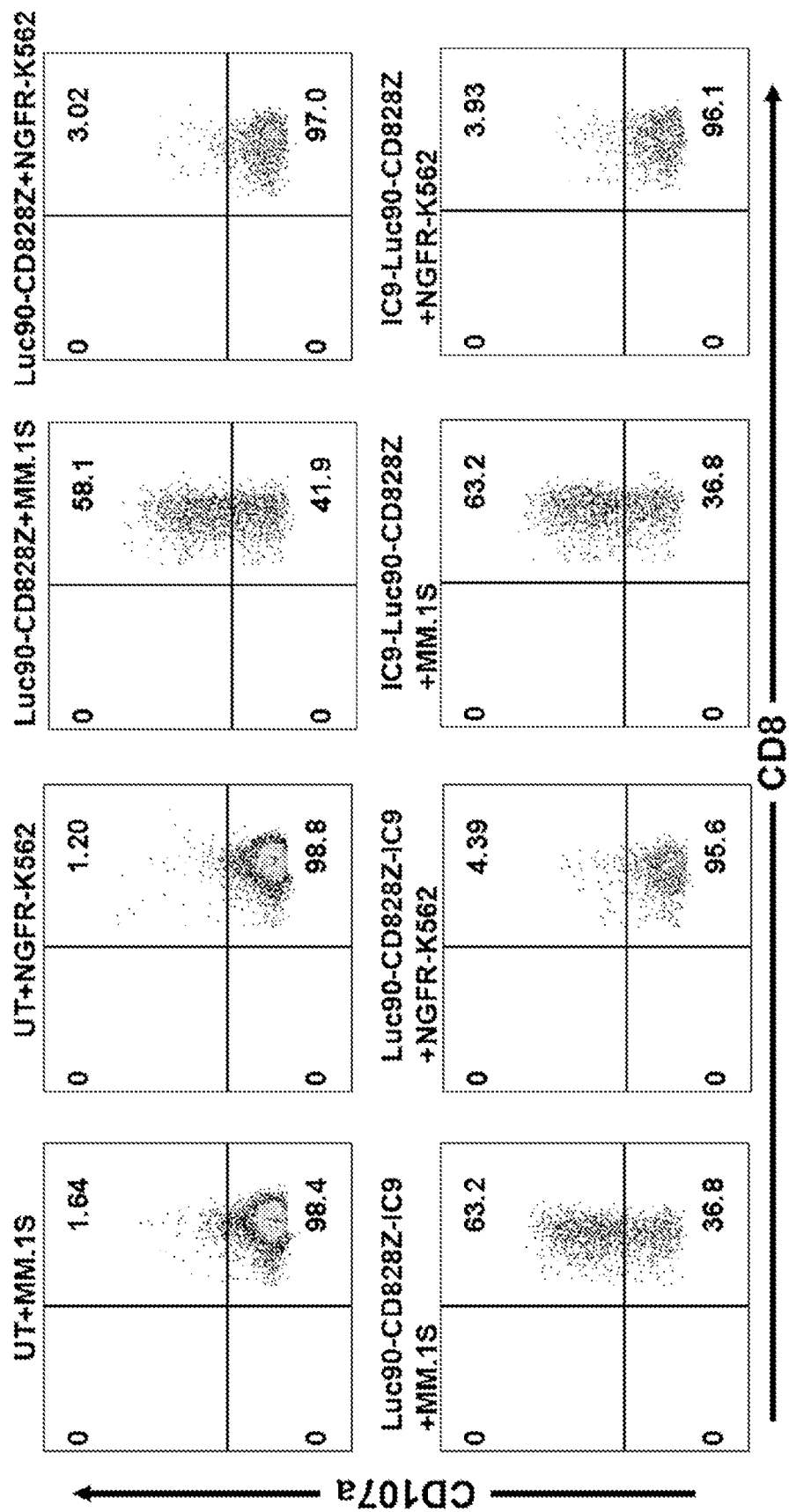

FIG. 7 is a set of plots showing that CD8+ T cells expressing anti-SLAMF7 CAR constructs degranulate specifically in response to SLAMF7+ target cells. The plots were gated on live, CD3+ lymphocytes. T cells that were either untransduced (UT) or transduced with the indicated CAR construct were cultured with either SLAMF7+ MM.1S cells or SLAMF7-negative NGFR-K562 cells as the plot titles indicate. CD107a upregulation occurred when CAR-expressing T cells were cultured with MM.1S cells.

Figure 8A:
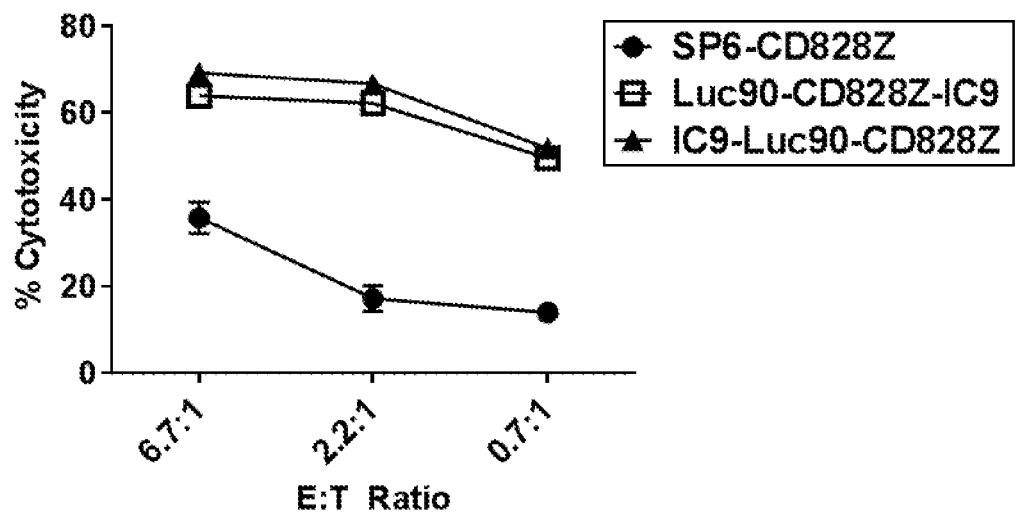
Figures 8B, 8C:
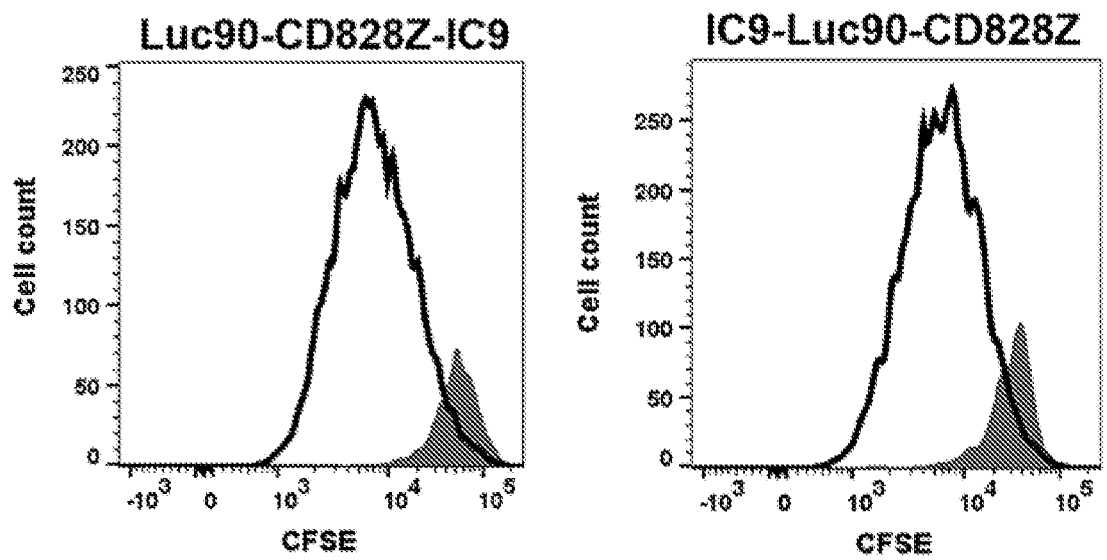

FIGS. 8A-8C are graphs that illustrate that T cells expressing anti-SLAMF7 CARs kill SLAMF7+ cells and proliferate specifically in response to SLAMF7. FIG. 8A is a graph that illustrates that T cells expressing either Luc90-CD828Z-IC9 or IC9-Luc90-CD828Z specifically killed the SLAMF7+ MM.1S cells. T cells expressing the SP6-CD828Z negative-control CAR killed MM.1S cells much less efficiently. The curves show killing of MM.1S cells relative to the killing of control CCRF-CEM cells, which are SLAMF7-negative. FIG. 8B is a graph illustrating the results when CFSE-labeled T cells expressing Luc90-CD828Z-IC9 were cultured with either SLAMF7-K562 target cells (open histograms) or NGFR-K562 negative-control target cells (grey histograms). FIG. 8C is a graph illustrating the results when CFSE-labeled T cells expressing IC9-Luc90-CD828Z were cultured with either SLAMF7-K562 target cells (open histograms) or NGFR-K562 negative-control target cells (grey histograms). The CAR T cells proliferated more, as shown by greater CFSE dilution, when cultured with SLAMF7-K562 cells than when cultured with NGFR-K562 cells. The culture period of the experiment was 4 days. The plots were gated on CAR-expressing, CD3+, live lymphocytes. As indicated by the size of the histograms, more cells accumulated by the end of the culture period when the CAR T cells were cultured with SLAMF7-K562 target cells.

Figure 9:
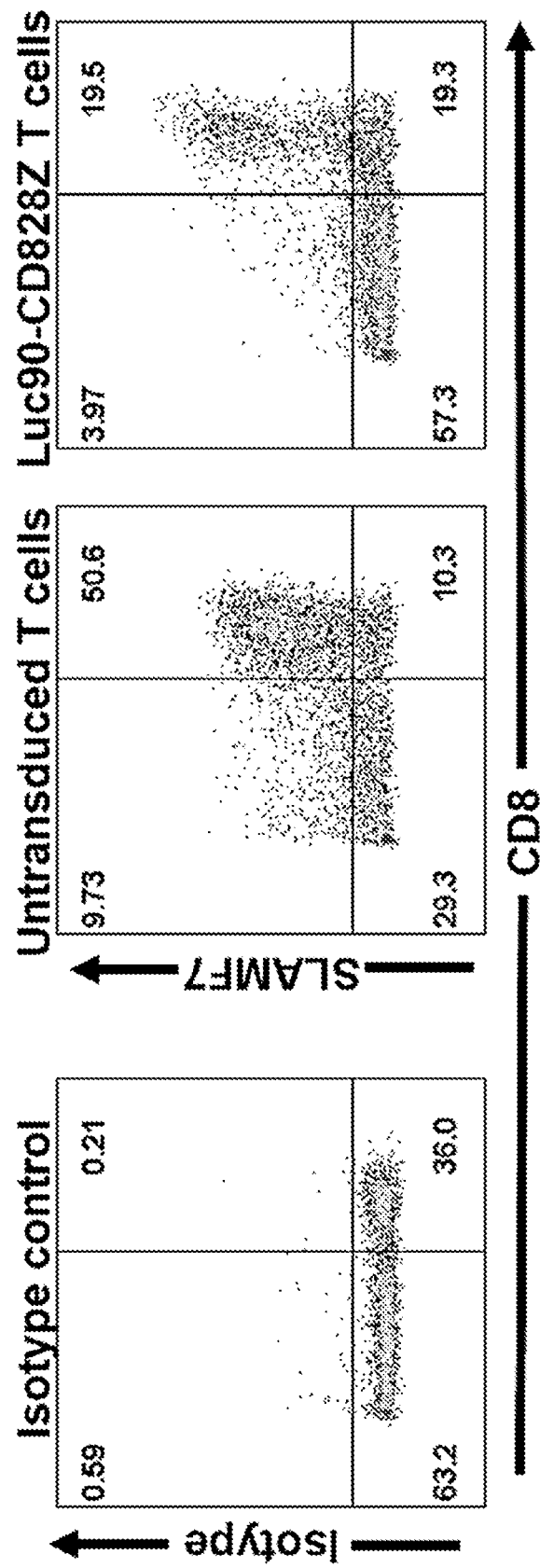

FIG. 9 is a set of plots illustrating that SLAMF7 is expressed on CD8+ T cells at the end of transduction. T cells were transduced on day 2 of culture. SLAMF7 expression was assessed on day 3 of culture on untransduced T cells and on Luc90-CD828Z-transduced T cells. Isotype control staining is also shown. The plots were gated on CD3+, live lymphocytes.

Figure 10:
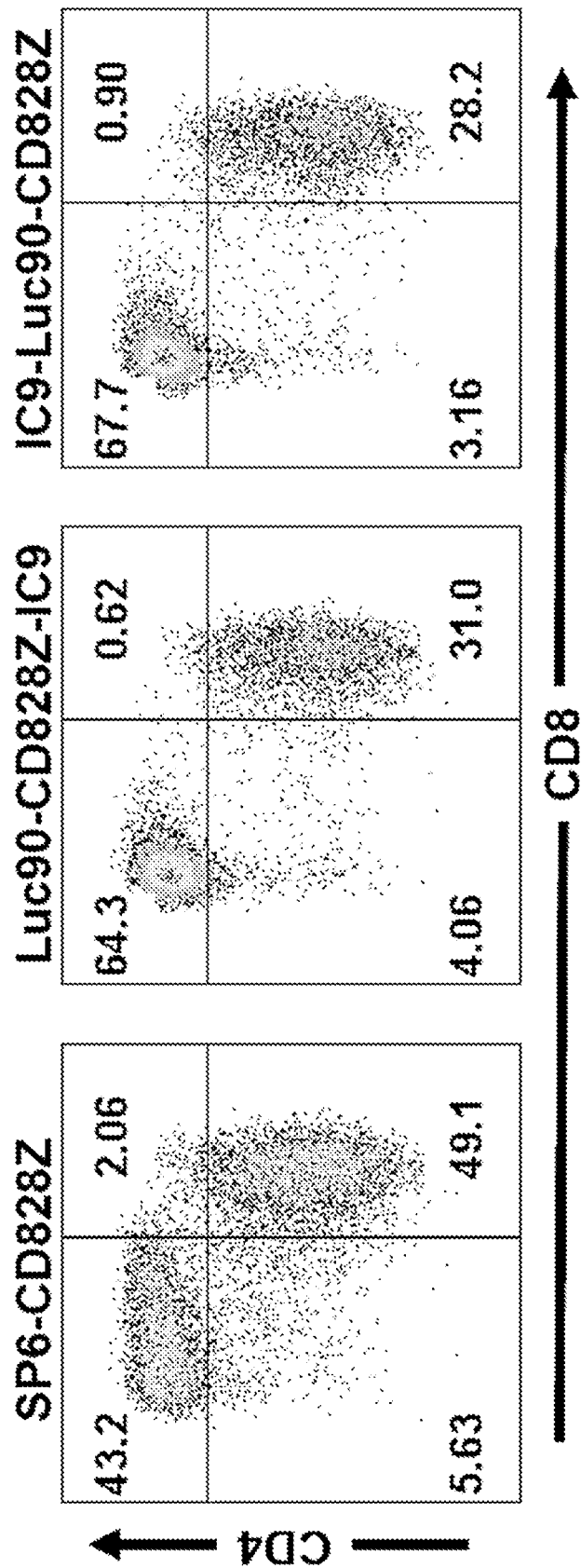

FIG. 10 is a set of plots illustrating CD4 and CD8 expression by anti-SLAMF7 CAR T cells. The CD4:CD8 ratio was increased in T-cell cultures expressing anti-SLAMF7 CARs compared with T-cell cultures transduced with CARs that do not target SLAMF7. The plots were gated on CD3+, live lymphocytes.

Figure 11A:
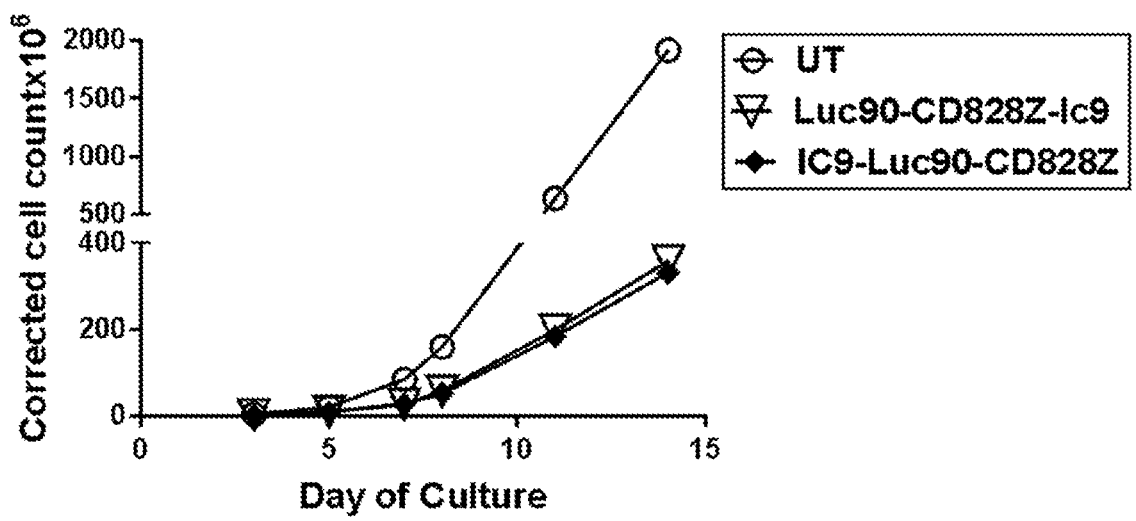
Figure 11B:
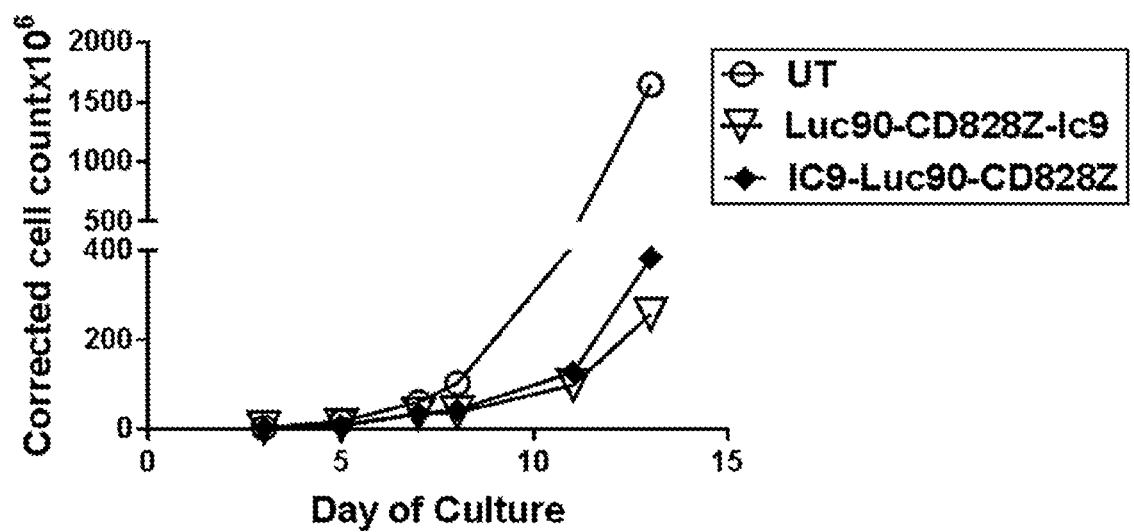

FIGS. 11A and 11B are graphs illustrating T cell accumulation in vitro. The T cells expressed either Luc90-CD828Z-IC9 (open triangles) or IC9-Luc90-CD828Z (closed diamonds). Day 0 was the day of culture initiation. FIG. 11A illustrates T cell accumulation when T cells were transduced with the indicated CARs on day 2 of culture. FIG. 11B illustrates T cell accumulation when T cells were transduced with the indicated CARs on day 2 and day 3 of culture. Untransduced (UT, open circles) T cells accumulated to a greater degree than CAR-transduced T cells.

Figure 12:
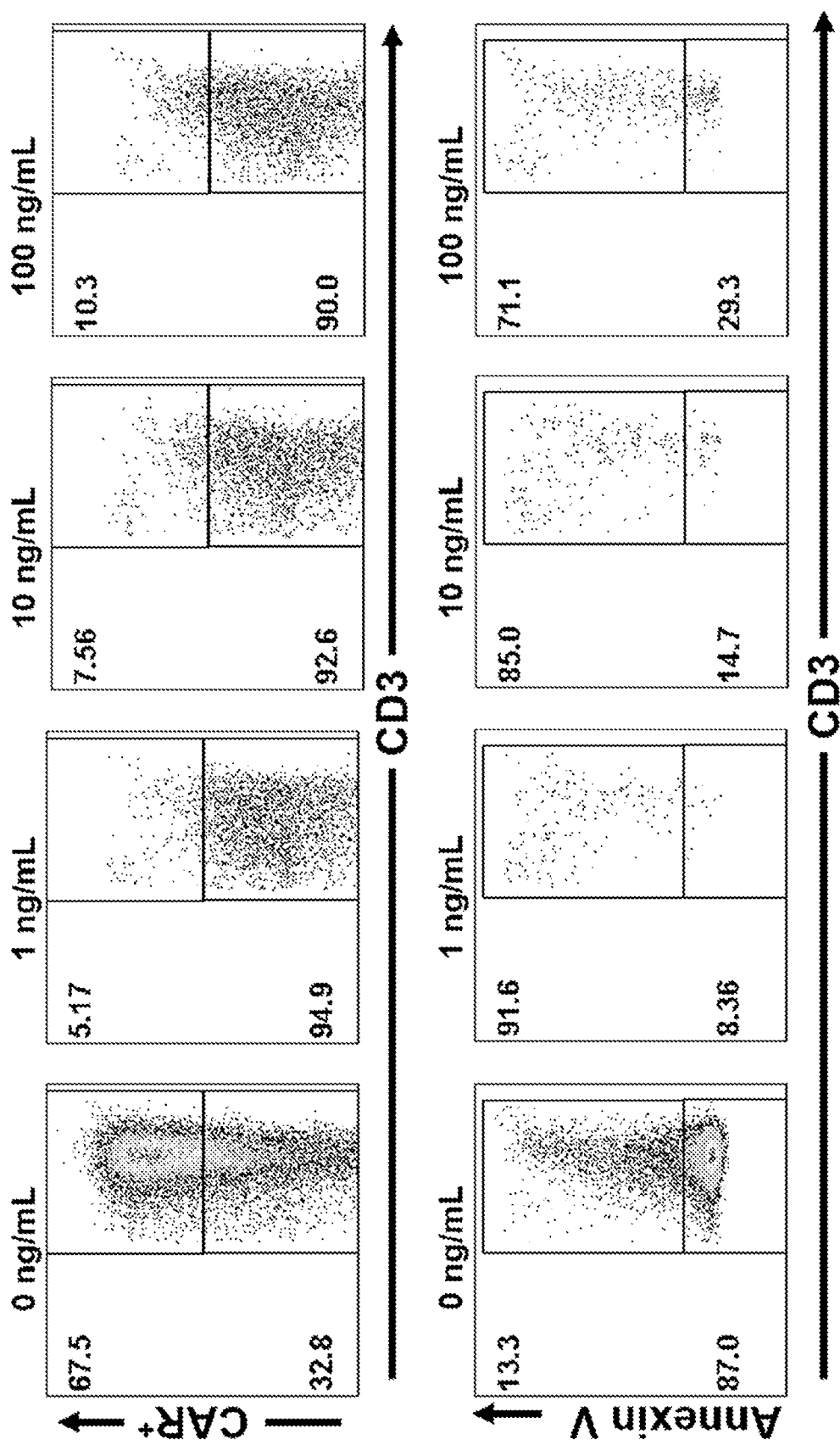

FIG. 12 is a set of plots illustrating that IC9-expressing T cells can be eliminated with AP1903 (rimiducid). On day 8 of culture (5 days after transduction), T cell transduced with Luc90-CD828Z-IC9 were exposed to the indicated concentrations of AP1903 for 6 hours. The plots on the upper row were gated on CD3+ live lymphocytes. These plots show that most transduced cells exposed to either 1, 10, or 100 ng/mL of AP1903 were eliminated. A culture with 0 ng/mL of AP1903 added was included for comparison. The plots on the bottom row are gated on CAR+, CD3+ live lymphocytes. These plots show that most residual CAR+ T cells in the AP1903-treated cultures were annexin V+, which indicates that they were apoptotic.

Figure 13:
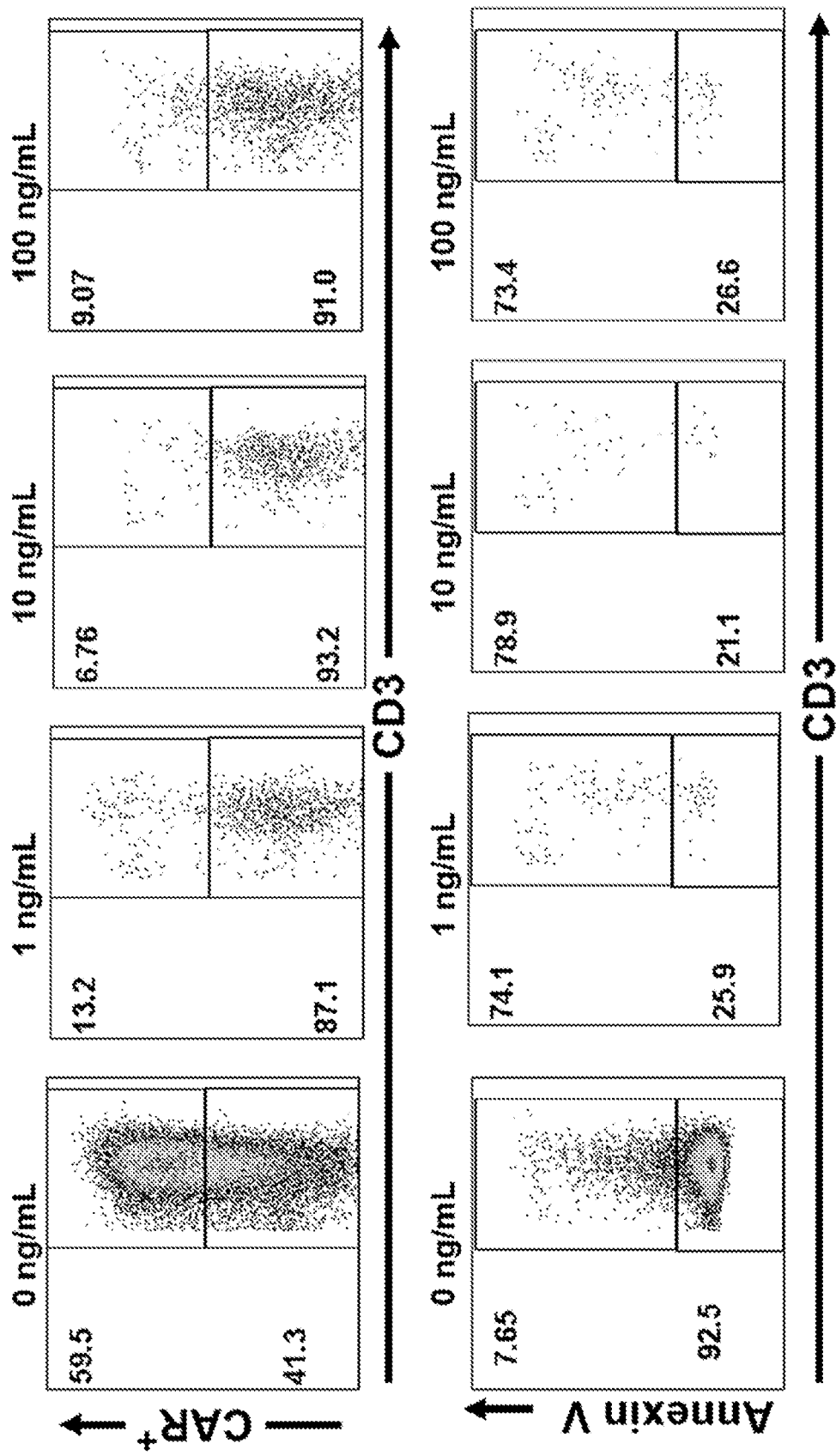

FIG. 13 is a set of plots illustrating that IC9-expressing T cells can be eliminated with AP1903. On day 8 of culture (5 days after transduction), T cell transduced with Luc90-CD828Z-IC9 were placed in culture with the indicated concentrations of AP1903 for 48 hours. Similar to the plots of T cells from the same donor shown in FIGS. 11A and 11B, these plots show that most transduced cells exposed to either 1, 10, or 100 ng/mL of AP1903 were eliminated and that most residual CAR+ cells were annexin V+. Gating was the same as FIGS. 11A and 11B.

Figure 14:
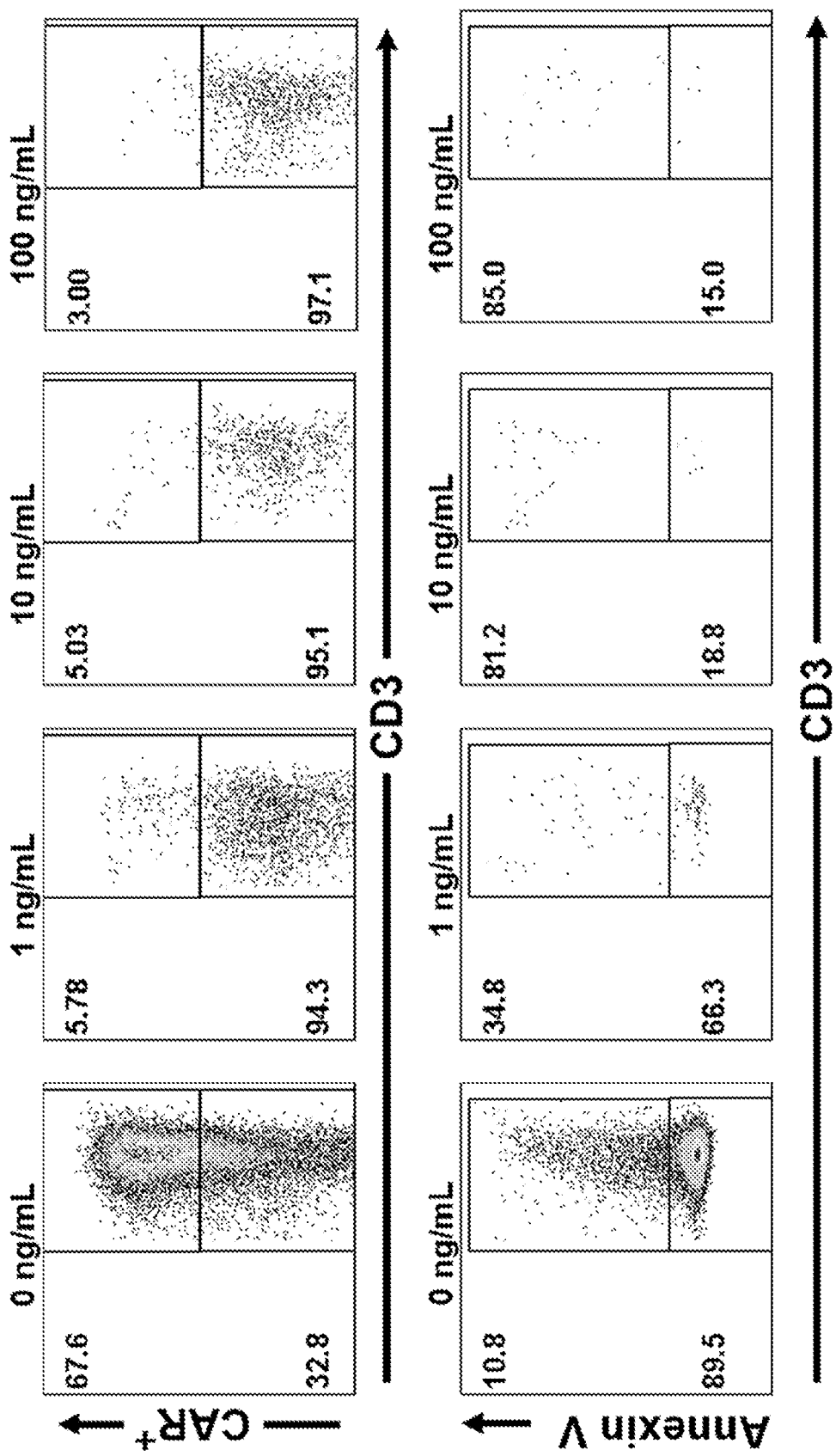

FIG. 14 is a set of plots illustrating that IC9-expressing T cells can be eliminated with AP1903. On day 8 of culture (5 days after transduction), T cell transduced with IC9-Luc90-CD828Z were exposed to the indicated concentrations of AP1903 for 6 hours. The plots on the upper row are gated on CD3+ live lymphocytes. These plots show that most transduced cells exposed to either 1, 10, or 100 ng/mL of AP1903 were eliminated. A culture with 0 ng/mL of AP1903 added was included for comparison. The plots on the bottom row are gated on CAR+, CD3+ live lymphocytes. These plots show that most residual CAR+ T cells in the AP1903-treated cultures were annexin V+, which indicates that they were apoptotic.

Figure 15:
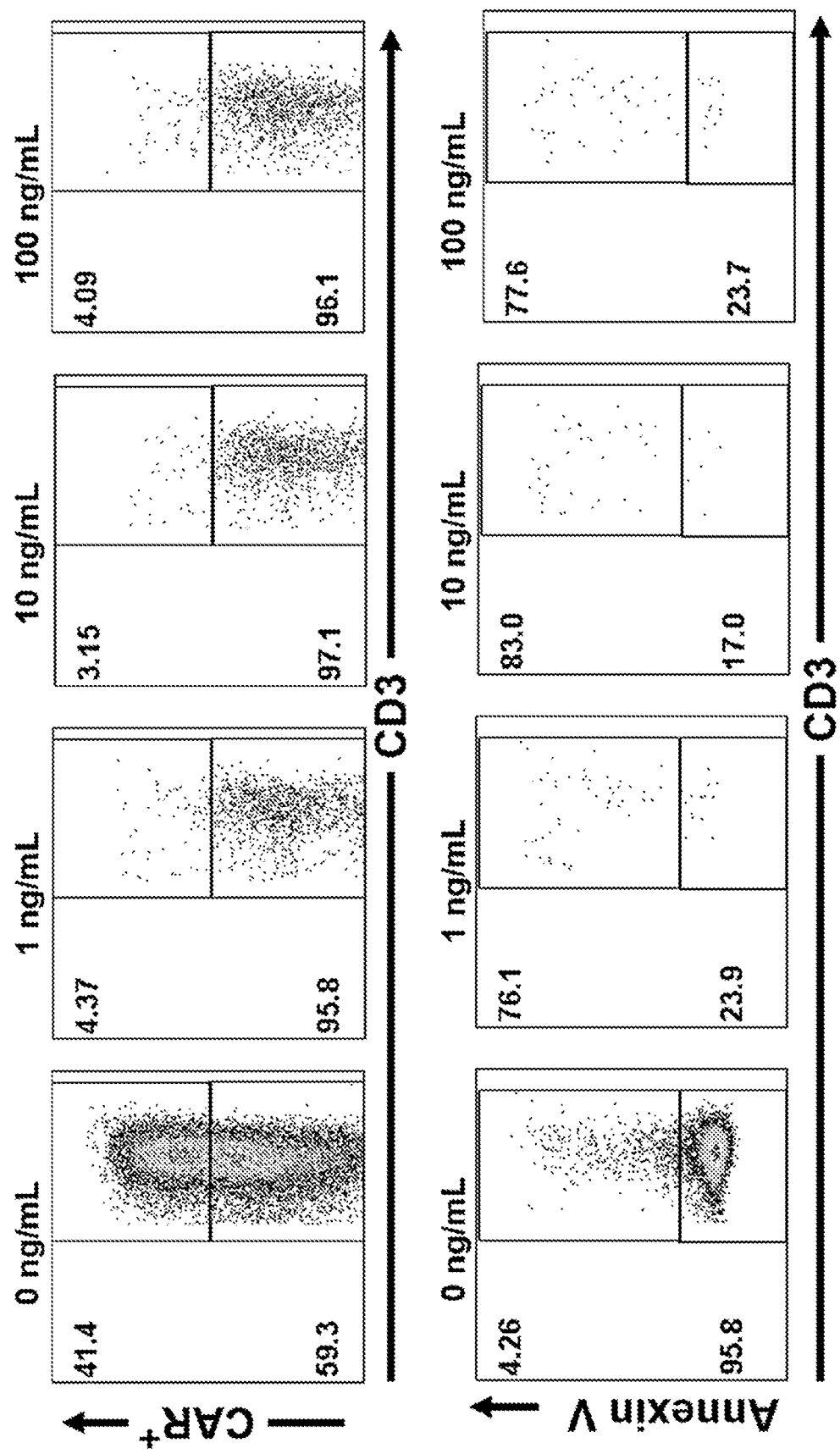

FIG. 15 is a set of plots illustrating that IC9-expressing T cells can be eliminated with AP1903. On day 8 of culture (5 days after transduction), T cell transduced with IC9-Luc90-CD828Z were placed in culture with the indicated concentrations of AP1903 for 48 hours. Similar to the plots of T cells from the same culture shown in FIG. 13, these plots show that most transduced cells exposed to either 1, 10, or 100 ng/mL of AP1903 were eliminated and that most residual CAR+ cells were annexin V+. Gating was the same as FIG. 13.

Figure 16A:
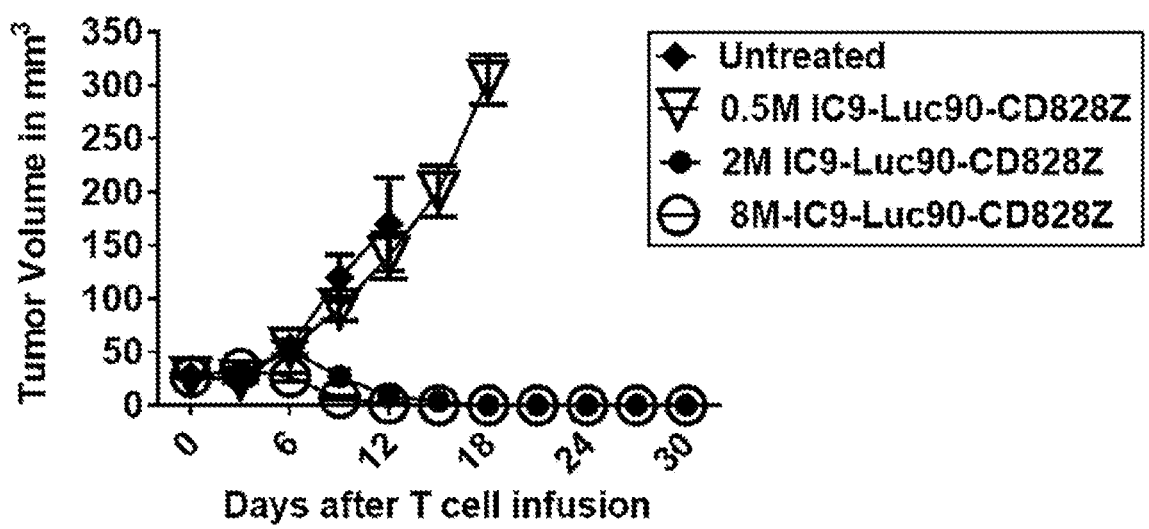
Figure 16B:
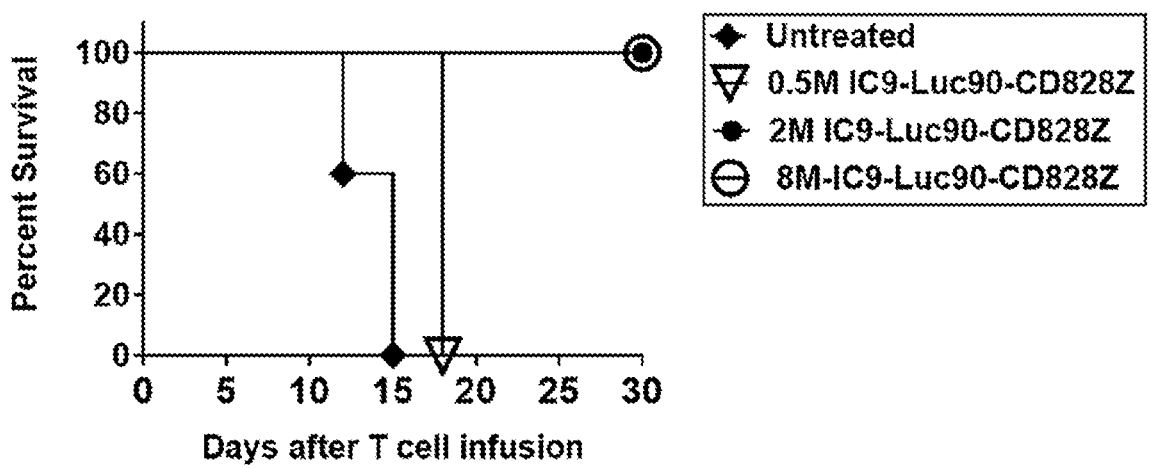

FIG. 16A and FIG. 16B are graphs showing results from a dose-titration of IC9-Luc90-CD828Z-expressing T cells. Immunocompromised NSG mice with MM.1S human SLAMF7+ multiple myeloma solid tumors were treated with a single infusion of 0.5×10⁶ (open triangle), 2×10⁶ (closed circle), or 8×10⁶ (open circle) IC9-Luc90-CD828Z-expressing T cells (untreated control—closed diamonds). FIG. 16A shows tumor volume and FIG. 16B shows survival rate.

Figure 17A:
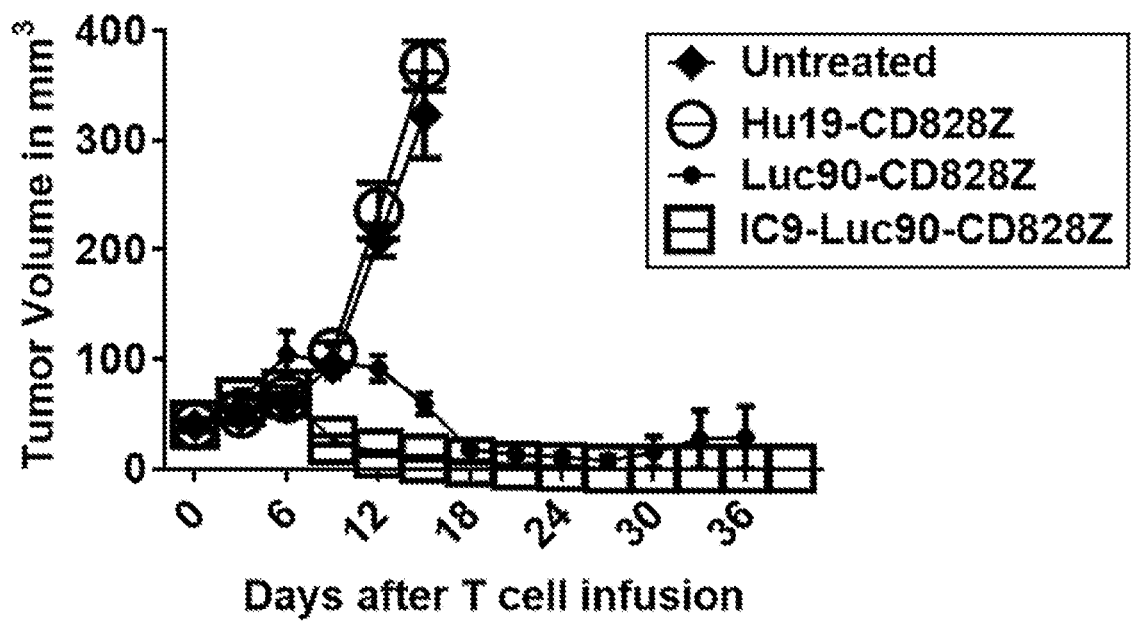
Figure 17B:
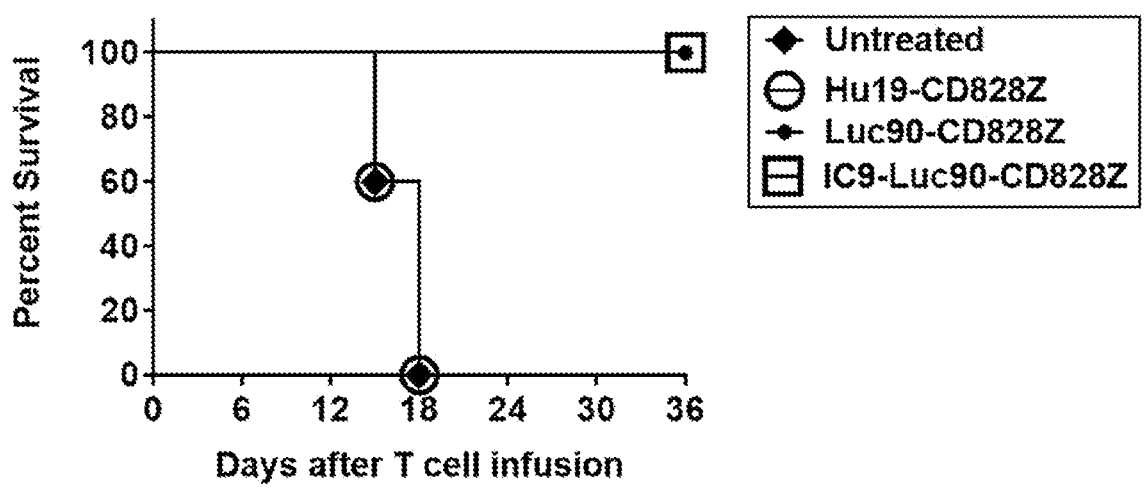

FIG. 17A and FIG. 17B are graphs showing results from immunocompromised NSG mice with MM.1S human SLAMF7+ multiple myeloma solid tumors treated with T cells expressing one of 3 different CARs: IC9-Luc90-CD828Z (suicide gene+anti-SLAMF7 CAR; open rectangle), Luc90-CD828Z (anti-SLAMF7 CAR alone; closed circle), or a negative-control anti-CD19 CAR Hu19-CD828Z (untreated control—closed diamond). The CAR+ T cell dose was 2 million CAR+ T cells per mouse. FIG. 17A shows tumor volume and FIG. 17B shows survival rate.

Figure 18:
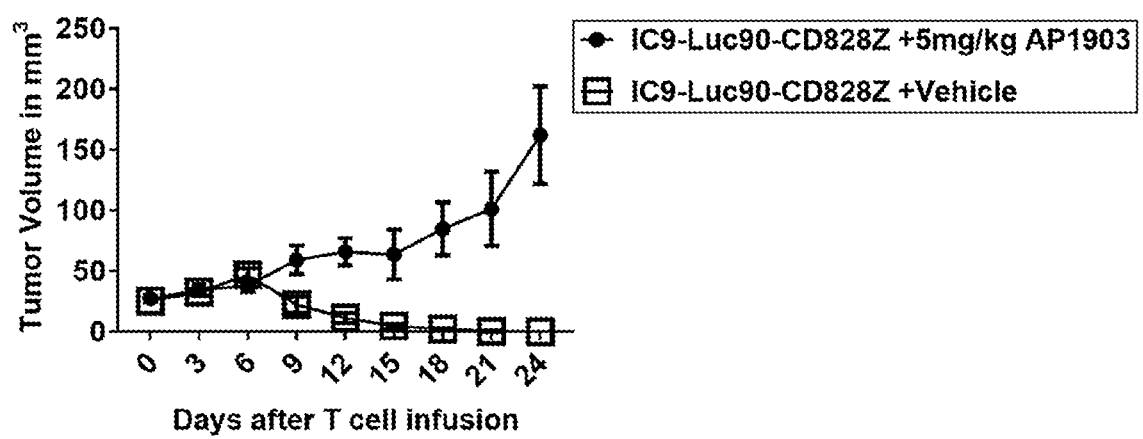

FIG. 18 is a graph showing results from immunocompromised NSG mice with MM.1S human SLAMF7+ multiple myeloma solid tumors treated with 2×10⁶ IC9-Luc90-CD828Z T cells. Mice were treated with 5 mg/kg of AP1903 intraperitoneally for 3 days and 12 days after the CAR T-cell infusion (closed circle) or with vehicle (open rectangle).

DETAILED DESCRIPTION OF THE INVENTION

An embodiment of the invention provides a CAR comprising an antigen recognition domain, a TM domain, and a T cell activation domain, wherein the CAR has antigenic specificity for SLAMF7. A CAR is an artificially constructed hybrid protein or polypeptide containing an antigen recognition domain of an antibody linked to T-cell signaling or T-cell activation domains. CARs have the ability to redirect T-cell specificity and reactivity toward a selected target in a non-MHC-restricted manner, exploiting the antigen-binding properties of monoclonal antibodies. The non-MHC-restricted antigen recognition gives T-cells expressing CARs the ability to recognize an antigen independent of antigen processing, thus bypassing a major mechanism of tumor escape. Moreover, when expressed in T-cells, CARs advantageously do not dimerize with endogenous T-cell receptor (TCR) alpha and beta chains.

The inventive CARs have antigenic specificity for SLAMF7. The phrases "has antigenic specificity" and "elicit antigen-specific response," as used herein, means that the CAR can specifically bind to and immunologically recognize an antigen, such that binding of the CAR to the antigen elicits an immune response.

SLAMF7 is also referred to as CD319 and CS1 (CD2 subset-1). SLAMF7 is highly expressed on the malignant plasma cells that constitute multiple myeloma (MM) as detected by gene expression, flow cytometry, and IHC. Many (about 80-about 100%) cases of MM uniformly express SLAMF7 (Wang et al., *Clin. Cancer Res.*, 24(1): 106-119 (2018); Tai et al., *Blood*, 112(4):1329-1337 (2008); Hsi et al., *Clin. Cancer Res.*, 14(9): 2775-2784 (2008); Mathur et al., *Blood*, 130(Suppl 1): 502-502 (2017)). Human SLAMF7 has the amino acid sequence of SEQ ID NO: 37.

The inventive anti-SLAMF7 CARs may provide any one or more of a variety of advantages. Although CAR T cells targeting B-cell maturation antigen (BCMA) may provide clinical activity against cancers such as, e.g., MM, the variable expression of BCMA on MM and/or the loss of BCMA expression after CAR T-cell infusion may limit the effectiveness of CAR T cells targeting BCMA. By targeting SLAMF7, the inventive CARs advantageously provide an alternative strategy for treating cancer, e.g., multiple myeloma. Moreover, SLAMF7 expression is absent from a wide variety of non-hematologic tissues. Accordingly, the inventive CARs may, advantageously, reduce or eliminate undesirable cross-reactivity with non-hematologic tissues.

While SLAMF7 is expressed on malignant plasma cells, SLAMF7 is also expressed on normal plasma cells and a variety of other normal leukocytes. For example, SLAMF7 is expressed on most natural killer (NK) cells, some $CD8^+$ T cells, a small fraction of $CD4^+$ T cells, NKT cells, some monocytes, and some dendritic cells. A CAR targeting SLAMF7 may reduce or eliminate normal SLAMF7-expressing leukocytes such as NK cells and dendritic cells, which could, undesirably, increase the risk of infections (e.g., herpes viral infections).

Accordingly, as discussed in more detail below, an embodiment of the invention provides anti-SLAMF7 CARs in combination with a regulatory element capable of modulating the anti-SLAMF7 activity of a host cell expressing the CAR. The regulatory element may regulate the anti-SLAMF7 activity of a host cell expressing the CAR. For example, the regulatory element may act as an "on" or "off" switch. The regulatory element may provide on-demand reduction or elimination of anti-SLAMF7 CAR-expressing cells. The combination of the regulatory element with the anti-SLAMF7 CAR may, advantageously, reduce or eliminate unacceptable toxicities caused by depletion of normal leukocytes after infusion of CAR-expressing cells targeting SLAMF7, e.g., chronic cytopenias. Alternatively or additionally, the regulatory element may reduce or eliminate other types of toxicity such as severe cytokine-release syndrome.

The CAR comprises an antigen recognition domain. The antigen recognition domain recognizes and binds to SLAMF7. The antigen binding domain of the CAR may comprise the antigen binding domain of an anti-SLAMF7 antibody.

The antigen binding domain may comprise any antigen binding portion of the anti-SLAMF7 antibody. For example, the antigen binding domain may be a Fab fragment (Fab), F(ab')2 fragment, diabody, triabody, tetrabody, single-chain variable region fragment (scFv), or a disulfide-stabilized variable region fragment (dsFv). In a preferred embodiment, the antigen binding domain is an scFv. An scFv is a truncated Fab fragment including the variable (V) domain of an antibody heavy chain linked to a V domain of an antibody light chain via a synthetic peptide, which can be generated using routine recombinant DNA technology techniques. The anti-SLAMF7 antigen binding domain employed in the inventive CARs, however, is not limited to these exemplary types of antibody fragments.

The antigen binding domain may comprise a light chain variable region and/or a heavy chain variable region. In an embodiment of the invention, the heavy chain variable region comprises a complementarity determining region (CDR) 1, a CDR2, and a CDR3. In a preferred embodiment, the antigen binding domain comprises a heavy chain CDR1, a heavy chain CDR2, and a heavy chain CDR3. In an embodiment of the invention, the light chain variable region may comprise a light chain CDR1, a light chain CDR2, and a light chain CDR3. In a preferred embodiment, the antigen binding domain comprises a light chain CDR1, a light chain CDR2, and a light chain CDR3.

An embodiment of the invention provides a CAR comprising the antigen binding domain of the murine Luc90 antibody ("Luc90"). The antigen binding domain of Luc90 specifically binds to SLAMF7. The Luc90 antibody is described in U.S. Patent Publication No. 2006/0024296.

The inventive CAR may comprise a Luc90 antigen binding domain comprising one or more of a heavy chain CDR1 comprising, consisting of, or consisting essentially of the amino acid sequence of SEQ ID NO: 1; a heavy chain CDR2 comprising, consisting of, or consisting essentially of the amino acid sequence of SEQ ID NO: 2; and a heavy chain CDR3 comprising, consisting of, or consisting essentially of the amino acid sequence of SEQ ID NO: 3. Preferably, the Luc90 heavy chain comprises all of the amino acid sequences of SEQ ID NOs: 1-3.

The inventive CAR may comprise a Luc90 antigen binding domain comprising one or more of a light chain CDR1 comprising, consisting of, or consisting essentially of the amino acid sequence of SEQ ID NO: 4; a light chain CDR2 comprising, consisting of, or consisting essentially of the amino acid sequence of SEQ ID NO: 5; and a light chain CDR3 comprising, consisting of, or consisting essentially of the amino acid sequence of SEQ ID NO: 6. Preferably, the Luc90 light chain comprises the amino acid sequences of all of SEQ ID NOs: 4-6. In an especially preferred embodiment, the Luc90 antigen binding domain comprises all of the amino acid sequences of SEQ ID NO: 1-6.

In an embodiment of the invention, the Luc90 antigen binding domain comprises a heavy chain variable region and a light chain variable region. The heavy chain variable region of the Luc90 antigen binding domain may comprise, consist of, or consist essentially of the amino acid sequence of SEQ ID NO: 13. The light chain variable region of the Luc90 antigen binding domain may comprise, consist of, or consist essentially of the amino acid sequence of SEQ ID NO: 14. Accordingly, in an embodiment of the invention, the Luc90 antigen binding domain comprises a heavy chain variable region comprising the amino acid sequence of SEQ ID NO: 13 and/or a light chain variable region comprising the amino acid sequence of SEQ ID NO: 14. Preferably, the Luc90 antigen binding domain comprises the amino acid sequences of both SEQ ID NOs: 13 and 14.

Another embodiment of the invention provides a CAR comprising the antigen binding domain of the humanized Luc63 antibody ("huLuc63"). The antigen binding domain of huLuc63 specifically binds to SLAMF7. The huLuc63 antibody is described in U.S. Patent Publication No. 2006/0024296.

The inventive CAR may comprise a huLuc63 antigen binding domain comprising one or more of a heavy chain CDR1 comprising, consisting of, or consisting essentially of the amino acid sequence of SEQ ID NO: 7; a heavy chain CDR2 comprising, consisting of, or consisting essentially of the amino acid sequence of SEQ ID NO: 8; and a heavy chain CDR3 comprising, consisting of, or consisting essentially of the amino acid sequence of SEQ ID NO: 9. Preferably, the huLuc63 heavy chain comprises all of the amino acid sequences of SEQ ID NOs: 7-9.

The inventive CAR may comprise a huLuc63antigen binding domain comprising one or more of a light chain CDR1 comprising, consisting of, or consisting essentially of the amino acid sequence of SEQ ID NO: 10; a light chain CDR2 comprising, consisting of, or consisting essentially of the amino acid sequence of SEQ ID NO: 11; and a light chain CDR3 comprising, consisting of, or consisting essentially of the amino acid sequence of SEQ ID NO: 12. Preferably, the huLuc63light chain comprises the amino acid sequences of all of SEQ ID NOs: 10-12. In an especially preferred embodiment, the huLuc63antigen binding domain comprises all of the amino acid sequences of SEQ ID NO: 7-12.

In an embodiment of the invention, the huLuc63antigen binding domain comprises a heavy chain variable region and a light chain variable region. The heavy chain variable region of the huLuc63antigen binding domain may comprise, consist of, or consist essentially of the amino acid sequence of SEQ ID NO: 15. The light chain variable region of the huLuc63antigen binding domain may comprise, consist of, or consist essentially of the amino acid sequence of SEQ ID NO: 16. Accordingly, in an embodiment of the invention, the huLuc63antigen binding domain comprises a heavy chain variable region comprising the amino acid sequence of SEQ ID NO: 15 and/or a light chain variable region comprising the amino acid sequence of SEQ ID NO: 16. Preferably, the huLuc63antigen binding domain comprises the amino acid sequences of both SEQ ID NOs: 15 and 16.

In an embodiment of the invention, the light chain variable region and the heavy chain variable region may be joined by an antigen recognition domain linker peptide. The antigen recognition domain linker peptide may be of any length and many comprise any amino acid sequence. For example, the antigen recognition domain linker peptide may comprise or consist of any one or more of glycine, serine, lysine, proline, glutamic acid, and threonine, with or without other amino acid residues. In an embodiment of the invention, the antigen recognition domain linker peptide may have a length of about 5 to about 100 amino acid residues, about 8 to about 75 amino acid residues, about 8 to about 50 amino acid residues, about 10 to about 25 amino acid residues, about 8 to about 30 amino acid residues, about 8 to about 40 amino acid residues, or about 8 to about 50 amino acid residues. In an embodiment of the invention, the antigen recognition domain linker peptide may comprise, consist, or consist essentially of, SEQ ID NO: 17. While the antigen binding domain may have a sequence from N-terminus to C-terminus of heavy-chain variable domain, linker, light-chain variable domain, in a preferred embodiment, the antigen binding domain has a sequence from N-terminus to C-terminus of light-chain variable domain, linker, heavy-chain variable domain.

In another embodiment, the CAR comprises a signal sequence (also referred to as a leader sequence). The signal sequence may be positioned at the amino terminus of the antigen recognition domain (e.g., the light chain variable region of the anti-SLAMF7 antibody). The signal sequence may be a human signal sequence. The signal sequence may comprise any suitable amino acid sequence. In one embodiment, the signal sequence is a human granulocyte-macrophage colony-stimulating factor (GM-CSF) receptor signal sequence or a human CD8a signal sequence. For example, the antigen binding domain may comprise a signal sequence comprising, consisting of, or consisting essentially of SEQ ID NO: 22. In an embodiment of the invention, while the signal sequence may facilitate expression of the CAR on the surface of the cell, the presence of the signal sequence in an expressed CAR may not be necessary in order for the CAR to function. In an embodiment of the invention, upon expression of the CAR on the cell surface, all or a portion of the signal sequence may be cleaved off of the CAR. Accordingly, in an embodiment of the invention, the CAR lacks a leader sequence.

In an embodiment of the invention, the CAR comprises a hinge domain. One of ordinary skill in the art will appreciate that a hinge domain is a short sequence of amino acids that facilitates antibody flexibility (see, e.g., Woof et al., *Nat. Rev. Immunol.*, 4(2): 89-99 (2004)). The hinge domain may be positioned between the antigen recognition domain and the TM domain domain. Preferably, the hinge domain is a human hinge domain. The hinge domain may comprise the hinge domain of human CD8α or human CD28.

The CAR may comprise a TM domain. The TM domain can be any TM domain derived or obtained from any molecule known in the art. Preferably, the TM domain is a human TM domain. For example, the TM domain may comprise the TM domain of a human CD8α molecule or a human CD28 molecule. CD8 is a TM glycoprotein that serves as a co-receptor for the TCR, and is expressed primarily on the surface of cytotoxic T-cells. The most common form of CD8 exists as a dimer composed of a CD8α and CD8β chain. CD28 is expressed on T-cells and provides co-stimulatory signals for T-cell activation. CD28 is the receptor for CD80 (B7.1) and CD86 (B7.2). In an embodiment of the invention, the CAR comprises the amino acid sequence of SEQ ID NO: 18 (the hinge domain and TM domain of human CD8α).

The CAR may comprise a T cell activation domain. The T cell activation domain may comprise an intracellular (i.e., cytoplasmic) T-cell signaling domain. The intracellular T-cell signaling domain can be obtained or derived from a CD28 molecule, a CD3 zeta (ζ) molecule, an Fc receptor gamma (FcRγ) chain, a CD27 molecule, an OX40 molecule, a 4-1BB molecule, an inducible T-cell costimulatory protein (ICOS), or other intracellular signaling molecules known in the art, or modified versions of any of the foregoing. As discussed above, CD28 is a T-cell marker which is involved in T-cell co-stimulation. The intracellular T cell signaling domain of human CD28 may comprise, consist, or consist essentially of the amino acid sequence of SEQ ID NO: 19. CD3 associates with TCRs to produce a signal and contains immunoreceptor tyrosine-based activation motifs (ITAMs). The intracellular T cell signaling domain of human CD3 may comprise, consist, or consist essentially of the amino acid sequence of SEQ ID NO: 20. 4-1BB, also known as CD137, transmits a potent costimulatory signal to T-cells, promoting differentiation and enhancing long-term survival of T lymphocytes. The intracellular T cell signaling domain of human 4-1BB may comprise, consist, or consist essentially of the amino acid sequence of SEQ ID NO: 21. ICOS is a CD28-superfamily costimulatory molecule that is expressed on activated T cells. In a preferred embodiment, the CD28, CD3 zeta (ζ), FcRγ, ICOS, 4-1BB, OX40, and CD27 are human.

The inventive CAR can comprise any one of aforementioned TM domains and any one or more of the aforementioned intracellular T-cell signaling domains in any combination. For example, the inventive CAR may comprise a CD8a hinge and TM domain and intracellular T-cell signaling domains of CD28 and CD3. Alternatively, for example, the inventive CAR may comprise a CD8a hinge and TM domain and intracellular T-cell signaling domains of 4-1BB and CD3.

In one embodiment, the inventive CAR comprises, from the amino terminus to the carboxyl terminus, the CD8a signal sequence, anti-SLAMF7 scFv, human CD8a hinge and transmembrane domain, the cytoplasmic portion of human CD28, and the cytoplasmic portion of the human CD3 molecule.

In another embodiment, the inventive CAR comprises, from the amino terminus to the carboxyl terminus, the CD8a signal sequence, anti-SLAMF7 scFv, human CD8a hinge and transmembrane domain, the cytoplasmic portion of human 4-1BB, and the cytoplasmic portion of the human CD3 molecule.

In an embodiment of the invention, the CAR does not comprise any one or more of a Myc tag, an IgG4-Fc spacer, or an IgG4-Fc spacer which has been modified to prevent binding of an Fc receptor. For example, the CAR may lack all of the foregoing moieties. Accordingly, an embodiment of the invention provides a CAR comprising an antigen recognition domain, a TM domain, and a T cell activation domain, wherein the CAR has antigenic specificity for SLAMF7, wherein the CAR does not comprise any of a Myc tag, an IgG4-Fc spacer, or an IgG4-Fc spacer which has been modified to prevent binding of an Fc receptor. One of ordinary skill in the art can determine whether an IgG4-Fc spacer has been modified to prevent binding of an Fc receptor using assays known in the art.

Additional embodiments of the invention provide CARs comprising, consisting of, or consisting essentially of the amino acid sequence of any one of SEQ ID NOs: 27-31. In some embodiments, the CAR is provided in combination with a suicide gene, as explained in more detail below. The components of the CARs of SEQ ID NOs: 27-31 are set forth in Tables 1-2 below.

TABLE 1

| CAR (SEQ ID NO:) | Antigen Recognition Domain | Hinge and TM Domain | T Cell Activation Domain |
|---|---|---|---|
| Luc90-CD828Z (SEQ ID NO: 27) | Luc90 heavy chain (SEQ ID NO: 13) Luc90 light chain (SEQ ID NO: 14) | Human CD8a | Human CD28 Human CD3ζ |
| HuLuc63-CD828Z | huLuc63 heavy chain (SEQ ID NO: 15) | Human CD8a | Human CD28 Human CD3ζ |

TABLE 1-continued

| CAR (SEQ ID NO:) | Antigen Recognition Domain | Hinge and TM Domain | T Cell Activation Domain |
|---|---|---|---|
| (SEQ ID NO: 28) | huLuc63 light chain (SEQ ID NO: 16) | | |
| Luc90-CD8BBZ (SEQ ID NO: 29) | Luc90 heavy chain (SEQ ID NO: 13) Luc90 light chain (SEQ ID NO: 14) | Human CD8a | Human 4-1BB Human CD3ζ |

TABLE 2

| CAR (SEQ ID NO:) | Antigen Recognition Domain | Hinge and TM Domain | T Cell Activation Domain | Cleavable linker | Suicide Gene |
|---|---|---|---|---|---|
| Luc90-CD828Z-IC9 (SEQ ID NO: 30) | Luc90 heavy chain (SEQ ID NO: 13) Luc90 light chain (SEQ ID NO: 14) | Human CD8a | Human CD28 Human CD3ζ | T2A | IC9 |
| IC9-Luc90-CD828Z (SEQ ID NO: 31) | Luc90 heavy chain (SEQ ID NO: 13) Luc90 light chain (SEQ ID NO: 14) | Human CD8a | Human CD28 Human CD3ζ | T2A | IC9 |

Included in the scope of the invention are functional portions of the inventive CARs described herein. The term "functional portion" when used in reference to a CAR refers to any part or fragment of the CAR of the invention, which part or fragment retains the biological activity of the CAR of which it is a part (the parent CAR). Functional portions encompass, for example, those parts of a CAR that retain the ability to recognize target cells, or detect, treat, or prevent a disease, to a similar extent, the same extent, or to a higher extent, as the parent CAR. In reference to the parent CAR, the functional portion can comprise, for instance, about 10%, about 25%, about 30%, about 50%, about 60%, about 70%, about 80%, about 90%, about 95%, or more, of the parent CAR.

The functional portion can comprise additional amino acids at the amino or carboxy terminus of the portion, or at both termini, which additional amino acids are not found in the amino acid sequence of the parent CAR. Desirably, the additional amino acids do not interfere with the biological function of the functional portion, e.g., recognize target cells, detect cancer, treat or prevent cancer, etc. More desirably, the additional amino acids enhance the biological activity, as compared to the biological activity of the parent CAR.

Included in the scope of the invention are functional variants of the inventive CARs described herein. The term "functional variant" as used herein refers to a CAR, polypeptide, or protein having substantial or significant sequence identity or similarity to a parent CAR, which functional variant retains the biological activity of the CAR of which it is a variant. Functional variants encompass, for example, those variants of the CAR described herein (the parent CAR) that retain the ability to recognize target cells to a similar extent, the same extent, or to a higher extent, as the parent CAR. In reference to the parent CAR, the functional variant can, for instance, be at least about 30%, about 50%, about 75%, about 80%, about 90%, about 98% or more identical in amino acid sequence to the parent CAR.

A functional variant can, for example, comprise the amino acid sequence of the parent CAR with at least one conservative amino acid substitution. Alternatively or additionally, the functional variants can comprise the amino acid sequence of the parent CAR with at least one non-conservative amino acid substitution. In this case, it is preferable for the non-conservative amino acid substitution to not interfere with or inhibit the biological activity of the functional variant. The non-conservative amino acid substitution may enhance the biological activity of the functional variant, such that the biological activity of the functional variant is increased as compared to the parent CAR.

Amino acid substitutions of the inventive CARs are preferably conservative amino acid substitutions. Conservative amino acid substitutions are known in the art, and include amino acid substitutions in which one amino acid having certain physical and/or chemical properties is exchanged for another amino acid that has the same or similar chemical or physical properties. For instance, the conservative amino acid substitution can be an acidic/negatively charged polar amino acid substituted for another acidic/negatively charged polar amino acid (e.g., Asp or Glu), an amino acid with a nonpolar side chain substituted for another amino acid with a nonpolar side chain (e.g., Ala, Gly, Val, Ile, Leu, Met, Phe, Pro, Trp, Cys, Val, etc.), a basic/positively charged polar amino acid substituted for another basic/positively charged polar amino acid (e.g. Lys, His, Arg, etc.), an uncharged amino acid with a polar side chain substituted for another uncharged amino acid with a polar side chain (e.g., Asn, Gln, Ser, Thr, Tyr, etc.), an amino acid with a beta-branched side-chain substituted for another amino acid with a beta-branched side-chain (e.g., Ile, Thr, and Val), an amino acid with an aromatic side-chain substituted for another amino acid with an aromatic side chain (e.g., His, Phe, Trp, and Tyr), etc.

The CAR can consist essentially of the specified amino acid sequence or sequences described herein, such that other components, e.g., other amino acids, do not materially change the biological activity of the functional variant.

The CARs of embodiments of the invention (including functional portions and functional variants) can be of any length, i.e., can comprise any number of amino acids, provided that the CARs (or functional portions or functional variants thereof) retain their biological activity, e.g., the ability to specifically bind to antigen, detect diseased cells in a mammal, or treat or prevent disease in a mammal, etc. For example, the CAR can be about 50 to about 1000 amino acids long, such as about 50, about 70, about 75, about 100, about 125, about 150, about 175, about 200, about 300, about 400, about 500, about 600, about 700, about 800, about 900, about 1,000 or more amino acids in length.

The CARs of embodiments of the invention (including functional portions and functional variants of the invention) can comprise synthetic amino acids in place of one or more naturally-occurring amino acids. Such synthetic amino acids are known in the art, and include, for example, aminocyclohexane carboxylic acid, norleucine, α-amino n-decanoic acid, homoserine, S-acetylaminomethyl-cysteine, trans-3- and trans-4-hydroxyproline, 4-aminophenylalanine, 4-nitrophenylalanine, 4-chlorophenylalanine, 4-carboxyphenylalanine, β-phenylserine β-hydroxyphenylalanine, phenylglycine, α-naphthylalanine, cyclohexylalanine, cyclohexylglycine, indoline-2-carboxylic acid, 1,2,3,4-tetrahydroisoquinoline-3-carboxylic acid, aminomalonic acid, aminomalonic acid monoamide, N'-benzyl-N'-methyl-lysine, N',N'-dibenzyl-lysine, 6-hydroxylysine, ornithine, α-aminocyclopentane carboxylic acid, α-aminocyclohexane carboxylic acid, α-aminocycloheptane carboxylic acid, α-(2-amino-2-norbornane)-carboxylic acid, α,γ-diaminobutyric acid, α,β-diaminopropionic acid, homophenylalanine, and α-tert-butylglycine.

The CARs of embodiments of the invention (including functional portions and functional variants) can be glycosylated, amidated, carboxylated, phosphorylated, esterified, N-acylated, cyclized via, e.g., a disulfide bridge, or converted into an acid addition salt and/or optionally dimerized or polymerized, or conjugated.

The CARs of embodiments of the invention (including functional portions and functional variants thereof) can be obtained by methods known in the art. The CARs may be made by any suitable method of making polypeptides or proteins. For example, CARs can be recombinantly produced using the nucleic acids described herein using standard recombinant methods. See, for instance, Green and Sambrook, *Molecular Cloning: A Laboratory Manual*, 4$^{th}$ ed., Cold Spring Harbor Press, Cold Spring Harbor, N.Y. 2012. Alternatively, the CARs described herein (including functional portions and functional variants thereof) can be commercially synthesized by companies, such as Synpep (Dublin, Calif.), Peptide Technologies Corp. (Gaithersburg, Md.), and Multiple Peptide Systems (San Diego, Calif.). In this respect, the inventive CARs can be synthetic, recombinant, isolated, and/or purified.

Further provided by an embodiment of the invention is a nucleic acid comprising a nucleotide sequence encoding any of the CARs described herein (including functional portions and functional variants thereof). The nucleic acids of the invention may comprise a nucleotide sequence encoding any of the leader domains, hinge domains, antigen recognition domains, TM domains, and T cell activation domains described herein. Accordingly, an embodiment of the invention provides a nucleic acid comprising a nucleotide sequence encoding a CAR, wherein the CAR comprises an antigen recognition domain, a TM domain, and a T cell activation domain, and wherein the CAR has antigenic specificity for SLAMF7.

As discussed above, in embodiments of the invention, the CAR may be provided in combination with a regulatory element capable of modulating the anti-SLAMF7 activity of a host cell expressing the CAR. The regulatory element may regulate the anti-SLAMF7 activity of a host cell expressing the CAR. Accordingly, an embodiment of the invention provides a system comprising: (a) a nucleotide sequence encoding a CAR, wherein the CAR comprises an antigen recognition domain, a TM domain, and a T cell activation domain, and wherein the CAR has antigenic specificity for SLAMF7; and (b) a regulatory element capable of modulating the anti-SLAMF7 activity of a host cell expressing the CAR. The regulatory element may regulate the anti-SLAMF7 activity of a host cell expressing the CAR. For example, the regulatory element may act as an "on" or "off" switch.

In an embodiment of the invention, the regulatory element downregulates the anti-SLAMF7 activity of the host cell expressing the CAR. For example, the regulatory element kills the host cell expressing the CAR. In this regard, the regulatory element is a suicide gene, as described in more detail below. In an embodiment of the invention, the regulatory element is an inducible dimerization kill switch. An example of an inducible dimerization kill switch is the IC9 suicide gene, discussed in more detail below. Another example of an inducible dimerization kill switch is an element which provides for small-molecule-induced dimerization of the intracellular signaling domain of Fas, which induces apoptosis via a caspase-8-dependent pathway. This approach may be used to induce apoptosis using a small molecule made by fusing two molecules of the drug calcineurin (Spencer et al., *Curr. Biol.,* 6: 839-47 (1996); Belshaw et al., *Chem. Biol.,* 3: 731-38 (1996)) or the FKBP/AP1903 dimerizer system described herein (Thomis et al., *Blood,* 97: 1249-57 (2001)).

In an embodiment of the invention, the regulatory element is a cell surface marker. The cell surface marker may be co-expressed with the CAR. Administration of an antibody targeting the cell surface marker may reduce or eliminate the CAR-expressing host cells. Such cell surface markers may be useful as a safety mechanism to deplete CAR-positive cells in vivo. In vivo depletion may occur by one or both of complement-mediated lysis of opsonized cells and antibody-mediated cell-dependent cytotoxicity. For example, cells transduced with a cell surface marker which is a CD8-α stalk with two rituximab (anti-CD20) mimotopes can be depleted with rituximab (Philip et al., *Blood,* 124: 1277-87 (2014)). Other examples of cell surface markers which may be targeted for depletion by an antibody include CD20 (Griffioen et al., *Haematologica,* 94: 1316-20 (2009)), c-myc epitope tag (Kieback et al., *PNAS,* 105: 623-28 (2008)), and truncated versions of the human epidermal growth factor receptor. The truncated epidermal growth factor receptor may lack one or both of the ligand-binding and intracellular signaling domains but retain the epitope for cetuximab binding (Wang et al., *Blood,* 118: 1255-63 (2011)).

The regulatory element may be an inhibitory receptor. For example, antigen-specific inhibitory chimeric antigen receptors (iCARs) may preemptively constrain T cell responses. Such iCARs may selectively limit cytokine secretion, cytotoxicity, and proliferation induced through the endogenous T cell receptor or an activating chimeric receptor (Fedorov et al., *Sci. Transl. Med.,* 5:215ra172 (2013)).

In an embodiment of the invention, the regulatory element upregulates the anti-SLAMF7 activity of the host cell. In this regard, the regulatory element may act as an "on" switch to control expression or activity of the CAR to occur where and when it is needed.

For example, the regulatory element may be an element which confers dependence on small-molecule ligands for cell survival or activity. An example of such an element may be a drug-responsive, ribozyme-based regulatory device linked to growth cytokine targets to control cell (e.g., T cell) proliferation (Chen et al., *PNAS,* 107(19): 8531-6 (2010)). Another example may be to design the antigen-binding and intracellular signaling components of the CAR to assemble only in the presence of a heterodimerizing small molecule (Wu et al., *Science,* 350(6258):aab4077 (2015)).

Other potential regulatory elements may include elements which control the location of transgene integration (Schumann et al., *PNAS,* 112(33): 10437-42 (2015)) or a genetic deletion which produces an auxotrophic cell (e.g., T cell).

In another embodiment of the invention, the nucleotide sequence encoding the CAR is RNA. Introducing CAR mRNA into cells may result in transient expression of the CAR. With this approach, the mRNA may persist for a few days, but there may be an antitumor effect with minimal on-target toxicity (Beatty et al., *Cancer Immunol. Res.,* 2(2): 112-20 (2014)).

In an embodiment of the invention, the CAR is provided in combination with a suicide gene. The product of the suicide gene may, advantageously, provide on-demand reduction or elimination of anti-SLAMF7 CAR-expressing cells. Accordingly, an embodiment of the invention provides a nucleic acid comprising: (a) a suicide gene; and (b) a nucleotide sequence encoding a CAR, wherein the CAR comprises an antigen recognition domain, a TM domain, and a T cell activation domain, and wherein the CAR has antigenic specificity for SLAMF7. The CAR encoded by the nucleic acid may be as described herein with respect to other aspects of the invention.

As used herein, the term "suicide gene" refers to a gene that causes the cell expressing the suicide gene to die. The suicide gene can be a gene that confers sensitivity to an agent, e.g., a drug, upon the cell in which the gene is expressed, and causes the cell to die when the cell is contacted with or exposed to the agent. Suicide genes are known in the art and include, for example, the Herpes Simplex Virus (HSV) thymidine kinase (TK) gene, cytosine daminase, inducible caspase 9 (IC9) gene, purine nucleoside phosphorylase, and nitroreductase.

In a preferred embodiment, the suicide gene is the IC9 gene. The product of the IC9 gene contains part of the proapoptotic protein human caspase 9 ("caspase 9 component") fused to a binding domain derived from human FK-506 binding protein ("FKBP12 component"). Activation of the caspase 9 domain of IC9 is dependent on dimerization of IC9 proteins that occurs when a small molecule drug, rimiducid (AP1903), binds to the FKBP12 moiety of IC9. After caspase 9 is activated, the cells carrying the IC9 gene undergo apoptosis. The FKBP12 component encoded by the IC9 gene may comprise, consist, or consist essentially of the amino acid sequence of the amino acid sequence of SEQ ID NO: 24. The caspase 9 component encoded by the IC9 gene may comprise, consist, or consist essentially of the amino acid sequence of SEQ ID NO: 25.

In an embodiment of the invention, the nucleic acid encodes the FKBP12 component joined to the caspase 9 component by a IC9 linker peptide. The IC9 linker peptide may be of any length and many comprise any amino acid sequence. For example, the IC9 linker peptide may comprise or consist of any one or both of glycine and serine, with or without other amino acid residues. In an embodiment of the invention, the IC9 linker peptide may have a length of about 3 to about 10 amino acid residues, about 3 to about 20 amino acid residues, about 4 to about 6 amino acid residues, or about 5 amino acid residues. In an embodiment of the invention, the IC9 linker peptide may comprise, consist, or consist essentially of, SEQ ID NO: 26 (SGGGS). The IC9 gene product may have a sequence from N-terminus to C-terminus of caspase 9 component, IC9 linker peptide, FKBP12 component. In a preferred embodiment, the IC9 gene product has a sequence from N-terminus to C-terminus of FKBP12 component, IC9 linker peptide, caspase 9 component (SEQ ID NO: 38).

In an embodiment of the invention, the nucleic acid further comprises a nucleotide sequence encoding a cleavable linker sequence. The nucleotide sequence encoding the cleavable linker sequence may be positioned between the nucleotide sequence encoding the CAR and the regulatory element, e.g., suicide gene. In this regard, the amino acid sequence encoded by the inventive nucleic acids may be cleaved such that two proteins are produced: a first protein encoded the nucleotide sequence encoding the CAR and a second protein encoded by the regulatory element, e.g., suicide gene.

Accordingly, an embodiment of the invention provides protein(s) encoded by the inventive nucleic acids. A combination of first and second proteins may be encoded by the nucleotide sequence of the inventive nucleic acids which include a cleavable linker as described herein. In an embodiment of the invention, the first protein is encoded by the nucleotide sequence encoding the CAR, and the second protein is encoded by the suicide gene. The CAR and the suicide gene may be as described herein with respect to other aspects of the invention. In an embodiment of the invention, the first protein (encoding the CAR) comprises the amino acid sequence of any one of SEQ ID NO: 27-29 and the second protein (encoded by the suicide gene) comprises the amino acid sequence of SEQ ID NO: 38.

In an embodiment, the cleavable linker sequence comprises a "self-cleaving" 2A peptide. "Self-cleaving" 2A peptides are described, for example, in Liu et al., *Sci. Rep.,* 7(1): 2193 (2017) and Szymczak et al., *Nature Biotechnol.,* 22(5): 589-594 (2004). 2A peptides are viral oligopeptides that mediate cleavage of polypeptides during translation in eukaryotic cells. The designation "2A" refers to a specific region of the viral genome. Without being bound to a particular theory or mechanism, it is believed that the mechanism of 2A-mediated "self-cleavage" is ribosome skipping of the formation of a glycyl-prolyl peptide bond at the C-terminus of the 2A peptide. Different 2A peptides may comprise, at the C-terminus, the consensus amino acid sequence of GDVEX$_1$NPGP (SEQ ID NO: 39), wherein X$_1$ of SEQ ID NO: 39 is any naturally occurring amino acid residue. In an embodiment of the invention, the cleavable linker sequence is a porcine teschovirus-1 2A (P2A) amino acid sequence, equine rhinitis A virus (E2A) amino acid sequence, thosea asigna virus 2A (T2A) amino acid sequence, or foot-and-mouth disease virus (F2A) amino acid sequence. In an embodiment of the invention, the cleavable linker sequence is a 2A peptide amino acid sequence comprising, consisting, or consisting essentially of, the amino acid sequence of ASRAEGRGSLLTCGDVEENPGP (T2A) (SEQ ID NO: 23).

In an embodiment, the cleavable linker sequence comprises a furin-cleavable sequence. Exemplary furin cleavage sequences are described in Duckert et al., *Protein Engineering, Design & Selection,* 17(1): 107-112 (2004) and U.S. Pat. No. 8,871,906, each of which is incorporated herein by reference. In an embodiment of the invention, the furin-cleavable sequence is represented by the formula P4-P3-P2-P1 (Formula I), wherein P4 is an amino acid residue at the amino end, P1 is an amino acid residue at the carboxyl end, P1 is an arginine or a lysine residue, and the sequence is cleavable at the carboxyl end of P1 by furin. In another embodiment of the invention, the furin-cleavable sequence of Formula I (i) further comprises amino acid residues represented by P6-P5 at the amino end, (ii) further comprises amino acid residues represented by P1'-P2' at the carboxyl end, (iii) wherein if P1 is an arginine or a lysine residue, P2' is tryptophan, and P4 is arginine, valine or lysine, provided that if P4 is not arginine, then P6 and P2 are basic residues, and (iv) the sequence is cleavable at the carboxyl end of P1 by furin. In an embodiment of the invention, the furin cleavage sequence comprises R-X$_1$-X$_2$-R, wherein X$_1$ is any naturally occurring amino acid and X$_2$ is arginine or lysine (SEQ ID NO: 40).

The nucleotide sequence encoding the CAR may be positioned 5' of the suicide gene, with the nucleotide sequence encoding the cleavable linker sequence positioned between the nucleotide sequence encoding the CAR and the suicide gene. An example of a nucleotide sequence with such a structure is the nucleotide sequence which encodes Luc90-CD828Z-IC9 (SEQ ID NO: 30).

Alternatively, the nucleotide sequence encoding the CAR may be positioned 3' of the suicide gene, with the nucleotide sequence encoding the cleavable linker sequence positioned between the nucleotide sequence encoding the CAR and the suicide gene. An example of a nucleotide sequence with such a structure is the nucleotide sequence which encodes IC9-Luc90-CD828Z (SEQ ID NO: 31).

In an embodiment of the invention, the nucleotide sequence encodes the amino acid sequence of any one of SEQ ID NOs: 27-31. SEQ ID NOs: 27-31 are described above in Tables 1-2.

In an embodiment of the invention, the nucleic acid may comprise, consist of, or consist essentially of the nucleotide sequence of any one of SEQ ID NO: 32 (Luc90-CD828Z), SEQ ID NO: 33 (HuLuc63-CD828Z), SEQ ID NO: 34 (Luc90-CD8BBZ), SEQ ID NO: 35 (Luc90-CD828Z-IC9), and SEQ ID NO: 36 (IC9-Luc90-CD828Z).

"Nucleic acid" as used herein includes "polynucleotide," "oligonucleotide," and "nucleic acid molecule," and generally means a polymer of DNA or RNA, which can be single-stranded or double-stranded, synthesized or obtained (e.g., isolated and/or purified) from natural sources, which can contain natural, non-natural or altered nucleotides, and which can contain a natural, non-natural or altered internucleotide linkage, such as a phosphoroamidate linkage or a phosphorothioate linkage, instead of the phosphodiester found between the nucleotides of an unmodified oligonucleotide. In some embodiments, the nucleic acid does not comprise any insertions, deletions, inversions, and/or substitutions. However, it may be suitable in some instances, as discussed herein, for the nucleic acid to comprise one or more insertions, deletions, inversions, and/or substitutions.

The nucleic acids of an embodiment of the invention may be recombinant. As used herein, the term "recombinant" refers to (i) molecules that are constructed outside living cells by joining natural or synthetic nucleic acid segments to nucleic acid molecules that can replicate in a living cell, or (ii) molecules that result from the replication of those described in (i) above. For purposes herein, the replication can be in vitro replication or in vivo replication.

A recombinant nucleic acid may be one that has a sequence that is not naturally occurring or has a sequence that is made by an artificial combination of two otherwise separated segments of sequence. This artificial combination is often accomplished by chemical synthesis or, more commonly, by the artificial manipulation of isolated segments of nucleic acids, e.g., by genetic engineering techniques, such as those described in Green and Sambrook, supra. The nucleic acids can be constructed based on chemical synthesis and/or enzymatic ligation reactions using procedures known in the art. See, for example, Green and Sambrook, supra. For example, a nucleic acid can be chemically synthesized using naturally occurring nucleotides or variously modified nucleotides designed to increase the biological stability of the molecules or to increase the physical stability of the duplex formed upon hybridization (e.g., phosphorothioate derivatives and acridine substituted nucleotides). Examples of modified nucleotides that can be used to generate the nucleic acids include, but are not limited to, 5-fluorouracil, 5-bromouracil, 5-chlorouracil, 5-iodouracil, hypoxanthine, xanthine, 4-acetylcytosine, 5-(carboxyhydroxymethyl) uracil, 5-carboxymethylaminomethyl-2-thiouridine, 5-carboxymethylaminomethyluracil, dihydrouracil, beta-D-galactosylqueosine, inosine, N$^6$-isopentenyladenine, 1-methylguanine, 1-methylinosine, 2,2-dimethylguanine, 2-methyladenine, 2-methylguanine, 3-methylcytosine, 5-methylcytosine, N$^6$-substituted adenine, 7-methylguanine, 5-methylaminomethyluracil, 5-methoxyaminomethyl-2-thiouracil, beta-D-mannosylqueosine, 5'-methoxycarboxymethyluracil, 5-methoxyuracil, 2-methylthio-N$^6$-isopentenyladenine, uracil-5-oxyacetic acid (v), wybutoxosine, pseudouracil, queosine, 2-thiocytosine, 5-methyl-2-thiouracil, 2-thiouracil, 4-thiouracil, 5-methyluracil, uracil-5-oxyacetic acid methylester, 3-(3-amino-3-N-2-carboxypropyl) uracil, and 2,6-diaminopurine. Alternatively, one or more of the nucleic acids of the invention can be purchased from companies, such as Macromolecular Resources (Fort Collins, Colo.) and Synthegen (Houston, Tex.).

The nucleic acid can comprise any isolated or purified nucleotide sequence which encodes any of the CARs or functional portions or functional variants thereof (alone or in combination with a suicide gene). Alternatively, the nucleotide sequence can comprise a nucleotide sequence which is degenerate to any of the sequences or a combination of degenerate sequences.

An embodiment of the invention also provides an isolated or purified nucleic acid comprising a nucleotide sequence which is complementary to the nucleotide sequence of any of the nucleic acids described herein or a nucleotide sequence which hybridizes under stringent conditions to the nucleotide sequence of any of the nucleic acids described herein.

The nucleotide sequence which hybridizes under stringent conditions may hybridize under high stringency conditions. By "high stringency conditions" is meant that the nucleotide sequence specifically hybridizes to a target sequence (the nucleotide sequence of any of the nucleic acids described herein) in an amount that is detectably stronger than non-specific hybridization. High stringency conditions include conditions which would distinguish a polynucleotide with an exact complementary sequence, or one containing only a few scattered mismatches from a random sequence that happened to have a few small regions (e.g., 3-10 bases) that matched the nucleotide sequence. Such small regions of complementarity are more easily melted than a full-length complement of 14-17 or more bases, and high stringency hybridization makes them easily distinguishable. Relatively high stringency conditions would include, for example, low salt and/or high temperature conditions, such as provided by about 0.02-0.1 M NaCl or the equivalent, at temperatures of about 50-70° C. Such high stringency conditions tolerate little, if any, mismatch between the nucleotide sequence and the template or target strand, and are particularly suitable for detecting expression of any of the inventive CARs (alone or in combination with a suicide gene). It is generally appreciated that conditions can be rendered more stringent by the addition of increasing amounts of formamide.

The invention also provides a nucleic acid comprising a nucleotide sequence that is at least about 70% or more, e.g., about 80%, about 90%, about 91%, about 92%, about 93%, about 94%, about 95%, about 96%, about 97%, about 98%, or about 99% identical to any of the nucleic acids described herein.

In an embodiment, the nucleic acids of the invention can be incorporated into a recombinant expression vector. In this regard, an embodiment of the invention provides recombinant expression vectors comprising any of the nucleic acids of the invention. For purposes herein, the term "recombinant expression vector" means a genetically-modified oligonucleotide or polynucleotide construct that permits the expression of an mRNA, protein, polypeptide, or peptide by a host cell, when the construct comprises a nucleotide sequence encoding the mRNA, protein, polypeptide, or peptide, and the vector is contacted with the cell under conditions sufficient to have the mRNA, protein, polypeptide, or peptide expressed within the cell. The vectors of the invention are not naturally-occurring as a whole. However, parts of the vectors can be naturally-occurring. The inventive recombinant expression vectors can comprise any type of nucleotides, including, but not limited to DNA and RNA, which can be single-stranded or double-stranded, synthesized or obtained in part from natural sources, and which can contain natural, non-natural or altered nucleotides. The recombinant expression vectors can comprise naturally-occurring or non-naturally-occurring internucleotide linkages, or both types of linkages. Preferably, the non-naturally occurring or altered nucleotides or internucleotide linkages do not hinder the transcription or replication of the vector.

In an embodiment, the recombinant expression vector of the invention can be any suitable recombinant expression vector, and can be used to transform or transfect any suitable host cell. Suitable vectors include those designed for propagation and expansion or for expression or both, such as plasmids and viruses. The vector can be selected from the group consisting of the pUC series (Fermentas Life Sciences, Glen Burnie, Md.), the pBluescript series (Stratagene, LaJolla, Calif.), the pET series (Novagen, Madison, Wis.), the pGEX series (Pharmacia Biotech, Uppsala, Sweden), and the pEX series (Clontech, Palo Alto, Calif.). Bacteriophage vectors, such as λGT10, λGT11, λZapII (Stratagene), λEMBL4, and λNM1149, also can be used. Examples of plant expression vectors include pBI01, pBI101.2, pBI101.3, pBI121 and pBIN19 (Clontech). Examples of animal expression vectors include pEUK-Cl, pMAM, and pMAMneo (Clontech). The recombinant expression vector may be a viral vector, e.g., a retroviral vector (e.g., a gammaretroviral vector) or a lentiviral vector.

In an embodiment, the recombinant expression vectors of the invention can be prepared using standard recombinant DNA techniques described in, for example, Sambrook and Green, supra. Constructs of expression vectors, which are circular or linear, can be prepared to contain a replication system functional in a prokaryotic or eukaryotic host cell. Replication systems can be derived, e.g., from ColEl, 2μ plasmid, λ, SV40, bovine papilloma virus, and the like.

The recombinant expression vector may comprise regulatory sequences, such as transcription and translation initiation and termination codons, which are specific to the type of host cell (e.g., bacterium, fungus, plant, or animal) into which the vector is to be introduced, as appropriate, and taking into consideration whether the vector is DNA- or RNA-based. The recombinant expression vector may comprise restriction sites to facilitate cloning. In addition to the inventive nucleic acid sequence encoding the CAR (alone or in combination with a suicide gene), the recombinant expression vector preferably comprises expression control sequences, such as promoters, enhancers, polyadenylation signals, transcription terminators, internal ribosome entry sites (IRES), and the like, that provide for the expression of the nucleic acid sequence in a host cell.

The recombinant expression vector can include one or more marker genes, which allow for selection of transformed or transfected host cells. Marker genes include biocide resistance, e.g., resistance to antibiotics, heavy metals, etc., complementation in an auxotrophic host to provide prototrophy, and the like. Suitable marker genes for the inventive expression vectors include, for instance, neomycin/G418 resistance genes, hygromycin resistance genes, histidinol resistance genes, tetracycline resistance genes, and ampicillin resistance genes.

The recombinant expression vector can comprise a native or nonnative promoter operably linked to the nucleotide sequence encoding the CAR (including functional portions and functional variants thereof) (alone or in combination with a suicide gene), or to the nucleotide sequence which is complementary to or which hybridizes to the nucleotide sequence encoding the CAR (alone or in combination with a suicide gene). The selection of promoters, e.g., strong, weak, inducible, tissue-specific and developmental-specific, is within the ordinary skill of the artisan. Similarly, the combining of a nucleotide sequence with a promoter is also within the skill of the artisan. The promoter can be a non-viral promoter or a viral promoter, e.g., a cytomegalovirus (CMV) promoter, an SV40 promoter, an RSV promoter, or a promoter found in the long-terminal repeat of the murine stem cell virus.

The inventive recombinant expression vectors can be designed for either transient expression, for stable expression, or for both. Also, the recombinant expression vectors can be made for constitutive expression or for inducible expression.

An embodiment of the invention further provides a host cell comprising any of the recombinant expression vectors described herein. As used herein, the term "host cell" refers to any type of cell that can contain the inventive recombinant expression vector. The host cell can be a eukaryotic cell, e.g., plant, animal, fungi, or algae, or can be a prokaryotic cell, e.g., bacteria or protozoa. The host cell can be a cultured cell or a primary cell, i.e., isolated directly from an organism, e.g., a human. The host cell can be an adherent cell or a suspended cell, i.e., a cell that grows in suspension. Suitable host cells are known in the art and include, for instance, DH5a *E. coli* cells, Chinese hamster ovarian cells, monkey VERO cells, COS cells, HEK293 cells, and the like. For purposes of amplifying or replicating the recombinant expression vector, the host cell may be a prokaryotic cell, e.g., a DH5a cell. For purposes of producing a recombinant CAR, the host cell may be a mammalian cell. The host cell may be a human cell. The host cell can be of any cell type, can originate from any type of tissue, and can be of any developmental stage. The host cell may be a peripheral blood lymphocyte (PBL) or a peripheral blood mononuclear cell (PBMC).

In an embodiment of the invention, the host cell is a T cell. For purposes herein, the T cell can be any T cell, such as a cultured T cell, e.g., a primary T cell, or a T cell from a cultured T cell line, e.g., Jurkat, SupT1, etc., or a T cell obtained from a mammal. If obtained from a mammal, the T cell can be obtained from numerous sources, including but not limited to blood, bone marrow, lymph node, the thymus, or other tissues or fluids. T cells can also be enriched for or purified. The T cell may be a human T cell. The T cell may be a T cell isolated from a human. The T cell can be any type of T cell and can be of any developmental stage, including but not limited to, $CD4^+/CD8^+$ double positive T cells, $CD4^+$ helper T cells, e.g., $Th_1$ and Thz cells, $CD8^+$ T cells (e.g., cytotoxic T cells), tumor infiltrating cells, memory T cells, naïve T cells, and the like. The T cell may be a $CD8^+$ T cell or a $CD4^+$ T cell.

In an embodiment of the invention, the host cell is a natural killer (NK) cell. NK cells are a type of cytotoxic lymphocyte that plays a role in the innate immune system. NK cells are defined as large granular lymphocytes and constitute the third kind of cells differentiated from the common lymphoid progenitor which also gives rise to B and T lymphocytes (see, e.g., *Immunobiology*, $9^{th}$ ed., Janeway et al., eds., Garland Publishing, New York, N.Y. (2016)). NK cells differentiate and mature in the bone marrow, lymph node, spleen, tonsils, and thymus. Following maturation, NK cells enter into the circulation as large lymphocytes with distinctive cytotoxic granules. NK cells are able to recognize and kill some abnormal cells, such as, for example, some tumor cells and virus-infected cells, and are thought to be important in the innate immune defense against intracellular pathogens. As described above with respect to T-cells, the NK cell can be any NK cell, such as a cultured NK cell, e.g., a primary NK cell, or an NK cell from a cultured NK cell line, or an NK cell obtained from a mammal. If obtained from a mammal, the NK cell can be obtained from numerous sources, including but not limited to blood, bone marrow, lymph node, the thymus, or other tissues or fluids. NK cells can also be enriched for or purified. The NK cell preferably is a human NK cell (e.g., isolated from a human). NK cell lines are available from, e.g., the American Type Culture Collection (ATCC, Manassas, Va.) and include, for example, NK-92 cells (ATCC CRL-2407), NK92MI cells (ATCC CRL-2408), and derivatives thereof.

Also provided by an embodiment of the invention is a population of cells comprising at least one host cell described herein. The population of cells can be a heterogeneous population comprising the host cell comprising any of the recombinant expression vectors described, in addition to at least one other cell, e.g., a host cell (e.g., a T cell), which does not comprise any of the recombinant expression vectors, or a cell other than a T cell, e.g., a B cell, a macrophage, a neutrophil, an erythrocyte, a hepatocyte, an endothelial cell, an epithelial cell, a muscle cell, a brain cell, etc. Alternatively, the population of cells can be a substantially homogeneous population, in which the population comprises mainly host cells (e.g., consisting essentially of) comprising the recombinant expression vector. The population also can be a clonal population of cells, in which all cells of the population are clones of a single host cell comprising a recombinant expression vector, such that all cells of the population comprise the recombinant expression vector. In one embodiment of the invention, the population of cells is a clonal population comprising host cells comprising a recombinant expression vector as described herein.

The inventive recombinant expression vectors encoding a CAR may be introduced into a cell by "transfection," "transformation," or "transduction." "Transfection," "transformation," or "transduction," as used herein, refer to the introduction of one or more exogenous polynucleotides into a host cell by using physical or chemical methods. Many transfection techniques are known in the art and include, for example, calcium phosphate DNA co-precipitation; DEAE-dextran; electroporation; cationic liposome-mediated transfection; tungsten particle-facilitated microparticle bombardment; and strontium phosphate DNA co-precipitation. Phage or viral vectors can be introduced into host cells, after growth of infectious particles in suitable packaging cells, many of which are commercially available.

Included in the scope of the invention are conjugates, e.g., bioconjugates, comprising any of the inventive CARs (including any of the functional portions or variants thereof), nucleic acids, recombinant expression vectors, host cells, or populations of host cells. Conjugates, as well as methods of synthesizing conjugates in general, are known in the art.

CARs (including functional portions and variants thereof) (alone or in combination with a suicide gene product), nucleic acids, systems, protein(s) and combination(s) of proteins encoded by the nucleic acids, recombinant expression vectors, and host cells (including populations thereof), all of which are collectively referred to as "inventive CAR materials" hereinafter, can be isolated and/or purified. The term "isolated" as used herein means having been removed from its natural environment. The term "purified" or "isolated" does not require absolute purity or isolation; rather, it is intended as a relative term. Thus, for example, a purified (or isolated) host cell preparation is one in which the host cell is more pure than cells in their natural environment within the body. Such host cells may be produced, for example, by standard purification techniques. In some embodiments, a preparation of a host cell is purified such that the host cell represents at least about 50%, for example at least about 70%, of the total cell content of the preparation. For example, the purity can be at least about 50%, can be greater than about 60%, about 70% or about 80%, or can be about 100%.

The inventive CAR materials can be formulated into a composition, such as a pharmaceutical composition. In this regard, an embodiment of the invention provides a pharmaceutical composition comprising any of the inventive CAR materials and a pharmaceutically acceptable carrier. The inventive pharmaceutical compositions containing any of the inventive CAR materials can comprise more than one inventive CAR material, e.g., a CAR and a nucleic acid, or two or more different CARs. Alternatively, the pharmaceutical composition can comprise an inventive CAR material in combination with other pharmaceutically active agents or drugs, such as chemotherapeutic agents, e.g., asparaginase, busulfan, carboplatin, cisplatin, daunorubicin, doxorubicin, fluorouracil, gemcitabine, hydroxyurea, methotrexate, paclitaxel, rituximab, vinblastine, vincristine, etc. In a preferred embodiment, the pharmaceutical composition comprises the inventive host cell or populations thereof.

Preferably, the carrier is a pharmaceutically acceptable carrier. With respect to pharmaceutical compositions, the carrier can be any of those conventionally used for the particular inventive CAR material under consideration. Such pharmaceutically acceptable carriers are well-known to those skilled in the art and are readily available to the public. It is preferred that the pharmaceutically acceptable carrier be one which has no detrimental side effects or toxicity under the conditions of use.

The choice of carrier will be determined in part by the particular inventive CAR material, as well as by the particular method used to administer the inventive CAR material. In a preferred embodiment, the CAR is expressed by a host cell, which is preferably a T cell or an NK cell, and host cells expressing the CAR are administered to a patient. These cells could be autologous or allogeneic in relation to the recipient of the cells. A nucleic acid encoding the CAR may be introduced to the cells by any of a variety of methods of genetic modification including, but not limited to, transduction with a gamma-retrovirus, a lentivirus, or a transposon system. There are a variety of suitable formulations of the pharmaceutical composition of the invention. Suitable formulations may include any of those forparenteral, subcutaneous, intravenous, intramuscular, intratumoral, intraarterial, intrathecal, or interperitoneal administration. More than one route can be used to administer the inventive CAR materials, and in certain instances, a particular route can provide a more immediate and more effective response than another route.

Preferably, the inventive CAR material is administered by injection, e.g., intravenously. When the inventive CAR material is a host cell expressing the inventive CAR (or functional variant thereof), the pharmaceutically acceptable carrier for the cells for injection may include any isotonic carrier such as, for example, normal saline (about 0.90% w/v of NaCl in water, about 300 mOsm/L NaCl in water, or about 9.0 g NaCl per liter of water), NORMOSOL R electrolyte solution (Abbott, Chicago, Ill.), PLASMA-LYTE A (Baxter, Deerfield, Ill.), about 5% dextrose in water, or Ringer's lactate. In an embodiment, the pharmaceutically acceptable carrier is supplemented with human serum albumen.

The composition can employ time-released, delayed release, and sustained release delivery systems such that the delivery of the inventive composition occurs prior to, and with sufficient time to cause, sensitization of the site to be treated. Many types of release delivery systems are available and known to those of ordinary skill in the art. Such systems can avoid repeated administrations of the composition, thereby increasing convenience to the subject and the physician, and may be particularly suitable for certain composition embodiments of the invention.

Without being bound to a particular theory or mechanism, it is believed that by eliciting an antigen-specific response against SLAMF7, the inventive CARs provide for one or more of the following: targeting and destroying SLAMF7-expressing cancer cells, reducing or eliminating cancer cells, facilitating infiltration of immune cells to tumor site(s), and enhancing/extending anti-cancer responses.

It is contemplated that the inventive CARs materials can be used in methods of treating or preventing a disease, e.g., cancer, in a mammal. Without being bound to a particular theory or mechanism, the inventive CARs have biological activity, e.g., ability to recognize antigen, e.g., SLAMF7, such that the CAR when expressed by a cell is able to mediate an immune response against the cell expressing the antigen, e.g., SLAMF7, for which the CAR is specific. In this regard, an embodiment of the invention provides a method of treating or preventing cancer in a mammal, comprising administering to the mammal any of the CARs (including functional portions and variants thereof) (alone or in combination with a suicide gene product), nucleic acids, systems, protein(s) (including combination(s) of proteins) encoded by the nucleic acids, recombinant expression vectors, host cells (including populations thereof) and/or pharmaceutical compositions of the invention in an amount effective to treat or prevent cancer in the mammal. In a preferred embodiment, the method comprises infusing the mammal with host cells transduced with the inventive CAR.

One or more isolated host cells expressing the inventive SLAMF7 CAR described herein can be contacted with a population of cancer cells that express SLAMF7 ex vivo, in vivo, or in vitro. "Ex vivo" refers to methods conducted within or on cells or tissue in an artificial environment outside an organism with minimum alteration of natural conditions. In contrast, the term "in vivo" refers to a method that is conducted within living organisms in their normal, intact state, while an "in vitro" method is conducted using components of an organism that have been isolated from its usual biological context. The inventive method preferably involves ex vivo and in vivo components. In this regard, for example, the isolated host cells described above can be cultured ex vivo under conditions to express the inventive anti-SLAMF7 CAR, and then directly transferred into a mammal (preferably a human) affected by a SLAMF7-positive cancer, e.g., multiple myeloma. Such a cell transfer method is referred to in the art as "adoptive cell transfer (ACT)," in which immune-derived cells are transferred into a recipient to transfer the functionality of the immune-derived cells to the host. The immune-derived cells may have originated from the recipient or from another individual. Adoptive cell transfer methods may be used to treat various types of cancers, including hematological cancers such as myeloma.

Once the composition comprising host cells expressing the inventive CAR-encoding nucleic acid sequence, or a vector comprising the inventive CAR-encoding nucleic acid sequence, is administered to a mammal (e.g., a human), the biological activity of the CAR can be measured by any suitable method known in the art. In accordance with the inventive method, the CAR binds to SLAMF7 on the cancer, and the cancer cells are destroyed. Binding of the CAR to SLAMF7 on the surface of cancer cells can be assayed using any suitable method known in the art, including, for example, ELISA and flow cytometry. The ability of the CAR to destroy cells can be measured using any suitable method known in the art, such as cytotoxicity assays described in, for example, Kochenderfer et al., *J. Immunotherapy,* 32(7): 689-702 (2009), and Herman et al. *J. Immunological Methods,* 285(1): 25-40 (2004). The biological activity of the CAR also can be measured by assaying expression of certain cytokines, such as CD107a, IFNγ, IL-2, and TNF.

An embodiment of the invention further comprises lymphodepleting the mammal prior to administering the inventive CAR material. Examples of lymphodepletion include, but may not be limited to, nonmyeloablative lymphodepleting chemotherapy, myeloablative lymphodepleting chemotherapy, total body irradiation, etc.

For purposes of the inventive methods, wherein host cells or populations of cells are administered, the cells can be cells that are allogeneic or autologous to the mammal. Preferably, the cells are autologous to the mammal.

An "effective amount" or "an amount effective to treat" refers to a dose that is adequate to prevent or treat cancer in an individual. Amounts effective for a therapeutic or prophylactic use will depend on, for example, the stage and severity of the disease or disorder being treated, the age, weight, and general state of health of the patient, and the judgment of the prescribing physician. The size of the dose will also be determined by the particular CAR material selected, method of administration, timing and frequency of administration, the existence, nature, and extent of any adverse side-effects that might accompany the administration of a particular CAR material, and the desired physiological effect. It will be appreciated by one of skill in the art that various diseases or disorders (e.g., cancer) could require prolonged treatment involving multiple administrations, perhaps using the inventive CAR materials in each or various rounds of administration. By way of example and not intending to limit the invention, the dose of the inventive CAR material can be about 0.001 to about 1000 mg/kg body weight of the subject being treated/day, from about 0.01 to about 10 mg/kg body weight/day, about 0.01 mg to about 1 mg/kg body weight/day. In an embodiment of the invention, the dose may be from about $1\times10^4$ to about $1\times10^{10}$ cells expressing the inventive CAR per kg body weight. When the inventive CAR material is a host cell, an exemplary dose of host cells may be a minimum of one million cells (1 million cells/dose to as many as $10^{11}$ cells/dose), e.g., $1\times10^9$ cells. When the inventive CAR material is a nucleic acid packaged in a virus, an exemplary dose of virus may be 1 ng/dose.

For purposes of the invention, the amount or dose of the inventive CAR material administered should be sufficient to effect a therapeutic or prophylactic response in the subject or animal over a reasonable time frame. For example, the dose of the inventive CAR material should be sufficient to bind to antigen, or detect, treat or prevent disease, e.g., cancer, in a period of from about 2 hours or longer, e.g., about 12 to about 24 or more hours, from the time of administration. In certain embodiments, the time period could be even longer. The dose will be determined by the efficacy of the particular inventive CAR material and the condition of the animal (e.g., human), as well as the body weight of the animal (e.g., human) to be treated.

For purposes of the invention, an assay, which comprises, for example, comparing the extent to which target cells are lysed and/or IFN-γ is secreted by T cells expressing the inventive CAR upon administration of a given dose of such T cells to a mammal, among a set of mammals of which is each given a different dose of the T cells, could be used to determine a starting dose to be administered to a mammal. The extent to which target cells are lysed and/or IFN-γ is secreted upon administration of a certain dose can be assayed by methods known in the art.

When the inventive CAR materials are administered with one or more additional therapeutic agents, one or more additional therapeutic agents can be coadministered to the mammal. By "coadministering" is meant administering one or more additional therapeutic agents and the inventive CAR materials sufficiently close in time such that the inventive CAR materials can enhance the effect of one or more additional therapeutic agents, or vice versa. In this regard, the inventive CAR materials can be administered first and the one or more additional therapeutic agents can be administered second, or vice versa. Alternatively, the inventive CAR materials and the one or more additional therapeutic agents can be administered simultaneously. An exemplary therapeutic agent that can be co-administered with the CAR materials is IL-2. It is believed that IL-2 enhances the therapeutic effect of the inventive CAR materials. Without being bound by a particular theory or mechanism, it is believed that IL-2 enhances therapy by enhancing the in vivo expansion of the numbers of cells expressing the inventive CARs.

The mammal referred to herein can be any mammal. As used herein, the term "mammal" refers to any mammal, including, but not limited to, mammals of the order Rodentia, such as mice and hamsters, and mammals of the order Logomorpha, such as rabbits. The mammals may be from the order Carnivora, including Felines (cats) and Canines (dogs). The mammals may be from the order Artiodactyla, including Bovines (cows) and Swines (pigs) or of the order Perssodactyla, including Equines (horses). The mammals may be of the order Primates, Ceboids, or Simoids (monkeys) or of the order Anthropoids (humans and apes). Preferably, the mammal is a human.

With respect to the inventive methods, the cancer can be any cancer. In an embodiment of the invention, the cancer is a SLAMF7-expressing cancer. In an embodiment of the invention, the cancer is multiple myeloma.

As discussed herein, multiple myeloma, also known as plasma cell myeloma or Kahler's disease, is a cancer of plasma cells, which are a type of white blood cell normally responsible for the production of antibodies (Raab et al., *Lancet,* 374: 324-329 (2009)). Multiple myeloma affects 1-4 per 100,000 people per year. The disease is more common in men, and for yet unknown reasons is twice as common in African Americans as it is in Caucasian Americans. Multiple myeloma is the least common hematological malignancy (14%) and constitutes 1% of all cancers (Raab et al., supra). Treatment of multiple myeloma typically involves high-dose chemotherapy followed by hematopoietic stem cell transplanatation (allogenic or autologous); however, a high rate of relapse is common in multiple myeloma patients that have undergone such treatment. As discussed herein, SLAMF7 is highly expressed by multiple myeloma cells.

The terms "treat," and "prevent" as well as words stemming therefrom, as used herein, do not necessarily imply 100% or complete treatment or prevention. Rather, there are varying degrees of treatment or prevention of which one of ordinary skill in the art recognizes as having a potential benefit or therapeutic effect. In this respect, the inventive methods can provide any amount of any level of treatment or prevention of cancer in a mammal. Furthermore, the treatment or prevention provided by the inventive method can include treatment or prevention of one or more conditions or symptoms of the disease, e.g., cancer, being treated or prevented. Also, for purposes herein, "prevention" can encompass delaying the onset of the disease, e.g., cancer, or a symptom or condition thereof or preventing the recurrence of the disease, e.g., cancer.

Another embodiment of the invention provides any of the CARs (including functional portions and variants thereof) (alone or in combination with a suicide gene product), nucleic acids, systems, protein(s) (including combination(s) of proteins) encoded by the nucleic acids, recombinant expression vectors, host cells (including populations thereof) and/or pharmaceutical compositions described herein with respect to other aspects of the invention for use in a method of treating or preventing cancer in a mammal. Still another embodiment of the invention provides the use of any of the CARs (including functional portions and variants thereof) (alone or in combination with a suicide gene product), nucleic acids, systems, protein(s) (including combination(s) of proteins) encoded by the nucleic acids, recombinant expression vectors, host cells (including populations thereof) and/or pharmaceutical compositions described herein with respect to other aspects of the invention in the manufacture of a medicament for the treatment or prevention of cancer in a mammal. The cancer may be any of the cancers described herein.

The following examples further illustrate the invention but, of course, should not be construed as in any way limiting its scope.

EXAMPLES

The following materials and methods were employed in the experiments described in Examples 1-7 and 9-12.
Real-Time qPCR to Quantitate BCMA Transcript Copies SLAMF7 cDNA copies in samples of cDNA were quantitated from human tissues included in the Human Major Tissue qPCR panel II (ORIGENE™, Rockville, Md.) by performing qPCR with a SLAMF7-specific primer and probe set (available from Applied Biosystems, Grand Island, N.Y., catalog number 4331182). As a positive control, BCMA cDNA copies in cDNA of MM cells were quantitated from a plasmacytoma of a patient with advanced multiple myeloma. RNA was extracted from the plasmacytoma cells with an RNEASY™ mini kit (Qiagen, Venlo, Netherlands), and cDNA was synthesized with standard methods. A standard curve for the SLAMF7 qPCR was created by amplifying dilutions of a plasmid that encoded the full-length cDNA of BCMA (ORIGENE™). The qPCR accurately detected copy numbers from $10^2$ to $10^9$ copies of BCMA per reaction. The number of β-actin cDNA copies was quantitated in the same tissues with a TAQMAN™ (β-actin primer and probe kit (Applied Biosystems). A β-actin standard curve was created by amplifying serial dilutions of a β-actin plasmid. All qPCR reactions were carried out on a LIGHTCYCLER™ 480 machine (F. Hoffmann-La Roche Ltd).
Cell Lines and Primary Cells MM.1S is a SLAMF7$^+$ multiple myeloma cell line that was obtained from American Type Culture Collection (ATCC). A549 is a BCMA-negative lung cancer cell line (ATCC). TC71 is a BCMA-negative sarcoma cell line. CCRF-CEM, 293T, and A549 are SLAMF7-negative cell lines (ATCC). COL0207, HepG2, U251, Panc10.05, and TC71 are SLAMF7 cells lines that were kind gifts from Dr. Steven Rosenberg, National Cancer Institute. SLAMF7-K562 are K562 cells (ATCC) which were transduced with the gene for full-length SLAMF7. SLAMF7-RPMI are RPMI8226 cells (ATCC) which were transduced with the gene for full-length SLAMF7. NGFR-K562 are K562 cells which were transduced with the gene for low-affinity nerve growth factor (Kochenderfer et al., *J. Immunother.*, 32(7): 689-702 (2009)). All of the human samples mentioned were obtained from patients enrolled in IRB-approved clinical trials at the National Cancer Institute.
Constructing CARs Two CARs that contained anti-SLAMF7 scFvs were designed. The sequence of each CAR followed this pattern from the N-terminus to the C-terminus: CD8a signal sequence, anti-SLAMF7 scFv, human CD8a hinge and transmembrane domain, the cytoplasmic portion of human CD28, and the cytoplasmic portion of the human CD3ζ molecule. One CAR, designated Luc90-CD828Z, had a scFv derived from the murine Luc90 antibody. The Luc90 scFv had a sequence from N-terminus to C-terminus of light-chain variable domain, linker, and heavy-chain variable domain. Sequences of the Luc90 antibody light-chain and heavy-chain variable regions are publicly available (e.g., US Patent Application Publication 2006/0024296). The linker had the following sequence: GSTSGSGKPGSGEGSTKG (SEQ ID NO: 17). The second CAR, designated huLuc63-CD828Z had an identical sequence as Luc90-CD828Z except it had a scFv derived from the humanized Luc63 antibody. The sequences of the huLuc63 light-chain and heavy-chain are publicly available (e.g., US Patent Application Publication 2006/0024296). The sequences used for CD8a, CD28, and CD3ζ were obtained from the National Center for Biotechnology Information website. CARs with two different scFvs were used (see Kochenderfer et al., *J. Immunother.*, 32(7): 689-702 (2009) and Alabanza, et al., *Molecular Therapy*, 25(11): 2452-2465 (2017)). SP6-CD828Z CAR was used as a negative control. SP6-CD828Z recognizes a small molecule hapten but does not recognize human or mouse proteins.

Luc90-CD828Z was constructed as follows by following the design described above. A fragment encoding NcoI-CD8a signal sequence-Luc90 light chain variable region-linker-Luc90 heavy chain variable region-part of CD8a hinge-BlpI was optimized and synthesized by Invitrogen GENEART™ Gene Synthesis (ThermoFisher Scientific). This fragment was cloned into the MSGV1 gamma-retroviral backbone (Hughes, et al., *Human Gene Therapy*, 16(4): 457-472 (2005)). Luc90-CD8BBZ was constructed by replacing the CD28 moiety of Luc90-CD828Z with a 4-1BB moiety by using standard methods.

HuLuc63-CD828Z was constructed as follows by following the design described above. A fragment encoding NcoI-CD8a signal sequence-huLuc63 light chain variable region-linker-huLuc63 heavy chain variable region-part of CD8a hinge-BlpI was optimized and synthesized by Invnrogen GENEART™ Gene Synthesis (ThermoFisher Scientific). This fragment was cloned into the MSGV1 gamma-retroviral backbone.

Luc90-CD828Z CAR was selected for combination with a suicide gene. Combination Luc90-CD828Z plus suicide gene CAR constructs were designed (see Di Stasi, et al., *New England Journal of Medicine*, 365(18): 1673-1683 (2011); Clackson, et al., *Proceedings of the National Academy of Sciences of the United States of America*, 95(18): 10437-10442 (1998); and Straathof, et al., *Blood*, 105(11): 4247-4254 (2005)). IC9 was used as the suicide gene sequence. IC9 includes a 5' modified FK506 binding protein12 (FKBP12) component linked to a 3' caspase 9 component. FKBP12 is also referred to as FKBP1A. The FKBP12 component contains a FKBP12 sequence with the natural phenylalanine converted to valine at amino acid 39 (Clackson, supra); this amino acid conversion was made to decrease dimerization of FKBP12 by natural FKBP and increase dimerization by the small molecule AP1903. The FKBP12 sequence in IC9 was based on the natural FKBP12 sequence recorded in GenBank accession AH002818. The natural glycine amino acid at position 2 was replaced with a valine to generate a better Kozak sequence. The caspase 9 sequence used in IC9 was based on the natural caspase 9 sequence (GenBank accession NM_001229). AP1903 is also referred to as rimiducid. The linker sequence connecting the FKBP12 and caspase 9 components was Serine-Glycine-Glycine-Glycine-Serine (SEQ ID NO: 26). For both Luc90-CD828Z-IC9 and IC9-Luc90-CD828Z, the CAR and IC9 sequences were separated by a Thosea asigna virus 2A ("T2A," ASRAEGRGSLLTCGDVEENPGP, SEQ ID NO: 23) sequence which allows for 2 separate proteins to be expressed.

Two CAR plus suicide gene constructs were designed. The Luc90-CD828Z sequences described above were used. One construct has the IC9 suicide gene 5' to the CAR and is designated IC9-Lu90-CD828Z. The other CAR plus suicide gene construct has the IC9 suicide gene 3' to the CAR and is designated Luc90-CD828Z-IC9. DNA sequences encoding either IC9-Luc90-CD828Z or Luc90-CD828Z-IC9 were synthesized by Invitrogen GENEART™ Gene Synthesis (ThermoFisher Scientific) with a 5' Pml1 restriction site and a 3' EcoR1 restriction site. The synthesized DNA was ligated into the MSGV1 gammaretroviral vector backbone by standard methods.

CAR Detection on T Cells

T cells that were transduced with one of the CAR vectors and untransduced T cells were washed and stained with a BCMA-Fc protein labeled with phycoerythrin to detect cell-surface CAR molecules. Five-hundred thousand T cells were suspended in 50 mL of staining buffer, and a titered amount of the BCMA-Fc-PE reagent was added. Staining for CD3, CD4, and CD8 was also performed by using standard methods. Flow cytometry was performed by standard methods. Dead cells were excluded by using 7-AAD (BD Biosciences, San Jose, Calif.).

T-Cell Culture

PBMC were thawed and washed in T cell medium that contained AIM V™ medium (Invitrogen) plus 5% AB serum (Valley Biomedical, Winchester, Va.), 100 U/mL penicillin, and 100 µg/mL streptomycin. Prior to transductions, PBMC were suspended at a concentration of $1 \times 10^6$ cells/mL in T cell medium plus 50 ng/mL of the anti-CD3 monoclonal antibody OKT3 (Ortho, Bridgewater, N.J.) and 300 IU/mL of IL-2. After transductions, T cells were maintained in T-cell medium plus IL-2.

Gammaretroviral Transductions

To produce replication-incompetent gammaretroviruses, packaging cells were transfected with plasmids encoding CARs along with a plasmid encoding the RD114 envelope protein (see Kochenderfer et al., *J. Immunother.*, 32(7): 689-702 (2009)). Gammaretroviral transduction of T cells was performed 2 days after initiation of T-cell cultures.

Interferon-γ and Tumor Necrosis Factor Alpha ELISAs

One-hundred thousand SLAMF7$^+$ or SLAMF7-negative target cells were combined with 100,000 CAR-transduced T cells in duplicate wells of a 96 well round bottom plate in 2004 of AIM V™ medium (Invitrogen) plus 5% human serum. The plates were incubated at 37° C. for 18-20 hours. Following the incubation, ELISAs (enzyme-linked immunosorbent assays) for IFNγ were performed by using standard methods. Soluble SLAMF7 protein (ORIGENE™) was added to some ELISAs at the start of the co-culture to determine if soluble SLAMF7 had an impact on the ability of CAR T cells to recognize SLAMF7$^+$ targets.

CD107α Assay

For each T cell culture that was tested, two tubes were prepared. One tube contained MM.1S cells, and the other tube contained NGFR-K562 cells. Both tubes contained CAR-transduced T cells, 1 ml of AIM V™ medium (Invitrogen) plus 5% human AB serum, a titrated concentration of an anti-CD107a antibody (eBioscience, clone eBioH4A3, ThermoFisher Scientific), and 1 µL of GOLGISTOP™ (a protein transport inhibitor containing monensin, BD Biosciences). All tubes were incubated at 37° C. for 4 hours and then stained for CD3, CD4, and CD8.

Flow Cytometry

For anti-SLAMF7 staining, cells were stained with a commercially-available anti-SLAMF7 (anti-CD319) antibody from BD Biosciences. Flow cytometry staining for CD3, CD4, and CD8 was done by standard methods. Flow cytometry analysis for all experiments was performed by using FLOWJO™ software (Tree Star, Inc., Ashland, Oreg.).

6-Hour and 48-Hour Post-Rimiducid T Cell Death Analysis

On day 8 of culture, 1 million T cells from cultures that were either untransduced or transduced with one of the anti-SLAMF7 CARs cells were suspended at $1 \times 10^6$ T cells/mL in AIM V™ media (Invitrogen) plus 300 IU of interleukin-2. One million cells were added to each of 4 wells of a 12-well plate. A different concentration of AP1903 (MedChem Express, Princeton, N.J.) from was added to each well. AP1903 is also referred to as rimiducid. The concentrations of AP1903 evaluated were: 0, 1, 10, or 100 ng/mL.

Six hours and 48 hours after these cultures were set up, the cells were counted, washed, and stained with Protein L as described above. Next, the cells were washed twice with PBS, re-suspended in Annexin V binding buffer (BD Biosciences), and incubated with allophycocyanin-conjugated Annexin V (BD Biosciences) and 7AAD (BD Biosciences) for 15 minutes (mins) at room temp. The cells were immediately analyzed by flow cytometry.

Proliferation Assays

Cocultures were set up in 24-well plates. Target cells included in cocultures were either $0.5 \times 10^6$ irradiated SLAMF7-K562 cells or $0.5 \times 10^6$ irradiated NGFR-K562 cells. The cocultures also included $1 \times 10^6$ T cells from cultures that had been transduced with either anti-bcma2 or SP6. The T cells were labeled with carboxy fluorescein diacetate succinimidyl ester (CFSE, Invitrogen) as previously described. The medium used in the cocultures was AIM V™ (Invitrogen) plus 5% human AB serum. IL-2 was not added to the medium. Four days after initiation, the live cells in each coculture were counted with trypan blue for dead cell exclusion, and flow cytometry was performed by Protein L staining.

Cytotoxicity Assays

Cytotoxicity assays were conducted as previously described (see Kochenderfer et al., *J. Immunother.*, 32(7): 689-702 (2009)). Cytotoxicity was measured by comparing survival of SLAMF7$^+$ target cells relative to the survival of negative-control CCRF-CEM cells. Both of these cell types were combined in the same tubes with CAR-transduced T cells. CCRF-CEM negative control cells were labeled with the fluorescent dye 5-(and -6)-(((4-chloromethyl)benzoyl) amino) tetramethylrhodamine (CMTMR) (Invitrogen), and SLAMF7$^+$ target cells were labeled with CFSE. Cocultures were set up in sterile 5 mL test tubes (BD Biosciences) in duplicate at multiple T cell to target cell ratios. The target cells contained in the tubes were 50,000 SLAMF7$^+$ target cells along with 50,000 CCRF-CEM negative-control cells. The cultures were incubated for 4 hours at 37° C. Immediately after the incubation, 7AAD (7-amino-actinomycin D)

(BD Biosciences) was added, and flow cytometry acquisition was performed. For each T cell plus target-cell culture, the percent survival of SLAMF7$^+$ target cells was determined by dividing the percent live SLAMF7$^+$ cells by the percent live CCRF-CEM negative control cells. The corrected percent survival of SLAMF7$^+$ target cells was calculated by dividing the percent survival of SLAMF7$^+$ target cells in each T cell plus target cell culture by the ratio of the percent live SLAMF7$^+$ target cells to percent live CCRF-CEM negative-control cells in tubes containing only SLAMF7$^+$ target cells and CCRF-CEM cells without effector T cells. This correction was necessary to account for variation in the starting cell numbers and for spontaneous target cell death. Cytotoxicity was calculated as follows: the percent cytotoxicity of BCMA$^+$ target cells=100–corrected percent survival of SLAMF7$^+$ target cells.

Example 1

This example demonstrates that several classes of normal leukocytes express SLAMF7.

SLAMF7 is highly-expressed on MM cells but has a restricted expression pattern on essential normal cells. A factor for any CAR T-cell therapy is the expression pattern of the targeted antigen. A careful analysis of SLAMF7 expression in normal organs was conducted because CAR T cells can cause damage to tissues expressing the antigen targeted by the CAR. FIGS. 1A and 1B show results of quantitative PCR analysis of SLAMF7 RNA expression in normal organs. Low levels of SLAMF7 RNA were detected in some organs, which might be explained by SLAMF7$^+$ leukocytes infiltrating these organs. Next, SLAMF7 expression was assessed by immunohistochemistry (paraffin-fixed normal tissue microarray (Pantomics, number MN0661) was stained with anti-SLAMF7 clone 3B3 (LS Bio number LS-C340266)) (see Table A for the list of organs stained for SLAMF7 by immunohistochemistry and found to lack SLAMF7 expression (except on plasma cells and some macrophages and lymphocytes)). SLAMF7 expression was found only on plasma cells and to a lesser degree on some lymphocytes and macrophages. SLAMF7 expression on peripheral blood mononuclear cells was then assessed (FIG. 2). SLAMF7 expression was found on most NK cells, a large fraction of CD8+ T cells, and small fractions of monocytes and CD4$^+$ T cells. Hematopoietic stem cells express CD34. It is preferred that antigens targeted by CAR T cells not be expressed by CD34$^+$ cells. Next, SLAMF7 expression by CD34$^+$ hematopoietic cells was assessed, and it was determined that the CD34$^+$ cells did not express SLAMF7 (FIG. 3). Based on the finding of SLAMF7 expression on several classes of normal leukocytes, it appears that a clinically-proven suicide gene may improve any anti-SLAMF7 CAR T-cell strategy.

TABLE A

| | |
|---|---|
| adrenal | lung |
| bladder | ovary |
| bone | pancreas |
| breast | parathyroid |
| cerebellum | pituitary |
| cerebral cortex | placenta |
| eye | prostate |
| fallopian tube | skin |
| esophagus | spinal cord |
| stomach | spleen |
| small intestine | skeletal muscle |
| colon | testis |
| rectum | thy mus |
| heart | thyroid |
| kidney | tonsil |
| liver | uterine cervix |

Example 2

This example demonstrates that anti-SLAMF7 CARs can specifically recognize SLAMF7 and are not blocked by soluble SLAMF7.

CARs incorporating scFvs derived from either the Luc90 or Luc63 monoclonal antibodies (FIG. 4A-4E) were constructed. These CARs also included a hinge and transmembrane domain from CD8a, a CD28 costimulatory domain, and a CD3ζ T-cell activation domain. The CARs with Luc90 or huLuc63 scFvs were designated Luc90-CD828Z and huLuc63-CD828Z, respectively. FIG. 4C illustrates that the Luc90-CD8BBZ CAR has the same sequence as Luc90-CD828Z CAR except that the CD28 moiety in Luc90-CD828Z is replaced with a 4-1BB moiety. FIG. 4D illustrates that the Luc90-CD828Z-IC9 is made up of the same CAR sequence illustrated in FIG. 4A followed by the IC9 suicide gene. IC9 is made up of a modified FKBP12 domain followed by a modified caspase 9 sequence. FIG. 4E illustrates that IC9-Luc90-CD828Z is made up of IC9 followed by the same CAR sequence illustrated in FIG. 4A.

Table B-1 shows that the Luc90-CD828Z and huLuc63-CD828Z CARs (FIGS. 4A and 4B) were expressed on the surface of CAR T cells. T cells expressing either of the CARs could specifically recognize target cells expressing SLAMF7, as shown in Tables B-1 and B-2. Tables B-1 and B-2 show that high levels of IFNγ were produced when the CAR T cells were cultured with SLAMF7$^+$ target cells and that very low levels of IFNγ were produced when the CAR T cells were cultured with SLAMF7-negative target cells. CAR-expressing T cells cultured alone produced very low levels of IFNγ. IFNγ production of T cells expressing a CAR with a 4-1BB moiety, Luc90-CD8BBZ, was compared to IFNγ production of T cells expressing Luc90-CD828Z (Table C). Generally higher background cytokine release was found with the 4-1BB-containing CAR. Low levels of soluble SLAMF7 are found in the serum of some MM patients (see Tai, et al., *Blood*, 112(4): 1329-1337 (2008)). IFNγ ELISA assays were conducted to determine if adding SLAMF7 to cultures of anti-SLAMF7 CAR T cells plus target cells could block IFNγ release by the CAR T cells (Table D). IFNγ release by the CART cells was used as a measure recognition of the SLAMF7$^+$ target cells by the CAR T cells. The concentrations of soluble SLAMF7 added to the cultures were similar to those found in the blood of patients. Blocking of SLAMF7$^+$ target cell recognition by the soluble SLAMF7 was not observed. Also, activation of the anti-SLAMF7 CAR T cells by the soluble SLAMF7 was not observed. The SLAMF7-specific IFNγ release was greater for T cells expressing Luc90-CD828Z than for T cells expressing huLuc63-CD828Z in most experiments, which is consistent with results shown in Tables B1, B-2, and D. After results of several functional assays including ELISA assays and CD107a degranulation experiments, it was determined that the function of T cells expressing Luc90-CD828Z was superior to the function of T cells expressing huLuc63-CD828Z, and Luc90-CD828Z was selected for use in further experiments.

TABLE B-1

| T-cells | % CAR+ | Target cells | | | | |
|---|---|---|---|---|---|---|
| | | SLAMF7-RPMI | SLAMF7-K562 | 293T | COLO 205 | HepG2 |
| Luc90-CD828Z | 63 | 21293 | 16579 | 37 | 19 | 24 |
| Luc63-CD828Z | 62 | 8123 | 7106 | 38 | 29 | 33 |
| Untransduced | — | 109 | 59 | 19 | 11 | 39 |

TABLE B-2

| T-cells | Target cells | | | | | | |
|---|---|---|---|---|---|---|---|
| | SLAMF7-K562 | U251 | Panc 10.05 | NGFR-K562 | TC71 | A549 | T cells only |
| Luc90-CD828Z | 20055 | 27 | 36 | 45 | 82 | 79 | 29 |
| Luc63-CD828Z | 7524 | 46 | 53 | 78 | 113 | 76 | 71 |
| Untransduced | 65 | 21 | 15 | 54 | 24 | 14 | 12 |

Description of Tables B-1 and B-2

The T cells columns indicate whether T cells were transduced with Luc90-CD828Z, Luc63-CD828Z, or were untransduced. The % CAR+ in Table B-1 was determined by staining the T cells with Protein L. Except for the % CAR+ column, all values are pg/mL of IFN-gamma. T cells that were either untransduced or transduced with one of the indicated CARs were cultured with target cells overnight and a standard IFN-gamma ELISA was performed on the culture supernatant.

TABLE C

| T-cells | Target cells | | | | | | |
|---|---|---|---|---|---|---|---|
| | SLAMF7-RPMI8226 | SLAMF7-K562 | MM.1S | H929 | NGFR-K562 | CCRF-CEM | T cells only |
| Luc90-CD828Z | 20832 | 15759 | 4269 | 531 | 26 | 16 | 33 |
| Luc90-CD8BBZ | 19713 | 16697 | 5101 | 856 | 434 | 278 | 531 |
| Untransduced | 173 | 205 | 118 | 18 | 271 | 12 | 10 |

Description of Table C

All values are pg/mL of IFN-gamma. T cells that were either untransduced or transduced with one of the indicated CARs were cultured with target cells overnight, and a standard IFN-gamma ELISA was performed on the culture supernatant.

TABLE D

| T-cells | Target cells | | | | | | | | |
|---|---|---|---|---|---|---|---|---|---|
| | SLAMF7 RPMI 0 ng/ml | SLAMF7 RPMI 50 ng/ml | CD319 RPMI 200 ng/ml | NGFR K562 0 ng/ml | NGFR K562 50 ng/ml | NGFR K562 200 ng/ml | T cells 0 ng/ml | T cells 50 ng/ml | T cells 200 ng/ml |
| Luc90-CD828Z | 23538 | 23315 | 21301 | 267 | 223 | 224 | 172 | 160 | 41 |
| Luc63-CD828Z | 3495 | 2873 | 3083 | 191 | 98 | 83 | 20 | 22 | 30 |
| Untransduced | 504 | 451 | 501 | 564 | 433 | 507 | 23 | 22 | 25 |
| Targets alone | 5 | | 5 | 5 | | 5 | | | |
| | 200 ng/mL sSLAMF7 alone: 6 | | | | | | | | |

Description of Table D

The values in the cells are pg/mL of IFN-gamma. T cells that were either untransduced or transduced with one of the indicated CARs were cultured with target cells overnight, and a standard IFN-gamma ELISA was performed on the culture supernatant. The concentrations of 0, 50, or 200 ng/mL at the top of each column indicates the concentration of soluble SLAMF7 added to all T cell plus target cell overnight cultures in that column. The soluble SLAMF7 was added at the beginning of the overnight culture.

Example 3

This example demonstrates that T cells can be modified to express both an anti-SLAMF7 CAR and a suicide gene.

Two CAR constructs were designed that encoded Luc90-CD828Z and the IC9 suicide gene. The 2 genes were separated by a T2A ribosomal skip sequence. The design of these CAR constructs leads to expression of 2 separate proteins, the CAR protein, and the IC9 suicide protein. Diagrams of the 2 CAR+ suicide protein constructs, Luc90-CD828Z-IC9 and IC9-Luc90-CD828Z are shown in FIGS. 4A and 4B. The sequences differ only in the order of the 2 genes. The component CAR sequence and suicide protein sequence are identical for the 2 constructs.

The expression of the CAR on T cells that were transduced with gamma-retroviruses encoding each of 3 CAR constructs was assessed: Luc90-CD828Z, Luc90-CD828Z-IC9, and IC9-Luc90-CD828Z (FIG. 5). All CARs were expressed, but expression of the construct containing the CAR alone without the IC9 component was consistently higher than the expression the 2 CAR plus suicide gene constructs.

Example 4

This example demonstrates that anti-SLAMF7 CAR T cells specifically degranulate and produce IFNγ in response to SLAMF7$^+$ target cells.

The function of anti-SLAMF7 CARs was assessed next. T cells expressing Luc90-CD828Z with or without the IC9 suicide protein specifically recognized SLAMF7 and carried out a variety of functions. CART cells or untransduced T cells were assessed for CD107a upregulation, which is a marker of degranulation. Both CD4$^+$ CAR T cells (FIG. 6) and CD8$^+$ CAR T cells (FIG. 7) degranulated in response to the SLAMF7$^+$ cell line MM.1S. T cells modified to express Luc90-CD828Z either with or without the IC9 suicide protein also released IFNγ specifically in response to SLAMF7$^+$ target cells (Table E).

TABLE E

| | SLAMF7-K562 | MM.1S | NGFR-K562 | CCRF-CEM | T-cells Alone |
|---|---|---|---|---|---|
| UT | 90 | 87 | 85 | 13 | 14 |
| SP6 | 206 | 389 | 213 | 203 | 246 |
| Luc90-CD828Z-IC9 | 2249 | 1333 | 33 | 42 | 39 |
| IC9-Luc90-CD828Z | 2225 | 1849 | 30 | 33 | 38 |

Description of Table E

All values are pg/mL of IFN-gamma. T cells that were either untransduced or transduced with one of the indicated CARs were cultured with target cells overnight, and a standard IFN-gamma ELISA was performed on the culture supernatant.

Example 5

This example illustrates the cytotoxicity and proliferation of T cells expressing Luc90-CD828 in combination with IC9.

A cytotoxicity assessment of anti-SLAMF7 CAR T cells revealed that both Luc90-CD828Z and IC9-Luc90-CD828Z killed SLAMF7$^+$ target cells (FIG. 8A). T cells expressing either Luc90-CD828Z (FIG. 8B) or IC9-Luc90-CD828Z (FIG. 8C) proliferated specifically in response to SLAMF7$^+$ target cells.

Example 6

This example demonstrates that CD8 is expressed on activated T cells.

The T-cell culture process used in all examples herein involved stimulation of PBMC with the anti-CD3 monoclonal antibody OKT3 on day 0 with culture of the activated cells in IL-2-containing medium. SLAMF7 expression was assessed on T cells at day 3 of this culture process, and it was found that SLAMF7 was expressed on some activated CD8$^+$ T cells (FIG. 9). Compared to T-cell cultures from the same patient that were not transduced with anti-SLAMF7 CARs, there was an increase in the CD4:CD8 T-cell ratio in cultures of T cells expressing anti-SLAMF7 CARs (FIG. 10). This increase in CD4:CD8 ratio in cultures of T cells transduced with anti-SLAMF7 CARs suggests that the SLAMF7$^+$ CD8$^+$ T cells could have been eliminated by the anti-SLAMF7 CAR T cells. Despite possible elimination of some CD8$^+$ T cells from cultures transduced with anti-SLAMF7 CARs, the T cells in the cultures accumulated steadily (FIGS. 11A and 11B), indicating that it will be possible to produce sufficient numbers of cells for treatment of patients in clinical trials.

Example 7

This example demonstrates that the IC9 suicide protein is effective at eliminating anti-SLAMF7 CAR T cells.

Cultures of T cells expressing either Luc90-CD828Z-IC9 or IC9-Luc90-CD828Z were established and evaluated the efficiency of CAR T-cell elimination when AP1903, the dimerizer molecule that activates the IC9 suicide protein, was added to the cultures (FIGS. 12-15). Concentrations of AP1903 were added that were equal to concentrations of AP1903 achieved in clinical trials (Di Stasi, et al., *New England Journal of Medicine*, 365(18): 1673-1683 (2011) and Iuliucci, et al., *Journal of Clinical Pharmacology*, 41(8): 870-879 (2001)). T cells transduced with either Luc90-CD828Z or IC9-Luc90-CD828Z were efficiently eliminated when AP1903 was added to the T-cell cultures. There was a substantial loss of CAR$^+$ cells in the AP903-treated cultures, and most of the residual CAR$^+$ T cells were apoptotic. The elimination did not depend on the concentration of AP1903 added over the clinically-relevant range of concentrations tested. The elimination of CAR$^+$ T cells was slightly superior with the IC9-Luc90-CD828Z compared with Luc90-CD828Z-IC9, and functional parameters of IC9-Luc90-D828Z and Luc90-CD828Z-IC9 were similar, so IC9-Luc90-CD828Z was selected for further development.

In summary, CARs constructs expressing both the Luc90-CD828Z CAR and the IC9 suicide gene can specifically recognize SLAMF7 and perform a full range of T cell functions. T cells expressing these CAR plus suicide gene constructs can be eliminated on-demand, which may provide a safety feature when targeting SLAMF7 because SLAMF7 is expressed on a variety of normal leukocytes.

Example 8

This example demonstrates a method of treating cancer using anti-SLAMF7 CAR T cells.

In a planned clinical trial, unselected peripheral blood mononuclear cells will be stimulated with the anti-CD3 antibody OKT3 prior to transduction. Total cell culture time will be 7 to 9 days.

All patients on the trial will receive a conditioning chemotherapy regimen of 300 mg/m$^2$ of cyclophosphamide daily for 3 days plus 30 mg/m$^2$ of fludarabine daily for 3 days on the same days as cyclophosphamide.

Two days after the end of the conditioning chemotherapy, patients will receive a single dose of anti-SLAMF7 CAR T cells. The trial will be a dose escalation with a standard 3×3 design. The following dose levels will be included (Table F):

TABLE F

| Dose Level | Dose of CAR + T cells/kg |
|---|---|
| −1 | $0.25 \times 10^6$ |
| 1 | $0.5 \times 10^6$ |
| 2 | $1.0 \times 10^6$ |
| 3 | $2.0 \times 10^6$ |
| 4 | $4.0 \times 10^6$ |
| 5 | $8.0 \times 10^6$ |

Protocol accrual will start on Dose Level 1. A minimum of 3 patients will be enrolled on each dose level. If no patient treated on a dose level experiences a dose limiting toxicity (DLT), accrual will proceed on the next higher dose level. If 1 of 3 patients on a dose level experiences a DLT, 3 more patients will be treated on the same dose level without a DLT to allow accrual of patients on the next higher dose level. If 2 or more DLTs occur on a dose level, the next lowest dose level will be identified as the maximum tolerated dose. A Dose Level-1 will be included only in case 2 or more DLTs occur on Dose Level 1. After a maximum tolerated dose is established, an expansion cohort of a maximum of 10 patients will be treated. Six patients will be treated on each of Dose Levels 1 to 5 plus 10 on the expansion cohort.

For careful observation for potential toxicities, all patients will have a mandatory hospitalization for 9 days after cell infusion at the National Institutes of Health Clinical Center. Rimiducid will only be administered to eliminate CAR T cells in cases of unacceptable toxicity. It is anticipated that the most likely toxicities requiring rimiducid administration will be cytopenias, especially NK cell deficiency. Rimiducid will be administered in the event of prolonged clinically-significant deficiencies of other cells such as monocytes or platelets. In the case of NK cell deficiency, rimiducid will be administered to patients having infections with herpes viruses such as cytomegalovirus because Herpesvirus infections are thought to be controlled by NK cells. Rimiducid might also be needed to control severe cytokine-release syndrome, which is a common toxicity after CAR T-cell infusions. If rimiducid is infused, blood will be collected for monitoring CAR T-cell levels just before the infusion and every other day for 6 days after the infusion.

Example 9

This example demonstrates the in vivo anti-tumor efficacy and non-toxicity of human T cells expressing IC9-Luc90-CD828Z.

First, MM.1S human SLAMF7$^+$ multiple myeloma cell line tumors were established in immunodeficient mice. In this model, the MM.1S cells formed a solid cutaneous mass. Measurable tumors were allowed to develop over 7 days, and then the mice were treated with a single intravenous infusion of MSGV1-IC9-Luc90-CD828Z-transduced human T cells. NSG mice (NOD.Cg-Prkdc$^{scid}$ Il2rg$^{tm1Wjl}$/SzJ) from The Jackson Laboratory, Bar Harbor, Me., were used. Mice received intradermal injections of $4 \times 10^6$ MM.1S cells. The cells were suspended in a 1:1 mixture of MATRIGEL™ gelatinous protein mixture (BD Biosciences) and PBS (Phosphate-buffered saline) for injection. Tumors were allowed to grow for 7 days, and then each mouse received a single intravenous infusion of human T cells that were transduced with one of 3 CARs: IC9-Luc90-CD828Z (suicide gene+anti-SLAMF7 CAR), Luc90-CD828Z (anti-SLAMF7 CAR alone), or a negative-control anti-CD19 CAR Hu19-CD828Z. A 4th group was left untreated. All groups included 5 mice. After CAR T-cell infusion, the tumors were measured with calipers every 3 days. The longest length and the length perpendicular to the longest length and the tumor thickness were multiplied together to obtain the tumor volume in mm$^3$. When the longest length reached 15 mm, mice were sacrificed. Animal studies were approved by the National Cancer Institute Animal Care and Use Committee.

FIGS. 16A-16B show a dose-titration of IC9-Luc90-CD828Z-expressing T cells. In this experiment, immunocompromised NSG mice were injected intradermally with $4 \times 10^6$ MM.1S cells to form a solid mass. Mice were then treated with a single infusion of $0.5 \times 10^6$, $2 \times 10^6$, or $8 \times 10^6$, IC9-Luc90-CD828Z-expressing T cells. The $8 \times 10^6$ and $2 \times 10^6$ CAR$^+$ T cell dose eliminated all tumors. The $0.5 \times 10^6$ CAR$^+$ T cell dose only slightly slowed tumor growth relative to untreated mice but did not eliminate any tumors. The tumor volume curves end when the first mouse of a group was sacrificed. Mice receiving IC9-Luc90-CD828Z-expressing T cells did not exhibit any signs of CAR T-cell-mediated toxicity. The mice did not exhibit ruffled fur or decreased activity, and mice died only when sacrificed at the end of the experiments or when sacrificed after large tumors developed.

Example 10

This example demonstrates the in vivo anti-tumor efficacy and non-toxicity of human T cells expressing IC9-Luc90-CD828Z.

MM.'S tumors were established in NSG mice as described in Example 9. FIGS. 17A-17B show results in which mice bearing MM.1S tumors were treated with T cells expressing one of 3 different CARs: IC9-Luc90-CD828Z (suicide gene+anti-SLAMF7 CAR), Luc90-CD828Z (anti-SLAMF7 CAR alone), or a negative-control anti-CD19 CAR Hu19-CD828Z. A 4th group was left untreated in both experiments. All groups included 5 mice. The CARP T cell dose was 2 million CARP T cells per mouse. There were 5 mice in all groups. T cells expressing either anti-SLAMF7 CAR exhibited powerful anti-tumor activity, and all mice in the control groups were sacrificed when progressive tumors reached 15 mm in largest diameter. None of the mice receiving anti-SLAMF7 CAR-expressing T cells exhibited any signs of CAR T-cell-mediated toxicity. The mice did not exhibit ruffled fur or decreased activity, and mice died only when sacrificed at the end of the experiments or when sacrificed after large tumors developed.

The data show that IC9-Luc90-CD828Z-expressing T cells have a dose-dependent activity against established tumors of a human multiple myeloma cell line. At a dose of 2 million or more IC9-Luc90-CD828Z-expressing T cells per mouse, tumors can be eradicated, and mice survive long-term.

Example 11

This example demonstrates that administration of AP1903 can abrogate CAR T-cell activity in mice receiving IC9-Luc90-CD828Z CAR T cells.

MM.1S tumors were established in NSG mice as described in Example 9. The mice were treated with $2 \times 10^6$ IC9-Luc90-CD828Z T cells. The mice received 5 mg/kg of AP1903 intraeritoneally for either 3 days or 12 days after the CAR T-cell infusion. The mice receiving AP1903 had progressive tumors while the mice receiving the vehicle control instead of AP1903 exhibited tumor elimination (FIG. 18). Also levels of IC9-Luc90-CD828Z CART cells in the mice receiving AP1903 were reduced as compared to the mice receiving the vehicle.

Example 12

This example demonstrates that in a mouse model, IC9-Luc90-CD828Z CAR T cells are safe to administer.

Preclinical mouse studies showed no toxicity to IC9-Luc90-CD828Z CAR T cells in mice. In all mouse experiments, mice did not experience any signs of toxicity after the CARP T-cell infusions.

All references, including publications, patent applications, and patents, cited herein are hereby incorporated by reference to the same extent as if each reference were individually and specifically indicated to be incorporated by reference and were set forth in its entirety herein.

The use of the terms "a" and "an" and "the" and "at least one" and similar referents in the context of describing the invention (especially in the context of the following claims) are to be construed to cover both the singular and the plural, unless otherwise indicated herein or clearly contradicted by context. The use of the term "at least one" followed by a list of one or more items (for example, "at least one of A and B") is to be construed to mean one item selected from the listed items (A or B) or any combination of two or more of the listed items (A and B), unless otherwise indicated herein or clearly contradicted by context. The terms "comprising," "having," "including," and "containing" are to be construed as open-ended terms (i.e., meaning "including, but not limited to,") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

Preferred embodiments of this invention are described herein, including the best mode known to the inventors for carrying out the invention. Variations of those preferred embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

The invention claimed is:

1. A nucleic acid comprising:
   (a) a suicide gene; and
   (b) a nucleotide sequence encoding a chimeric antigen receptor (CAR), wherein the CAR comprises a single chain comprising an antigen recognition domain, a transmembrane (TM) domain, and a T cell activation domain, wherein the CAR has antigenic specificity for signaling lymphocyte activating molecule F7 (SLAMF7), wherein the TM domain comprises a TM domain of CD8α or CD28, wherein the antigen recognition domain comprises the amino acid sequences of SEQ ID NOs: 1-6;
   wherein the nucleotide sequence encoding the CAR is positioned 3' of the suicide gene, and wherein the suicide gene is an inducible caspase 9 (IC9) gene.

2. The nucleic acid of claim 1, wherein the antigen recognition domain comprises the amino acid sequences of SEQ ID NOs: 13-14.

3. The nucleic acid of claim 1, wherein the T-cell activation domain comprises a T-cell signaling domain of any one of the following proteins: a human CD28 protein, a human CD3-zeta protein, a human FcRγ protein, a CD27 protein, an OX40 protein, a human 4-1BB protein, a human inducible T-cell costimulatory protein (ICOS), modified versions of any of the foregoing, or any combination of the foregoing.

4. The nucleic acid of claim 1, further comprising a nucleotide sequence encoding a cleavable linker sequence.

5. The nucleic acid of claim 4, wherein the nucleotide sequence encoding the cleavable linker sequence is positioned between the nucleotide sequence encoding the CAR and the suicide gene.

6. The nucleic acid of claim 1, wherein the nucleotide sequence encodes the amino acid sequence of any one of SEQ ID NOs: 27, 29 and 31.

7. The nucleic acid according to claim 1, wherein the TM domain consists of a TM domain of CD8α or CD28.

8. A vector comprising the nucleic acid of claim 1.

9. An isolated host cell comprising the vector of claim 8.

10. The isolated host cell of claim 9, wherein the host cell is a T-cell.

11. The isolated host cell of claim 9, wherein the host cell is a natural killer (NK) cell.

12. A population of cells comprising at least one host cell of claim 9.

13. A method of treating or preventing cancer in a mammal, the method comprising administering to the mammal the nucleic acid of claim 1, in an amount effective to treat or prevent cancer in the mammal.

14. The method according to claim 13, wherein the cancer is multiple myeloma.

15. A nucleic acid comprising:
    (a) a suicide gene; and
    (b) a nucleotide sequence encoding a chimeric antigen receptor (CAR), wherein the CAR comprises a single chain comprising, from the N-terminus to the C-terminus: a CD8α signal sequence, an antigen recognition domain, a human CD8 α hinge and transmembrane domain, a cytoplasmic portion of human CD28, and a cytoplasmic portion of human CD3ζ,
    wherein the CAR has antigenic specificity for signaling lymphocyte activating molecule F7 (SLAM F7),
    wherein the antigen recognition domain comprises the amino acid sequences of SEQ ID NOs: 1-6;
    wherein the nucleotide sequence encoding the CAR is positioned 3' of the suicide gene, and wherein the suicide gene is an inducible caspase 9 (IC9) gene.

16. The nucleic acid of claim 15, wherein the antigen recognition domain comprises the amino acid sequences of SEQ ID NOs: 13-14.

* * * * *